United States Patent
Sagehashi et al.

(10) Patent No.: US 9,758,609 B2
(45) Date of Patent: Sep. 12, 2017

(54) MONOMER, POLYMER, RESIST COMPOSITION, AND PATTERNING PROCESS

(71) Applicant: Shin-Etsu Chemical Co., Ltd., Tokyo (JP)

(72) Inventors: Masayoshi Sagehashi, Joetsu (JP); Koji Hasegawa, Joetsu (JP); Kazuhiro Katayama, Joetsu (JP); Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/972,612

(22) Filed: Dec. 17, 2015

(65) Prior Publication Data

US 2016/0179002 A1   Jun. 23, 2016

(30) Foreign Application Priority Data

Dec. 18, 2014  (JP) ................................ 2014-256295
Sep. 11, 2015  (JP) ................................ 2015-179394

(51) Int. Cl.
| | |
|---|---|
| G03F 7/004 | (2006.01) |
| G03F 7/038 | (2006.01) |
| G03F 7/039 | (2006.01) |
| C08F 220/28 | (2006.01) |
| C08F 220/20 | (2006.01) |
| C08F 224/00 | (2006.01) |
| C07C 69/54 | (2006.01) |

(52) U.S. Cl.
CPC ............ *C08F 224/00* (2013.01); *C07C 69/54* (2013.01); *C08F 220/20* (2013.01); *C08F 220/28* (2013.01); *G03F 7/0045* (2013.01); *G03F 7/0046* (2013.01); *G03F 7/0382* (2013.01); *G03F 7/0397* (2013.01); *C07C 2101/14* (2013.01); *C07C 2102/42* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 6,800,423 B2 | 10/2004 | Yokoyama et al. | |
| 7,300,739 B2 | 11/2007 | Allen et al. | |
| 7,563,558 B2 | 7/2009 | Allen et al. | |
| 8,227,183 B2 | 7/2012 | Tsubaki et al. | |
| 2002/0072579 A1* | 6/2002 | Hasegawa | C07C 69/608 526/281 |
| 2002/0087033 A1* | 7/2002 | Hasegawa | C07C 33/14 568/817 |
| 2009/0053657 A1* | 2/2009 | Hatakeyama | C09D 133/066 430/324 |
| 2012/0202158 A1* | 8/2012 | Hatakeyama | G03F 7/0045 430/325 |
| 2013/0084517 A1* | 4/2013 | Suka | G03F 7/0046 430/5 |

FOREIGN PATENT DOCUMENTS

| | | | |
|---|---|---|---|
| JP | 2003-195502 A | | 7/2003 |
| JP | 2005-3862 A | | 1/2005 |
| JP | 2005-3863 A | | 1/2005 |
| JP | 2006-145775 A | | 6/2006 |
| JP | 2006-215067 A | | 8/2006 |
| JP | 2006-317803 A | | 11/2006 |
| JP | 2007-322660 | * | 12/2007 |
| JP | 2009-251392 | * | 10/2009 |
| JP | 4554665 B2 | | 9/2010 |
| JP | 2010-286831 | * | 12/2010 |
| JP | 2011-141495 | * | 7/2011 |
| JP | 2012-092086 | * | 5/2012 |
| WO | 2004/074936 A1 | | 9/2004 |
| WO | 2011/087144 A1 | | 7/2011 |

OTHER PUBLICATIONS

Machine translation of jp-2007-322660 (2007).*
Machine translation of jp-2011-141495 (2011).*
Sooriyakumaran et al., "193-nm Negative Resist Based on Acid-Catalyzed Elimination of Polar Molecules", Advances in Resist Technology and Processing XXI, Proceedings of SPIE, 2004, vol. 5376, pp. 71-78, (8 pages).
Iwato, Kaoru, "Actinic ray- or radiation-sensitive resin composition for resist film and pattern formation method for manufacturing electronic devices using the same", Chemical Abstracts Service, Ohio, Database accession No. 2013:1906228 (1 page).
Search Report dated Jun. 20, 2016, issued in counterpart European Application No. 15200064.2 (11 pages).

* cited by examiner

*Primary Examiner* — Martin Angebranndt
(74) *Attorney, Agent, or Firm* — Westerman, Hattori, Daniels & Adrian, LLP

(57) ABSTRACT

A monomer having a plurality of tertiary alcoholic hydroxyl groups is provided. A useful polymer is obtained by polymerizing the monomer. From a resist composition comprising the polymer, a negative pattern which is insoluble in alkaline developer and has high etch resistance is formed at a high resolution.

9 Claims, No Drawings

MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application Nos. 2014-256295 and 2015-179394 filed in Japan on Dec. 18, 2014 and Sep. 11, 2015, respectively, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, the self-aligned double patterning (SADP) process of adding film to opposite sidewalls of lines of a resist pattern resulting from ArF lithography for thereby forming two patterns with half line width from one pattern is successful in manufacturing microelectronic devices at the 20-nm node in a mass scale. As the miniaturization technology for microelectronic devices of the next generation 10-nm node, the self-aligned quadruple patterning (SAQP) which is double repetition of SADP is a candidate. It is pointed out that this process is quite expensive because formation of sidewall film by CVD and processing by dry etching are repeated several times. Extreme ultraviolet (EUV) lithography of wavelength 13.5 nm is capable of forming a pattern with a size of the order of 10 nm via single exposure, but suffers from the problems of still low laser power and low productivity. As the miniaturization technology comes to the deadlock, the development of three-dimensional devices such as vertically stacked flash memories typically BiCS is started, but expected to be a high cost process.

Recently, a highlight is put on the organic solvent development again. A positive resist composition featuring a high resolution is subjected to organic solvent development to form a negative pattern. As the ArF resist composition for negative tone development with organic solvent, positive ArF resist compositions of the prior art design may be used. Such a pattern forming process is described in Patent Document 1.

In the process of forming a negative tone pattern via organic solvent development, a film from which a robust protective group such as cyclic structure having dry etch resistance has been eliminated is left as the negative pattern. Thus the film is short of dry etch resistance. This serious problem must be overcome before the negative pattern formation via organic solvent development can be implemented.

On the other hand, studies have also been made on the negative pattern formation via development in alkaline aqueous solution. Known resist compositions used in this process include a negative resist composition of polarity switch type comprising a base resin comprising recurring units having γ-hydroxycarboxylic acid which forms lactone ring by PEB (see Patent Document 2), a negative resist composition comprising a copolymer comprising alcoholic hydroxyl-containing (meth)acrylate units and fluoroalcohol-containing units and a crosslinker (see Patent Document 3), and negative resist compositions of crosslinking type comprising a crosslinker and a combination of α-hydroxyacrylate and lactone units (see Patent Document 4), α-hydroxyacrylate and fluoroalcohol units (see Patent Documents 5 to 7), and mono(meth)acryloyloxypinacol and fluoroalcohol units (see Patent Document 8).

Of these, Patent Document 2 describes a negative resist composition of polarity switch type, not resorting to crosslinking reaction, in which γ-hydroxycarboxylic acid units incur swell of the pattern after development. Patent Documents 3 to 7 relate to negative resist compositions of crosslinking type. Although the negative pattern formation by cooperation of alcoholic hydroxyl group and crosslinker has the problems of bridging between pattern features and pattern collapse due to swell, it is observed that the incorporation of fluoroalcohol units has a swell-reducing effect. Moreover, as recent examples of negative pattern formation by polarity switch, there are proposed base resins having polar units such as tertiary hydroxyl group, tertiary ether bond, tertiary ester bond or acetal bond as the polarity switch group. Of these, a polymer using a polar unit having one tertiary hydroxyl group is unlikely to swell after development. However, the difference of dissolution rate in developer between unexposed and exposed regions is insufficient, which raises the problem that a footing occurs at the bottom of a line-and-space pattern, that is, pattern features take a tapered shape. See Patent Documents 9 and 10 and Non-Patent Document 1.

All the negative pattern forming processes mentioned above are effective to some extent in forming pattern features with a size of the order of 100 nm. However, their performance is insufficient in forming pattern features with a size of finer than 100 nm, because pattern bridging and collapse due to swell, and footing at the pattern bottom inevitably occur. Although active efforts have recently been devoted on the negative pattern forming process via organic solvent development, the organic solvent used as the developer is more expensive than conventional alkaline developers. From the standpoint of etch resistance improvement, it is desired to have a negative resist composition which is amenable to conventional alkaline development at a high resolution and allows a robust backbone structure to be left in the film after development.

CITATION LIST

Patent Document 1: JP 4554665 (U.S. Pat. No. 8,227,183)
Patent Document 2: JP-A 2003-195502
Patent Document 3: WO 2004/074936
Patent Document 4: JP-A 2005-003862
Patent Document 5: JP-A 2005-003863
Patent Document 6: JP-A 2006-145775
Patent Document 7: JP-A 2006-317803
Patent Document 8: JP-A 2006-215067
Patent Document 9: U.S. Pat. No. 7,300,739
Patent Document 10: U.S. Pat. No. 7,563,558
Non-Patent Document 1: Proc. SPIE vol. 5376, p 71 (2004)

DISCLOSURE OF INVENTION

The requirements for further miniaturization continue severer in these years. In the negative pattern forming process via organic solvent development, on which active efforts have been devoted, the negative pattern defined in the resist film has a reduced carbon density as compared with that prior to exposure. It is then desired to improve the resistance to etching of the resist film and the retention of pattern shape after etching.

An object of the invention is to provide a polymerizable monomer having a substituent group capable of polarity switch under the action of acid, a polymer derived from the monomer, a resist composition comprising the polymer, and a pattern forming process using the composition.

The inventors have found that a monomer having the formula (1) defined below is readily prepared, and that a resist composition comprising a polymer derived from the monomer as base resin forms at a high resolution a negative pattern insoluble in alkaline developer and having high etch resistance.

In one aspect, the invention provides a monomer having the formula (1).

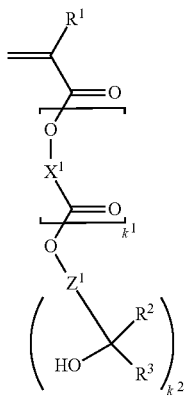

(1)

Herein $R^1$ is hydrogen or methyl, $R^2$ and $R^3$ are each independently a straight, branched or cyclic $C_1$-$C_{10}$ monovalent hydrocarbon group, $R^2$ and $R^3$ may bond together to form an alicyclic group with the carbon atom to which they are attached, $X^1$ is a straight, branched or cyclic $C_1$-$C_{20}$ divalent hydrocarbon group in which any constituent —$CH_2$— moiety may be replaced by —O— or —C(=O)—, $Z^1$ is a straight, branched or cyclic $C_1$-$C_{20}$ aliphatic hydrocarbon group in which any constituent —$CH_2$— moiety may be replaced by —O— or —C(=O)—, $k^1$ is 0 or 1, and $k^2$ is an integer of 2 to 4.

Preferably, $Z^1$ is a cyclic $C_3$-$C_{20}$ aliphatic hydrocarbon group.

In another aspect, the invention provides a polymer comprising recurring units having the formula (3).

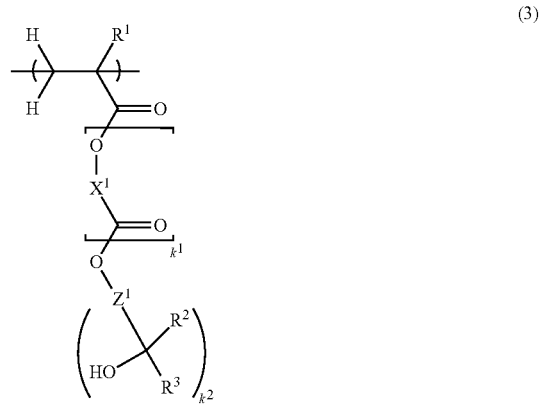

(3)

Herein $R^1$, $R^2$, $R^3$, $X^1$, $Z^1$, $k^1$, and $k^2$ are as defined above.

In a preferred embodiment, the polymer further comprises recurring units of at least one type selected from recurring units having formulae (A) to (D).

(A)

(B)

(C)

(D)

Herein $R^1$ is as defined above, $Z^A$ is a $C_1$-$C_{20}$ fluoroalcohol-containing group, $Z^B$ is a $C_1$-$C_{20}$ phenolic hydroxyl-containing group, $Z^C$ is a $C_1$-$C_{20}$ carboxyl-containing group, $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^2$ is a single bond, methylene, ethylene, phenylene, fluorinated phenylene, naphthylene, —O—$R^{01}$—, or —C(=O)—$Z^2$—$R^{01}$—, $Z^2$ is oxygen or NH, and $R^{01}$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

In a further aspect, the invention provides a resist composition comprising a base resin, an acid generator, and an organic solvent, the base resin comprising the polymer defined above.

In a yet further aspect, the invention provides a pattern forming process comprising the steps of applying the resist composition defined above onto a substrate, baking to form a resist film, exposing the resist film to high-energy radiation to define exposed and unexposed regions, baking, and developing the exposed resist film in a developer to form a pattern.

In a preferred embodiment, the developing step uses an alkaline developer in which the unexposed region of resist film is dissolved and the exposed region of resist film is not dissolved, for forming a negative tone pattern.

Advantageous Effects of Invention

The inventive monomer is particularly useful for the preparation of a polymer which is used as a base resin to formulate a radiation-sensitive resist composition having high transparency to radiation of wavelength 500 nm or less, especially 300 nm or less, e.g., KrF, ArF or $F_2$ laser radiation, and improved development properties. Using a polymer comprising recurring units derived from the inventive monomer as base resin, a resist composition is formulated. From the resist composition, a negative pattern insoluble in alkaline developer and having high etch resistance can be formed at a high resolution.

DESCRIPTION OF EMBODIMENTS

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond. Me stands for methyl, Ph for phenyl, and Ac for acetyl.

The abbreviations and acronyms have the following meaning.

EUV: extreme ultraviolet

PAG: photoacid generator

Mw: weight average molecular weight

Mn: number average molecular weight

Mw/Mn: molecular weight distribution or dispersity

GPC: gel permeation chromatography

PEB: post-exposure bake

LWR: line width roughness

It is understood that for some structures represented by chemical formulae, there can exist enantiomers and diastereomers because of the presence of asymmetric carbon atoms. In such a case, a single formula collectively represents all such isomers. The isomers may be used alone or in admixture.

Monomer

The invention provides a monomer having the formula (1).

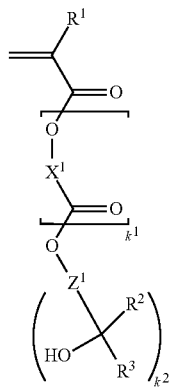

(1)

Herein $R^1$ is hydrogen or methyl. $R^2$ and $R^3$ are each independently a straight, branched or cyclic $C_1$-$C_{10}$ monovalent hydrocarbon group, $R^2$ and $R^3$ may bond together to form an alicyclic group with the carbon atom to which they are attached. $X^1$ is a straight, branched or cyclic $C_1$-$C_{20}$ divalent hydrocarbon group in which any constituent —$CH_2$— moiety may be replaced by —O— or —C(=O)—. $Z^1$ is a straight, branched or cyclic $C_1$-$C_{20}$ aliphatic hydrocarbon group in which any constituent —$CH_2$— moiety may be replaced by —O— or —C(=O)—, $k^1$ is 0 or 1, and $k^2$ is an integer of 2 to 4.

Typical of the straight, branched or cyclic $C_1$-$C_{10}$ monovalent hydrocarbon group are alkyl groups including methyl, ethyl, propyl, isopropyl, n-butyl, s-butyl, t-butyl, cyclopentyl, cyclohexyl, 2-ethylhexyl, n-octyl, norbornyl, tricyclodecanyl, and adamantyl.

Examples of the straight, branched or cyclic $C_1$-$C_{20}$ divalent hydrocarbon group are given below, but not limited thereto.

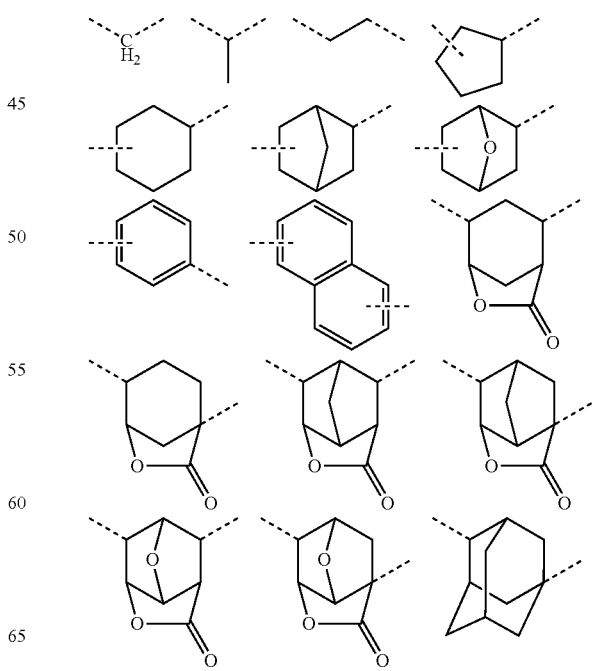

-continued

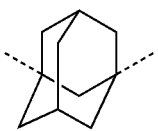

Examples of the straight, branched or cyclic $C_1$-$C_{20}$ aliphatic hydrocarbon group of $Z^1$ are given below, but not limited thereto.

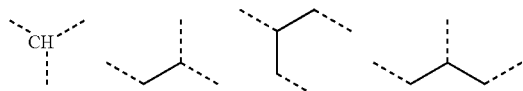

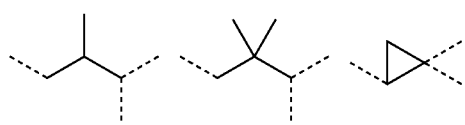

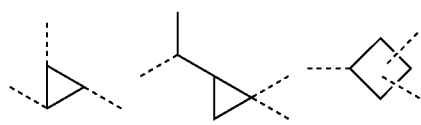

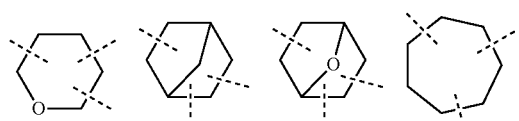

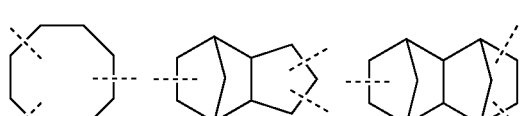

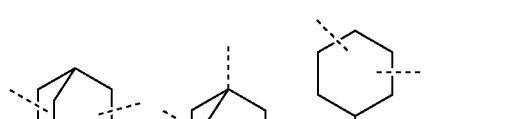

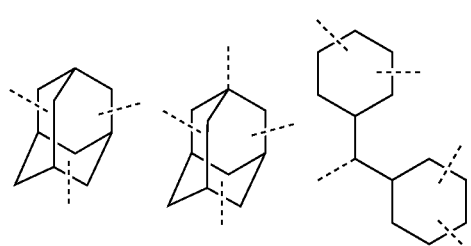

Among others, $Z^1$ is preferably a cyclic $C_3$-$C_{20}$ aliphatic hydrocarbon group, more preferably a group having cyclohexane ring structure (inclusive of bridged ring such as norbornane ring). In this case, the preferred monomer has the formula (2), but is not limited thereto.

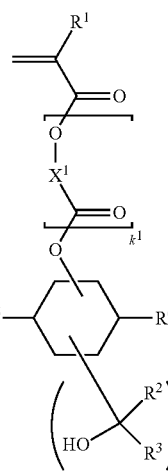

(2)

Herein $R^1$ to $R^3$, $X^1$, $k^1$ and $k^2$ are as defined above. $R^5$ and $R^6$ are hydrogen or may, taken together, form an optionally substituted methylene or ethylene group or —O—.

Examples of suitable recurring units derived from the monomer having formula (1) are shown below, but not limited thereto.

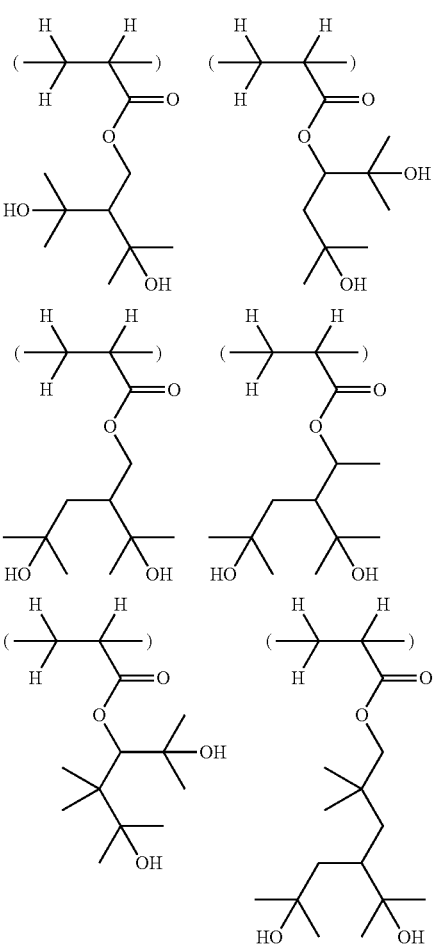

-continued
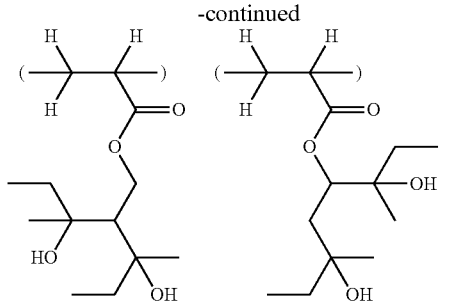
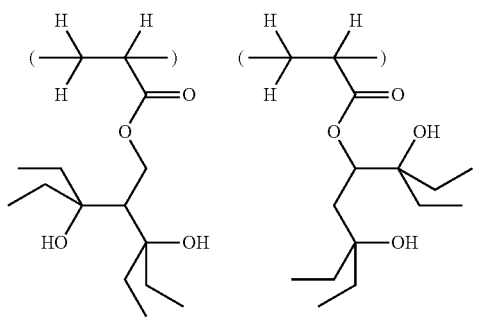
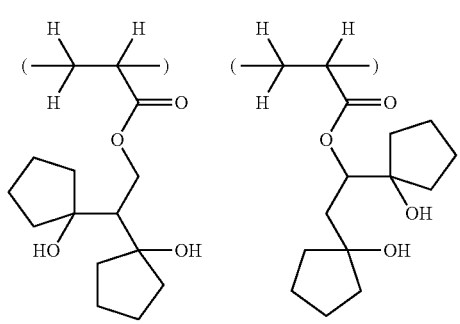
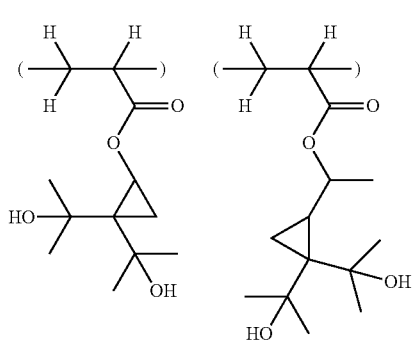
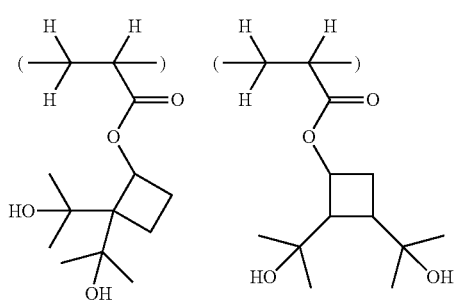
-continued
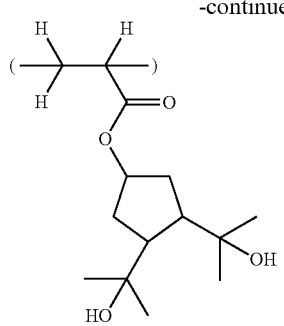
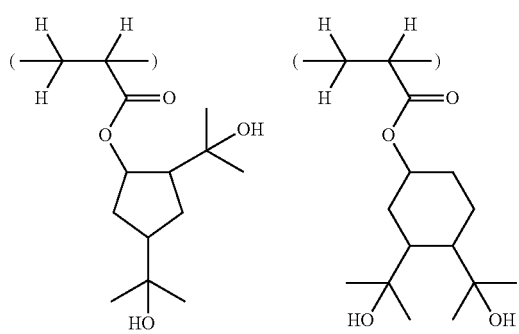
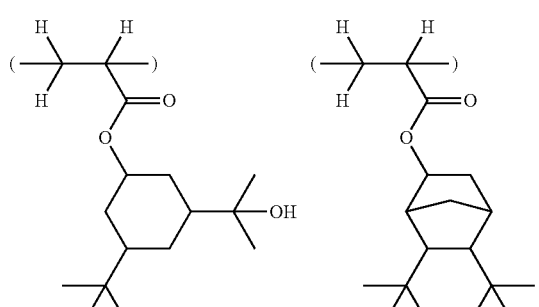
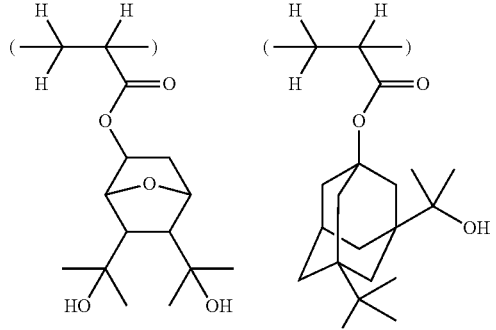
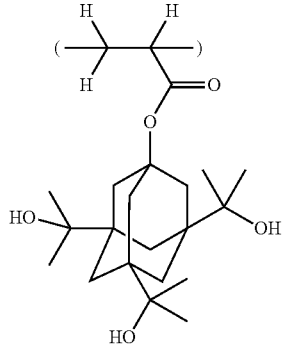

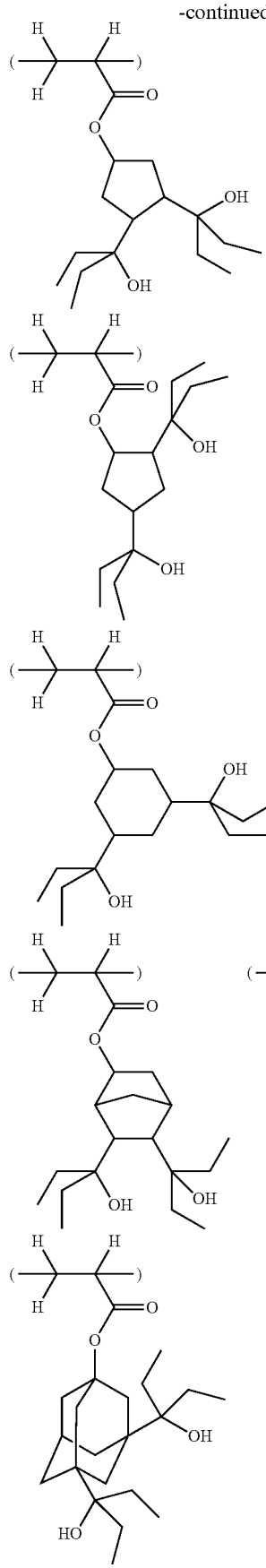
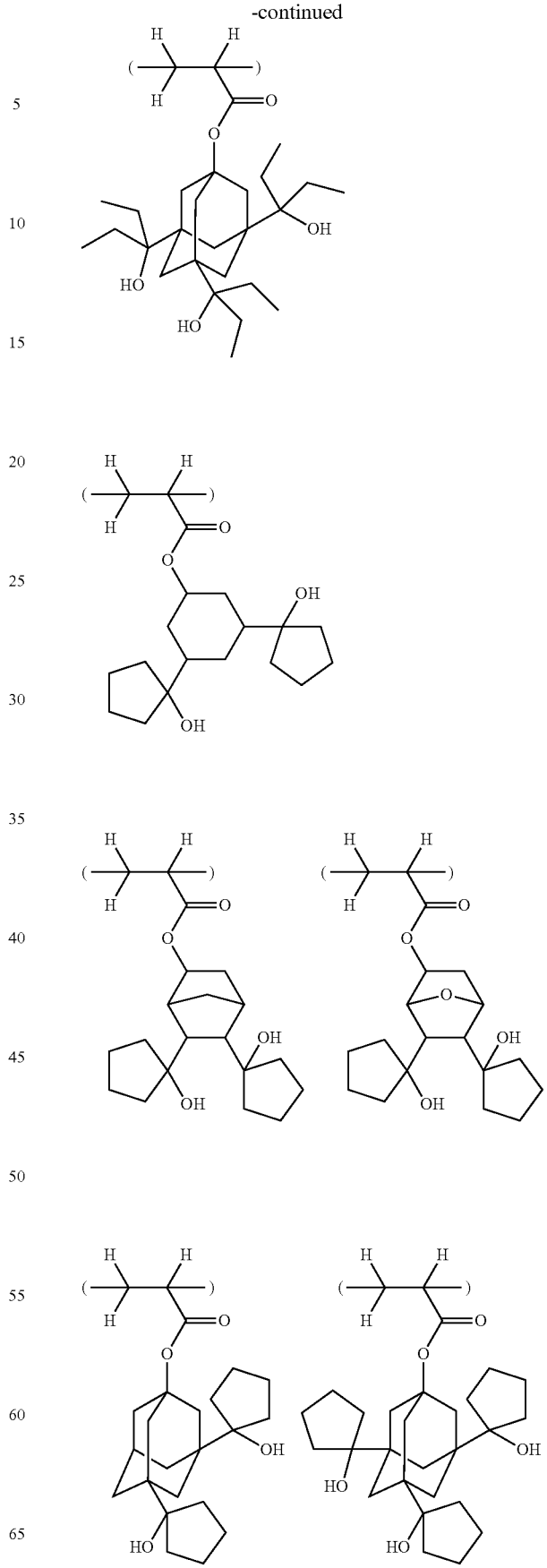

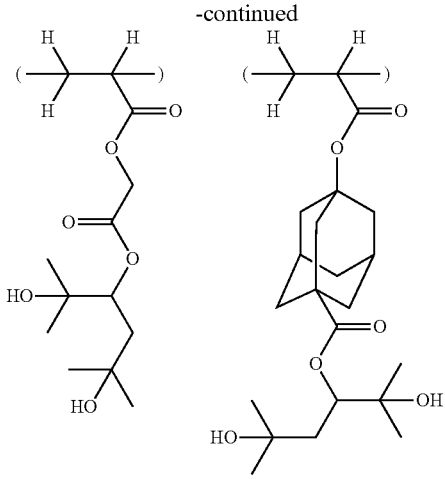
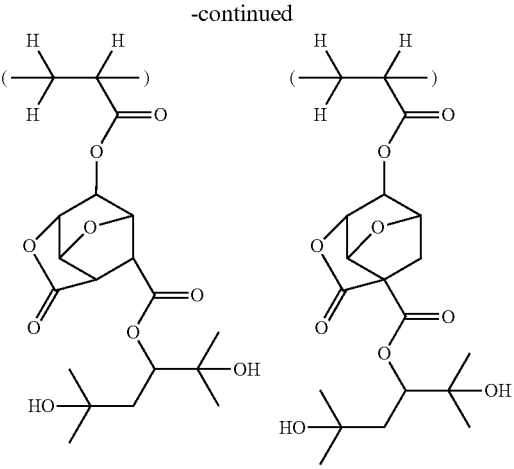
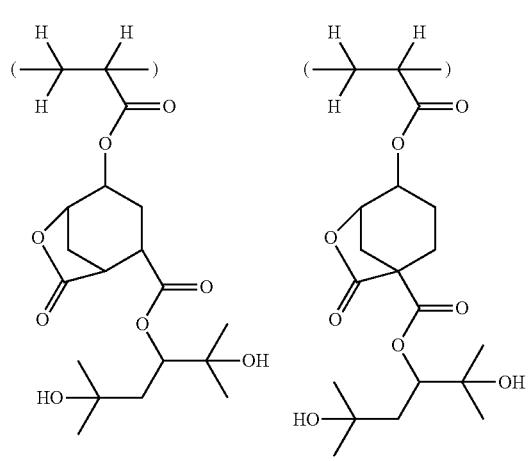
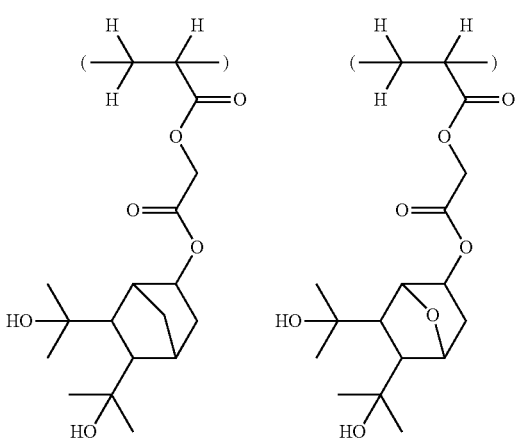
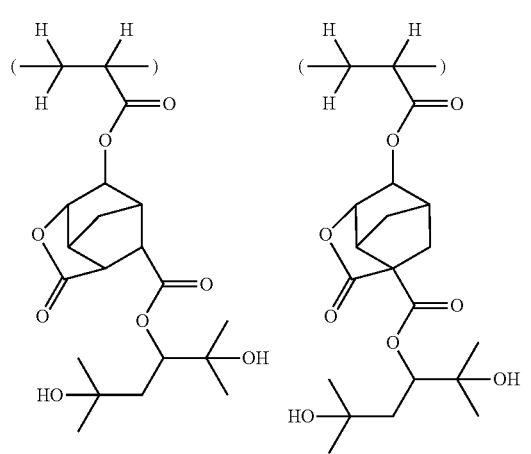
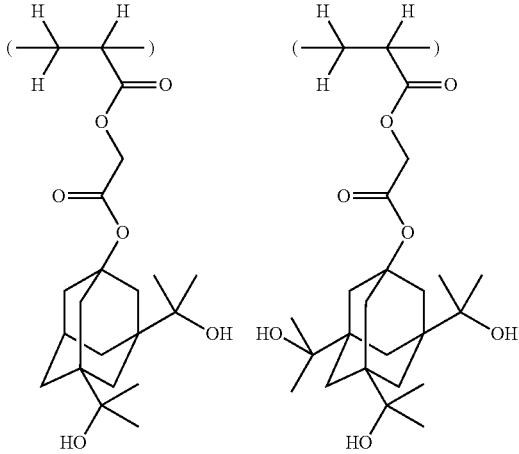

The monomer having formula (1) may be synthesized by reactions as shown in Scheme A although the synthesis route is not limited thereto.

Scheme A

Herein $R^1$ to $R^3$, $X^1$, $Z^1$, $k^1$ and $k^2$ are as defined above. $R^4$ is a straight, branched or cyclic $C_1$-$C_{10}$ monovalent hydrocarbon group. $X^3$ is a halogen atom, hydroxyl group or acyloxy group. M is Li, Na, K, MgX or ZnX wherein X is a halogen atom.

The first stage is addition reaction of a hydroxy-ester compound (4) with an organometallic reagent (5) to form a polyol compound (6).

The reaction may be performed by a standard procedure. For example, hydroxy-ester compound (4) is dissolved in an ether solvent such as tetrahydrofuran or diethyl ether, then organometallic reagent (5) corresponding to substituent groups $R^1$ and $R^3$, for example, a Grignard reagent such as methylmagnesium chloride or ethylmagnesium chloride or alkyl-lithium reagent such as methyllithium is added to the solution, whereby addition reaction takes place to form polyol compound (6) having tertiary alcohol. An appropriate amount of organometallic reagent (5) used is 3.0 to 10.0 moles, more preferably 3.0 to 5.0 moles per mole of the ester group of hydroxy-ester compound (4). Less than 3.0 moles of organometallic reagent (5) may be too small for the addition reaction to the ester group to take place to completion, because 1 mole of organometallic reagent (5) is consumed by the hydroxyl group of hydroxy-ester compound (4). More than 10.0 moles of organometallic reagent (5) may be disadvantageous in cost because of increased reactant expense. The reaction may be performed while cooling or heating if necessary, typically at a temperature of 0° C. to about the boiling point of the solvent. It is desirable from the standpoint of yield that the reaction time is determined so as to drive the reaction to completion by monitoring the reaction process by gas chromatography (GC) or silica gel thin-layer chromatography (TLC). Usually, the reaction time is about 0.5 to 24 hours. From the reaction mixture, the desired polyol compound (6) is recovered through an ordinary aqueous workup. If necessary, the compound may be purified by a standard technique such as distillation, chromatography or recrystallization.

The second stage is reaction of polyol compound (6) with an esterifying agent (7) to form monomer (1).

The reaction may be performed by a standard procedure. The preferred esterifying agent (7) is an acid chloride of formula (7) wherein $X^3$ is chlorine, a carboxylic acid of formula (7) wherein $X^3$ is hydroxyl, or an acid anhydride of formula (7) wherein $X^3$ is acyloxy. When an acid chloride is used as the esterifying agent, the reaction may be performed in a solventless system or in a solvent (e.g., methylene chloride, acetonitrile, toluene or hexane) by sequentially or simultaneously adding polyol compound (6), a corresponding acid chloride (e.g., methacryloyl chloride), and a base (e.g., triethylamine, pyridine or 4-dimethylaminopyridine), and optionally cooling or heating the reaction system. When a carboxylic acid is used as the esterifying agent, the reaction may be performed in a solvent (e.g., toluene or hexane) by heating polyol compound (6) and a corresponding carboxylic acid (e.g., methacrylic acid) in the presence of an acid catalyst, and optionally removing water formed by the reaction from the reaction system. Examples of the acid catalyst used herein include mineral acids such as hydrochloric acid, sulfuric acid, nitric acid and perchloric acid and organic acids such as p-toluenesulfonic acid and benzenesulfonic acid. When an acid anhydride is used as the esterifying agent, the reaction may be performed in a solventless system or in a solvent (e.g., methylene chloride, acetonitrile, toluene or hexane) by sequentially or simultaneously adding polyol compound (6), a corresponding acid anhydride (e.g., methacrylic anhydride), and a base (e.g., triethylamine, pyridine or 4-dimethylaminopyridine), and optionally cooling or heating the reaction system. It is desirable from the standpoint of yield that the reaction time is determined so as to drive the reaction to completion by monitoring the reaction process by GC or silica gel TLC. Usually, the reaction time is about 0.5 to 24 hours. From the reaction mixture, the desired monomer (1) is recovered through an ordinary aqueous workup. If necessary, the monomer may be purified by a standard technique such as distillation, chromatography or recrystallization.

The synthesis of the monomer having formula (2) is described by referring to one typical method for preparing monomer (2-1) corresponding to formula (2) wherein both $R^2$ and $R^3$ are methyl and $k^2=2$, which is shown below as Scheme B.

Scheme B

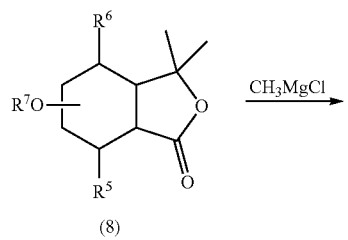

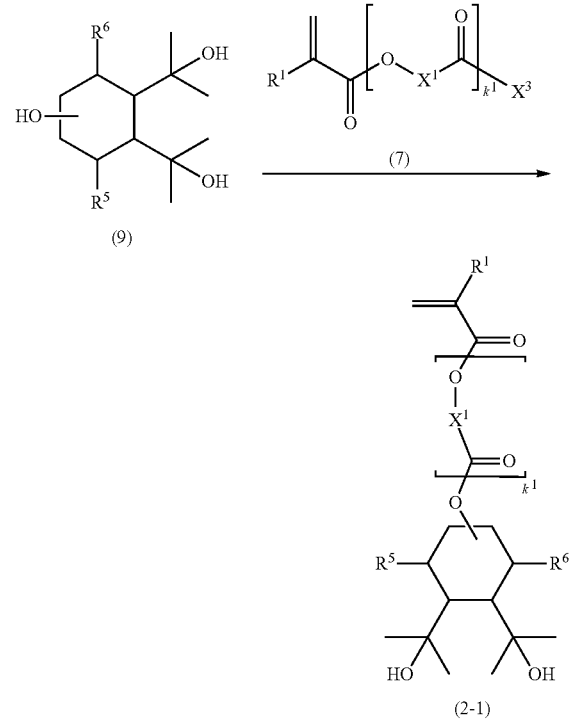

Herein $R^1$, $R^5$, $R^6$, $X^1$, $X^3$ and $k^1$ are as defined above. $R^7$ is hydrogen or acyl.

The first stage is reaction of a lactone compound (8) with a Grignard reagent to form a triol compound (9). Specifically, lactone compound (8) is dissolved in an ether solvent (e.g., tetrahydrofuran or diethyl ether), and then methylmagnesium chloride is added to the solution whereby reaction takes place to form triol compound (9) having tertiary alcohol. An appropriate amount of methylmagnesium chloride used is 3.0 to 10.0 moles, more preferably 3.0 to 5.0 moles per mole of lactone compound (8). Less than 3.0 moles of methylmagnesium chloride may be too small for the addition reaction to the lactone to take place to completion, because 1 to 2 moles of methylmagnesium chloride is consumed by the substituent group —$OR^7$ of lactone compound (8). More than 10.0 moles of methylmagnesium chloride may be disadvantageous in cost because of increased reactant expense. The reaction may be performed while cooling or heating if necessary, typically at a temperature of 0° C. to about the boiling point of the solvent. It is desirable from the standpoint of yield that the reaction time is determined so as to drive the reaction to completion by monitoring the reaction process by GC or silica gel TLC. Usually, the reaction time is about 0.5 to 24 hours. From the reaction mixture, the desired triol compound (9) is recovered through an ordinary aqueous workup. If necessary, the compound may be purified by a standard technique such as distillation, chromatography or recrystallization.

The second stage is reaction of triol compound (9) with esterifying agent (7) to form monomer (2-1). The reaction conditions are the same as the above-described reaction of polyol compound (6) with esterifying agent (7).

Polymer

The invention also provides a polymer comprising recurring units having the formula (3), the recurring units being derived from the monomer having formula (1).

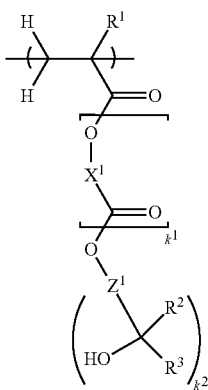

(3)

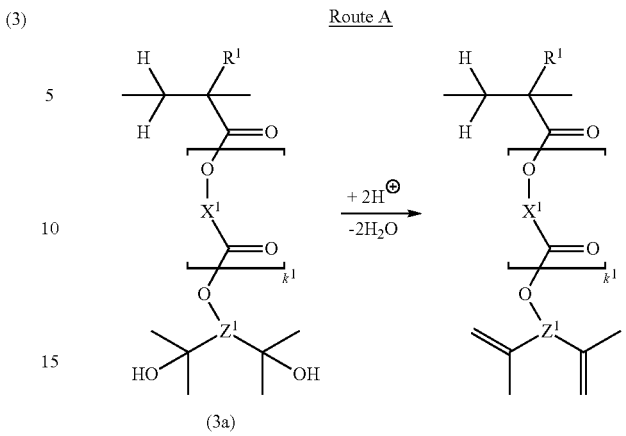

Route A (3a)

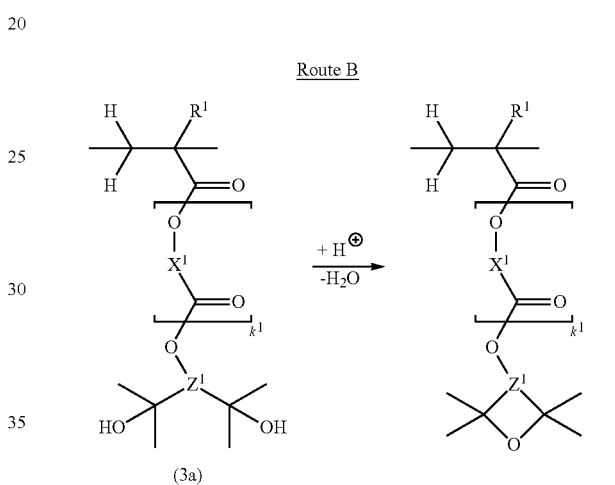

Route B (3a)

Herein $R^1$, $R^2$, $R^3$, $X^1$, $Z^1$, $k^1$ and $k^2$ are as defined above.

Differently stated, the inventive polymer is a (meth) acrylate polymer having a plurality of tertiary alcoholic hydroxyl groups as the acid labile group. In the scheme shown below, reference is made to a polymer (3a) wherein both $R^2$ and $R^3$ are methyl and $k^2=2$, as one typical example. When the inventive polymer is used as a base resin in a resist composition, water molecule(s) is eliminated (referred to as "dehydration", hereinafter) under the action of strong acid generated in the exposed region of resist film, whereby the structure of recurring unit changes. Although the situation varies with the structure of $Z^1$, it is believed that either formation of a plurality of olefin moieties by dehydration (Route A) or reaction to form a ring such as oxetane or tetrahydrofuran ring by intramolecular cyclization as a result of dehydration (Route B) may take place. Prior to exposure, the polymer has a high affinity to and high solubility in alkaline developer by virtue of a plurality of highly polar, hydrophilic groups thereon. After exposure, a plurality of hydroxyl groups are lost in the exposed region of resist film, indicating a substantial drop of solubility in alkaline developer, that is, the exposed region becoming insolubilized in the developer. In addition, since only water molecule is lost after polarity switch, a change of carbon density is extremely small. Particularly when the polymer has a cyclic hydrocarbon group in its structure, only a polarity switch occurs while maintaining the robust alicyclic structure. That is, since the inventive polymer shows a very high dissolution contrast relative to alkaline developer, it serves as a base resin component which does not necessarily need insolubilization by a crosslinker. Since the polymer maintains a high carbon density and resin film thickness even after the polarity switch, it is less susceptible to bridging between pattern features and pattern collapse due to swell, which are considered problematic with negative resist materials of conventional polarity switch type and negative resist materials of crosslinking reaction type. In addition, the polymer has improved etch resistance. Consequently a finer size pattern can be resolved.

Herein $R^1$, $X^1$, $Z^1$ and $k^1$ are as defined above.

As alluded to previously, the inventive polymer has a high polarity prior to dehydration reaction, but a low polarity after dehydration, and thus exhibits a high dissolution contrast with respect to alkaline aqueous solution. For the reason that polymers of formula (3) wherein substituent groups $R^2$ and $R^3$ in the tertiary alcohol moiety contain a smaller number of carbon atoms have a higher polarity and hydrophilicity, and such substituent groups are more readily introduced during preparation of the monomer (1), it is preferred that $R^2$ and $R^3$ be independently methyl or ethyl. From the aspect of maintaining the carbon density and robustness before and after dehydration reaction, it is preferred that $Z^1$ be a $C_3$-$C_{20}$ cyclic hydrocarbon group. It is more preferred that $Z^1$ be a $C_3$-$C_{20}$ alicyclic group and $k^2=2$ because starting reactants from which the monomer (1) is prepared are readily available. A value of $k^2$ in excess of 4 is undesirable despite a greater polarity switch before and after dehydration reaction, because the solubility of a monomer (1) in the polymerization solvent is substantially reduced, the starting reactants are scarcely available, and a polymer becomes low in solvent solubility which is necessary for formulating resist compositions.

In addition to recurring units derived from the monomer of formula (1), the inventive polymer may further comprise recurring units of at least one type selected from recurring units having formulae (A) to (D) for the purpose of solubility control.

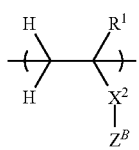 (A)

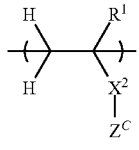 (B)

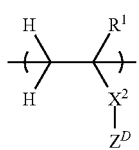 (C)

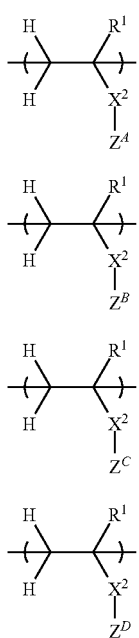 (D)

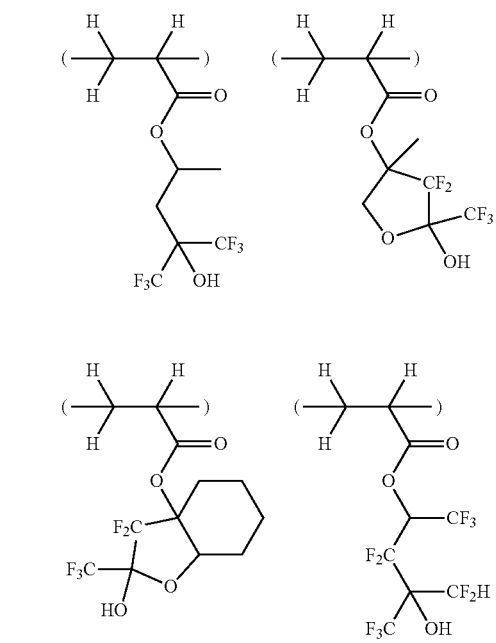

Herein $R^1$ is as defined above. $Z^A$ is a $C_1$-$C_{20}$ fluoroalcohol-containing group. $Z^B$ is a $C_1$-$C_{20}$ phenolic hydroxyl-containing group. $Z^C$ is a $C_1$-$C_{20}$ carboxyl-containing group. $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety. $X^2$ is a single bond, methylene, ethylene, phenylene, fluorinated phenylene, naphthylene, —O—$R^{01}$—, or —C(=O)—$Z^2$—$R^{01}$—, wherein $Z^2$ is oxygen or NH, and $R^{01}$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

The recurring unit of formula (A) has a fluoroalcohol-containing group having high affinity to alkaline aqueous solution. Preferred examples of the fluoroalcohol-containing unit include recurring units having a 1,1,1,3,3,3-hexafluoro-2-propanol residue and 2-hydroxy-2-trifluoromethyloxolane structure, as described in JP-A 2007-297590, JP-A 2008-111103, JP-A 2008-122932, and JP-A 2012-128067. Although these units have a tertiary alcoholic hydroxyl group or hemiacetal structure, they are not reactive with acid because of fluorine substitution.

Since the recurring units of formulae (A) to (C) are structural units having hydroxyl group's proton with a high acidity, the polymer becomes higher in alkaline solubility as the proportion of these units incorporated is increased. On the other hand, excessive incorporation of these units can adversely affect a polarity switch (or alkali insolubilizing effect) that is brought about by dehydration reaction taking place in recurring unit of formula (3) by acid. Accordingly, the recurring units of formulae (A) to (C) are preferably incorporated in such proportions that the alkali solubility of the unexposed region may be supplemented and the alkali insolubilizing effect of the exposed region not be impaired.

Illustrative, non-limiting examples of the recurring unit having formula (A) are shown below.

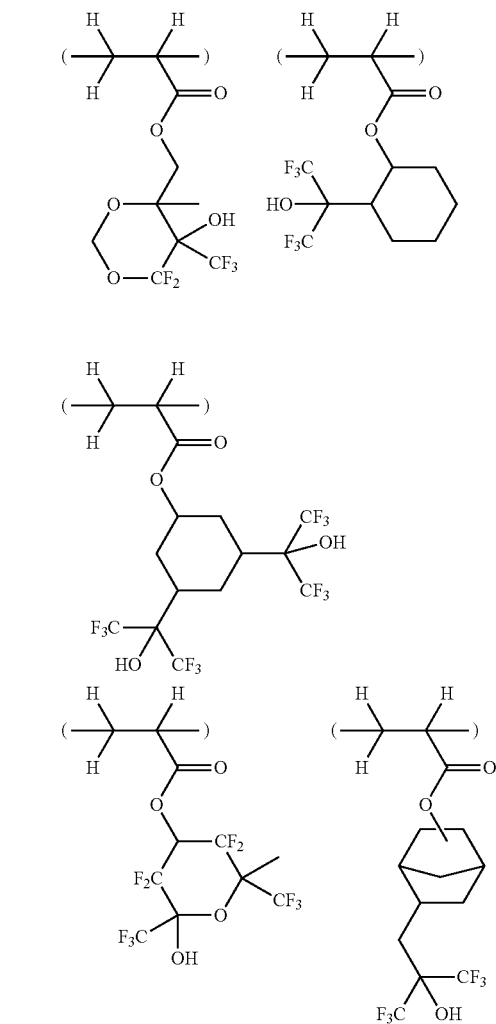

-continued
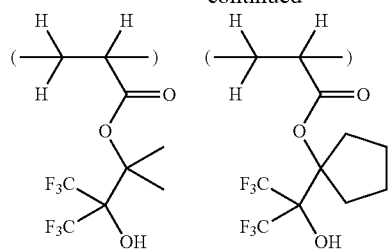
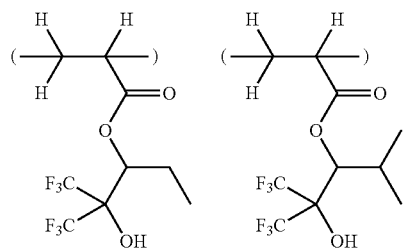
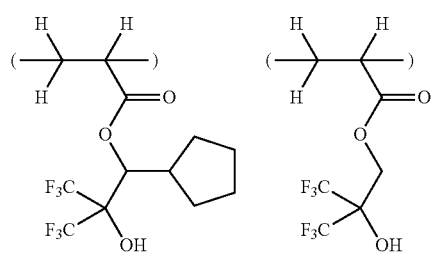
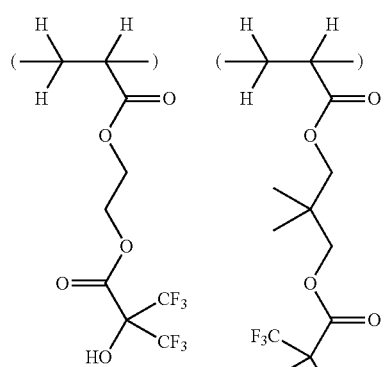
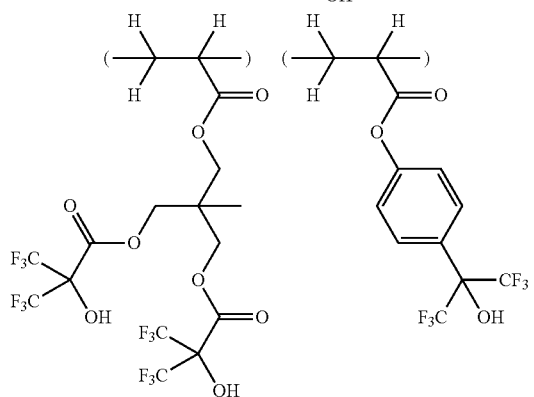
-continued
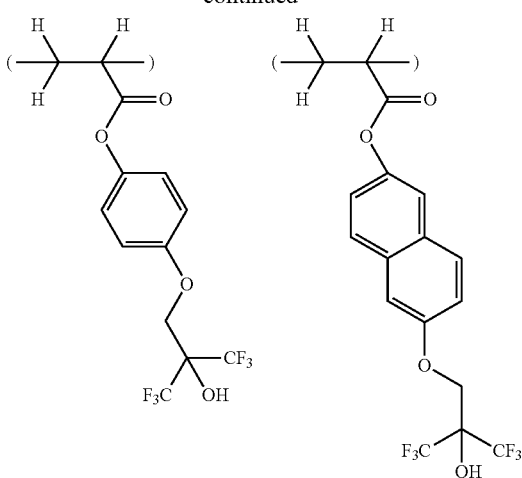
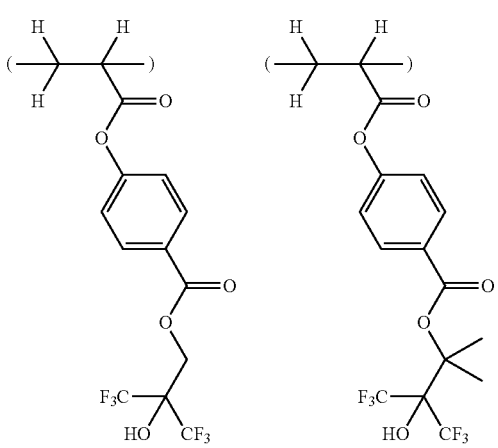
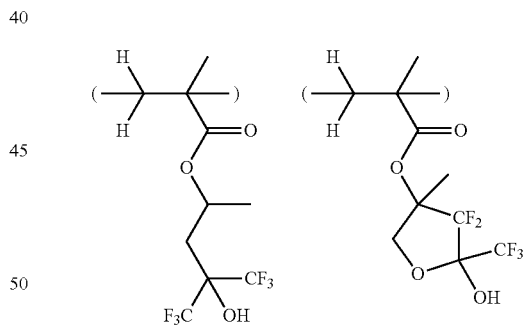
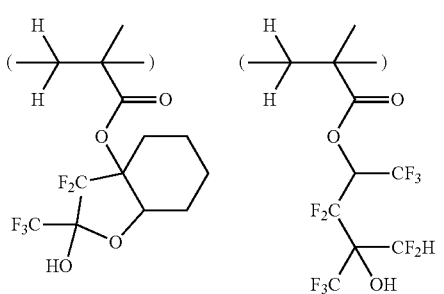

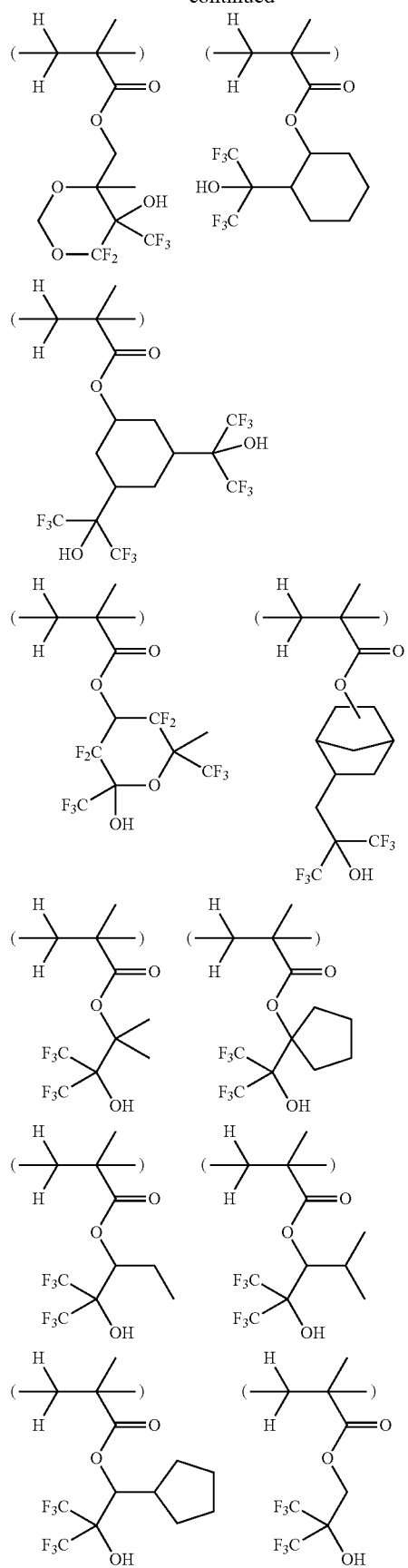
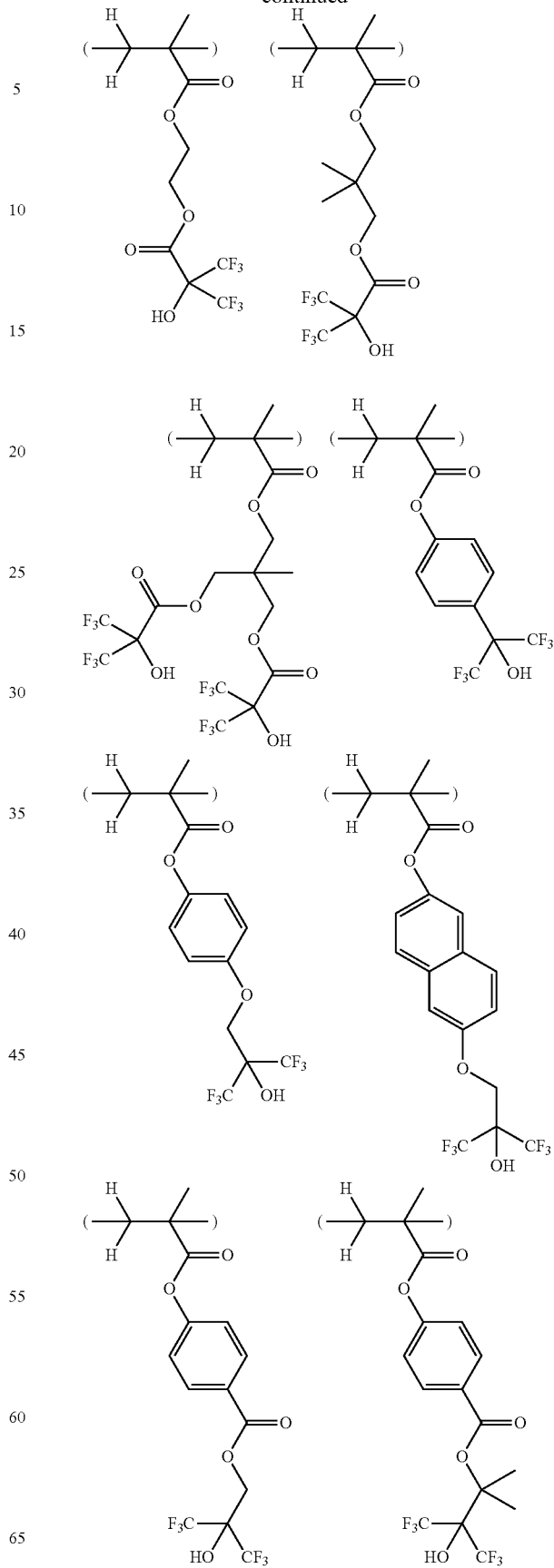

-continued
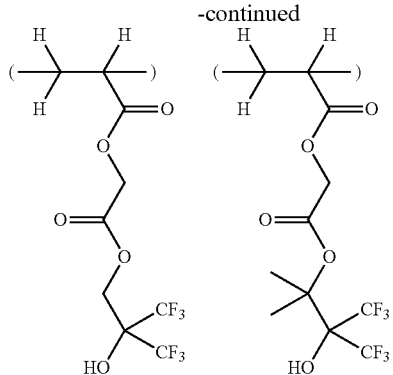
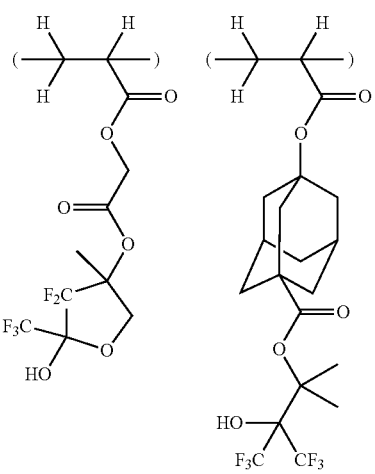
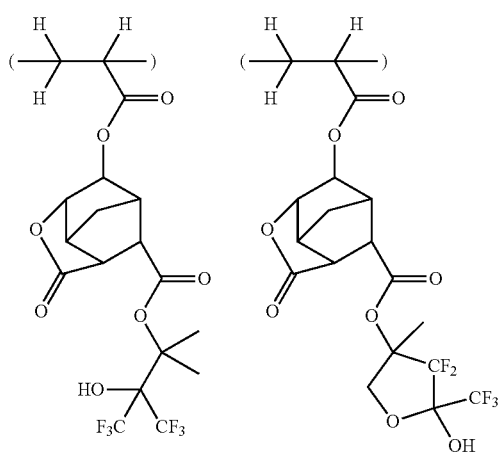
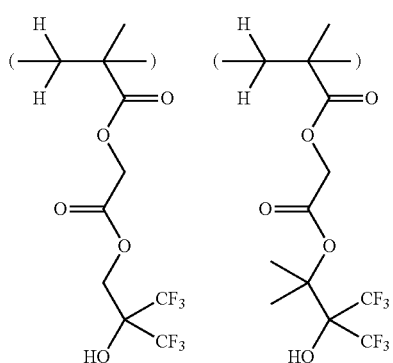
-continued
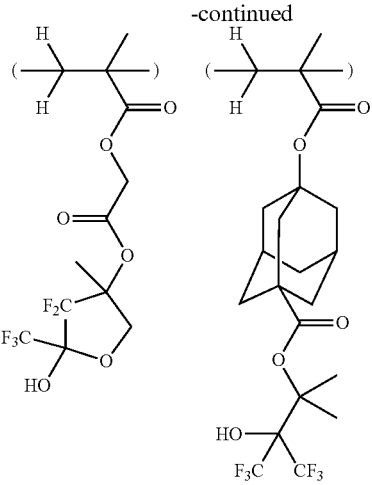
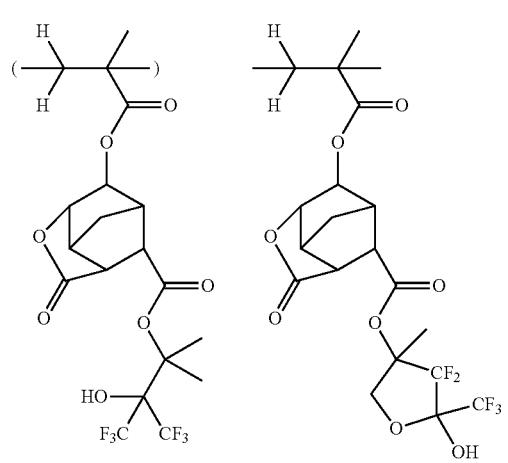
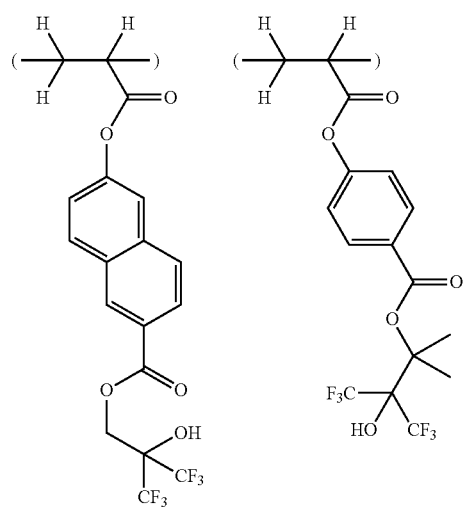

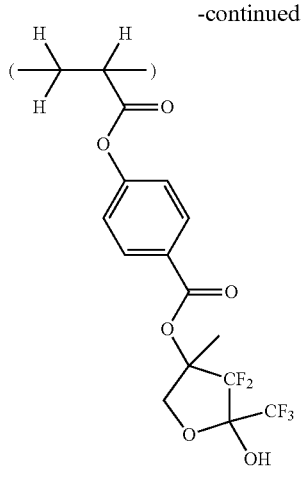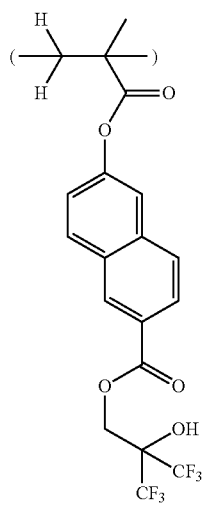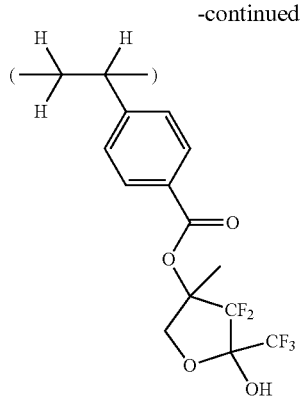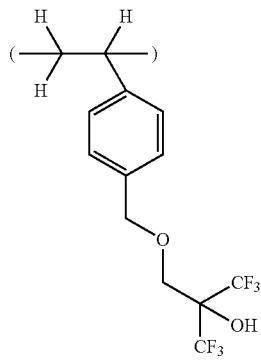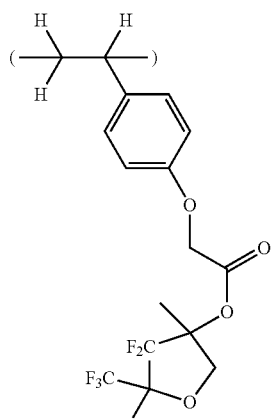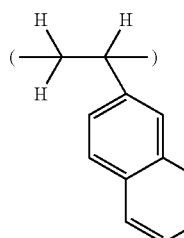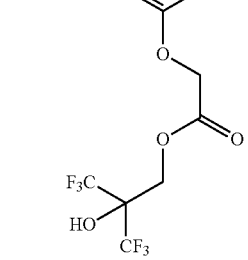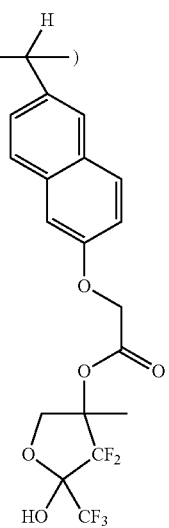

Illustrative, non-limiting examples of the recurring unit having formula (B) are shown below.
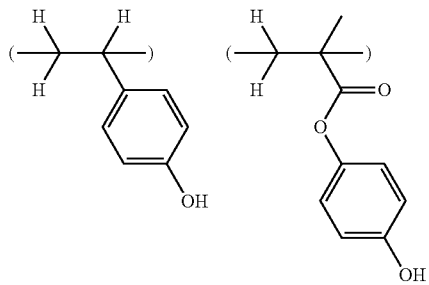
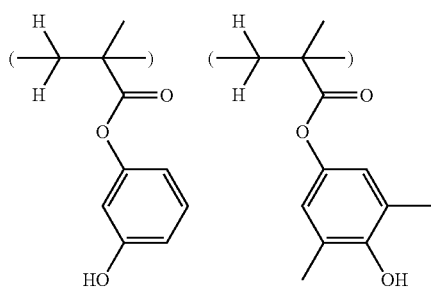
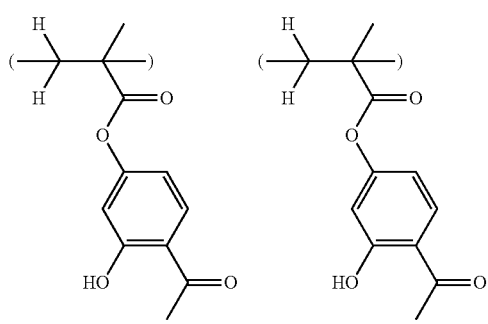
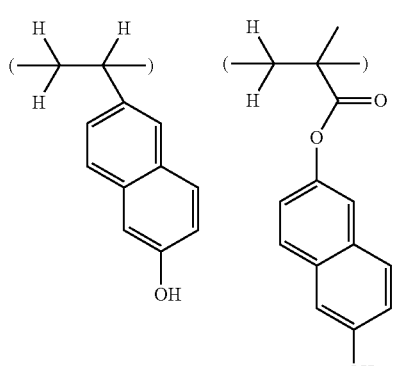
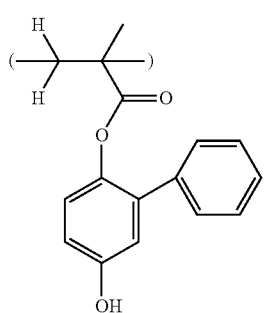
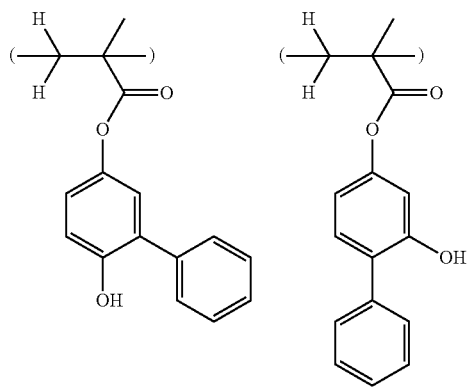
Illustrative, non-limiting examples of the recurring unit having formula (C) are shown below.
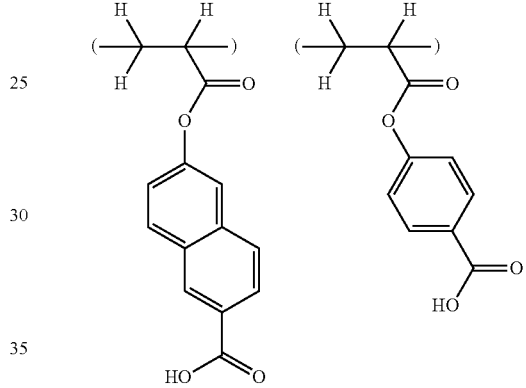
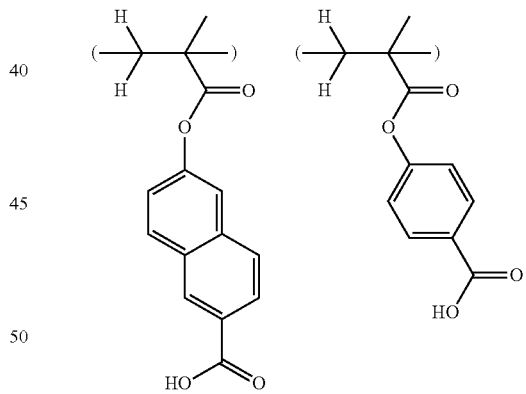
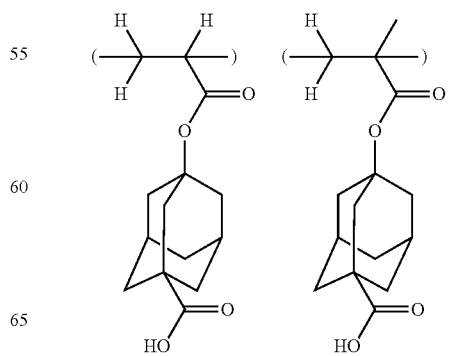

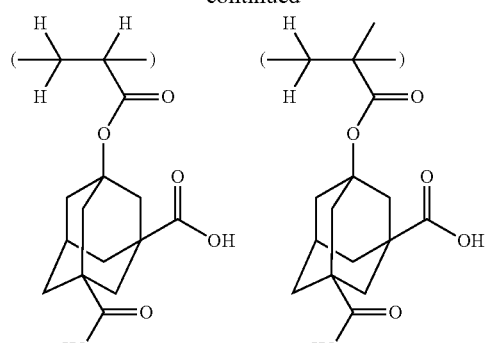
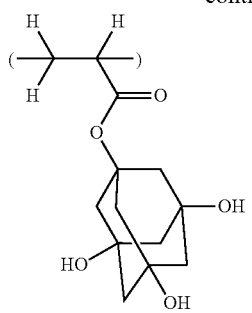
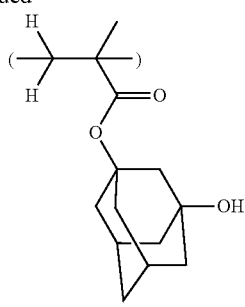

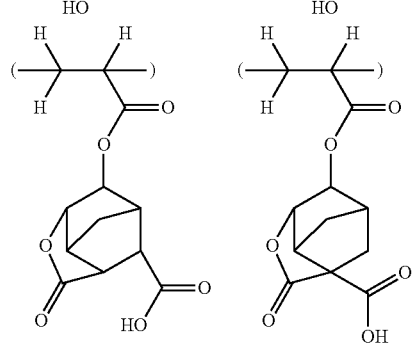
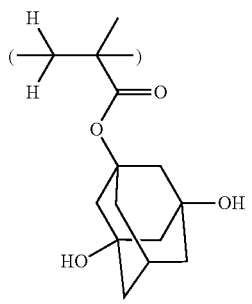
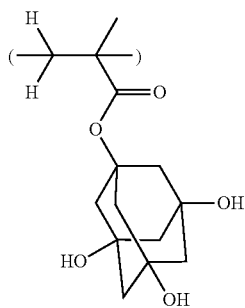

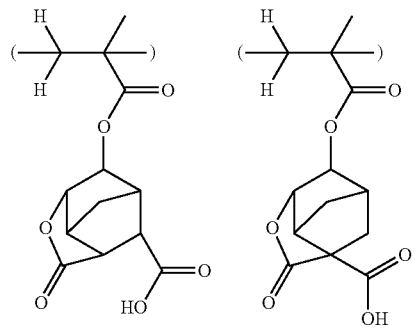
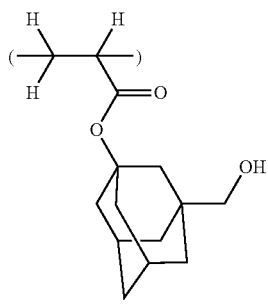

It is possible that the fluoroalcohol is protected with an acyl group or acid labile group in the polymer, so that the fluoroalcohol-containing unit corresponding to formula (A) may be generated by hydrolysis in alkaline developer or deprotection with the acid generated after exposure. Suitable such recurring units include the units described in JP-A 2012-128067 (U.S. Pat. No. 8,916,331), specifically units in paragraphs [0036]-[0040] and units (2a), (2b) and (2f) in paragraph [0041].

Illustrative, non-limiting examples of the recurring unit having formula (D) are shown below.

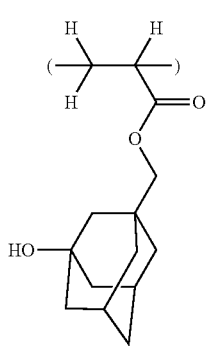
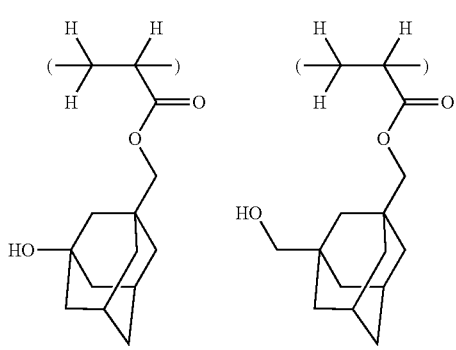

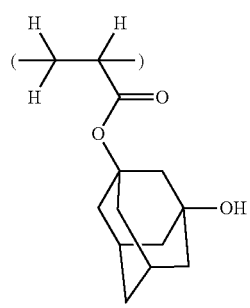
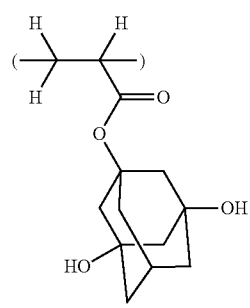
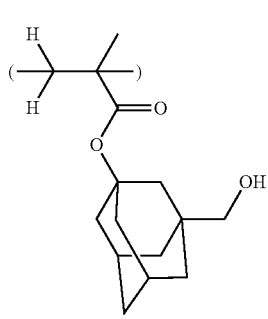

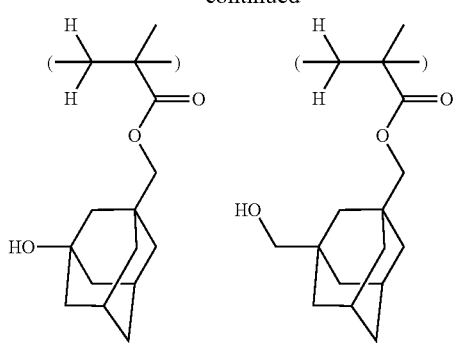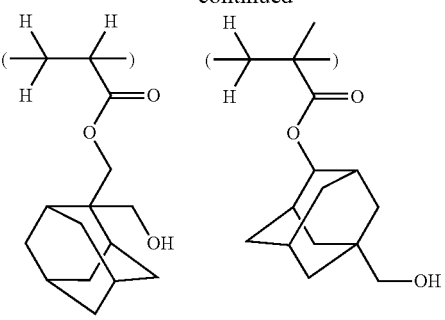

-continued
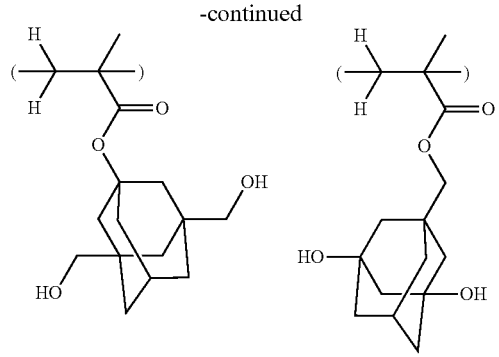
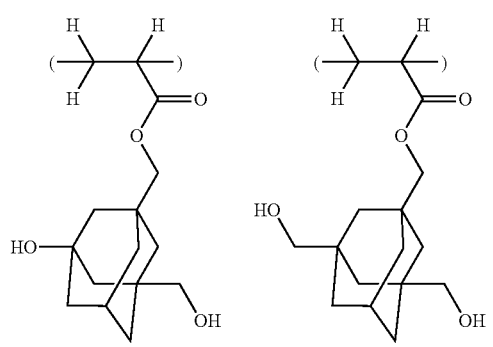
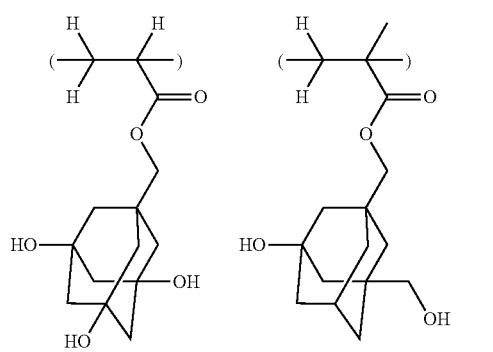
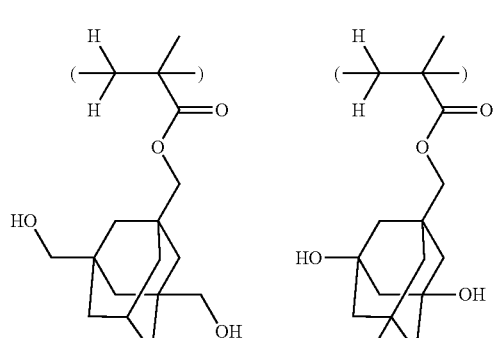
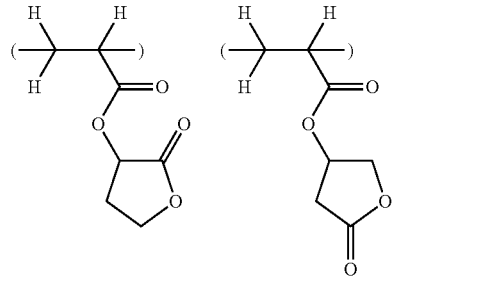
-continued
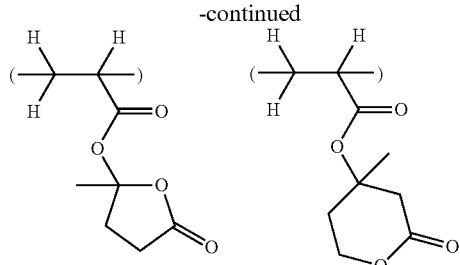
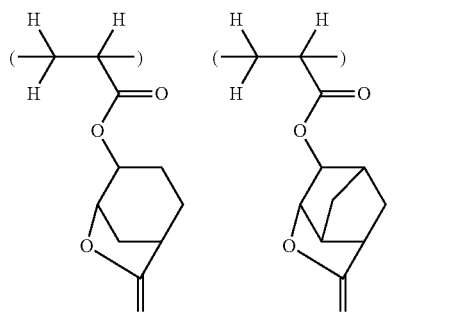
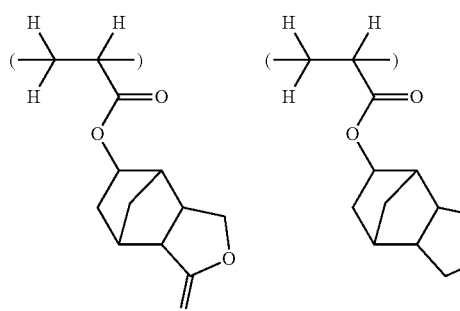
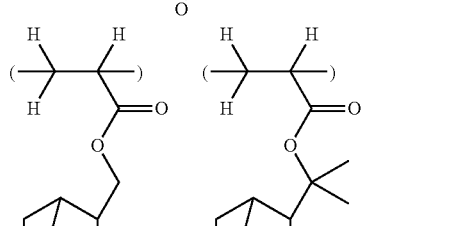
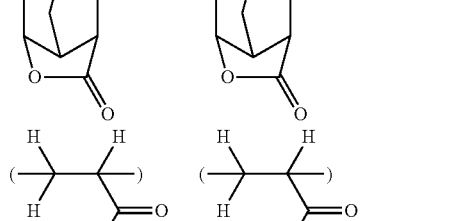
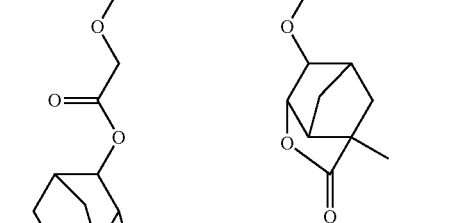

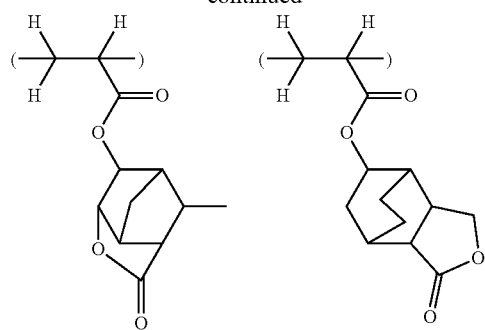
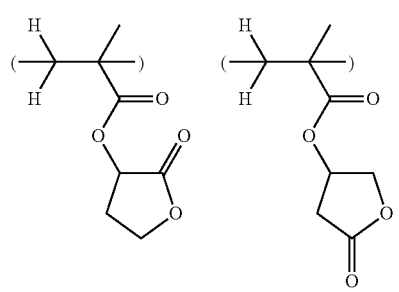
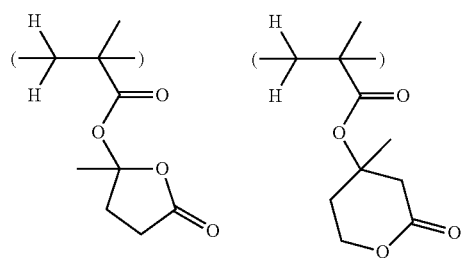
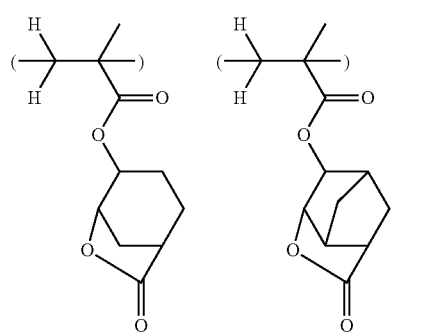
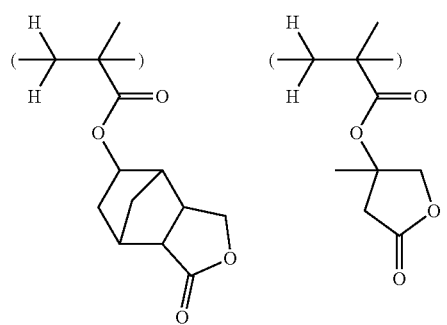
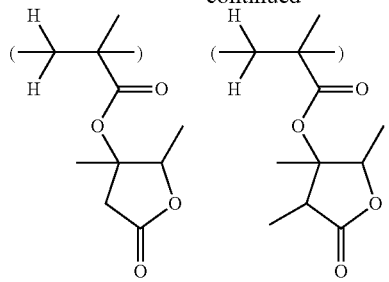
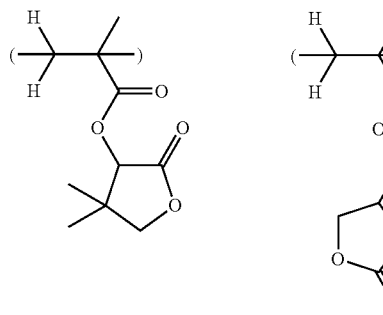
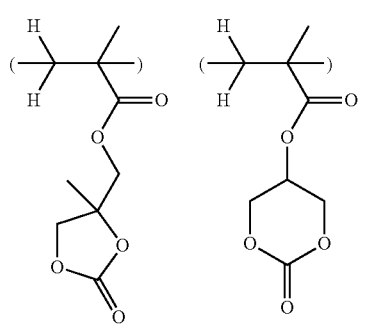
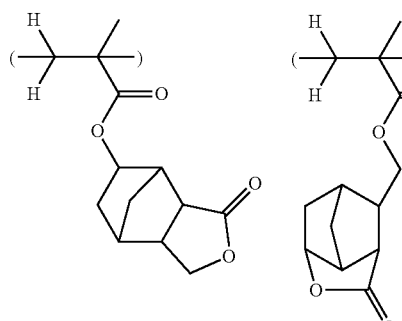
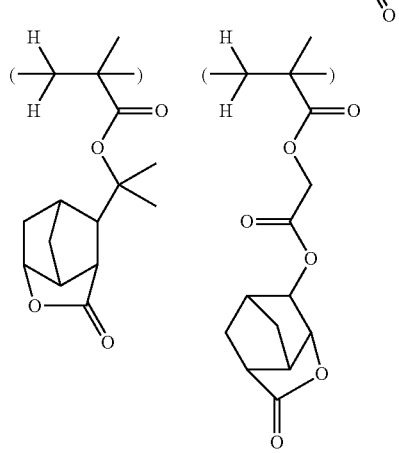

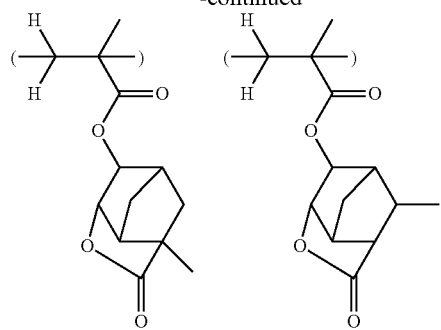
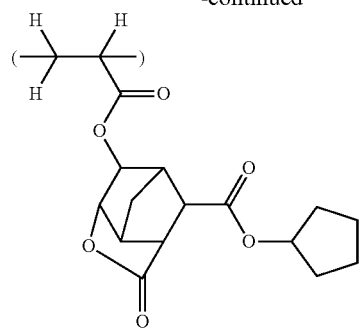
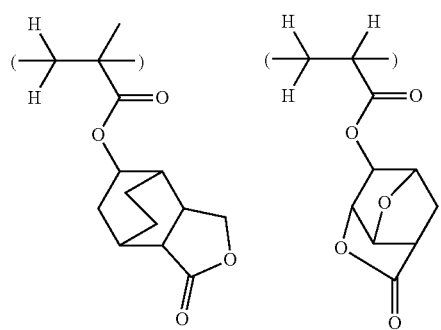
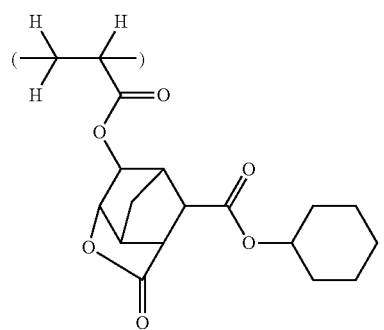
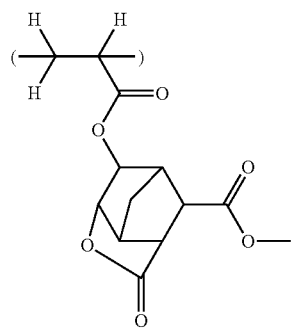
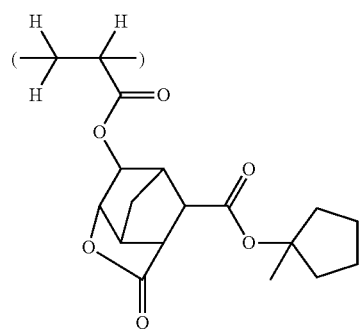
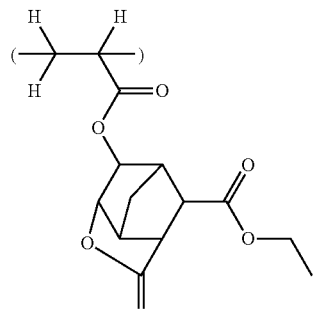
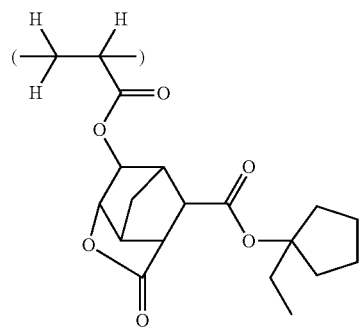
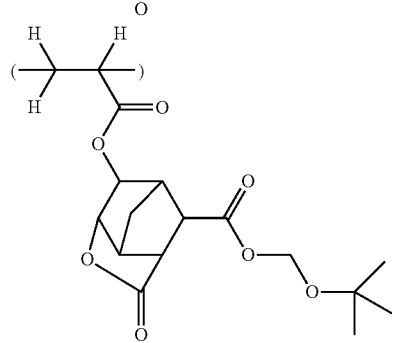
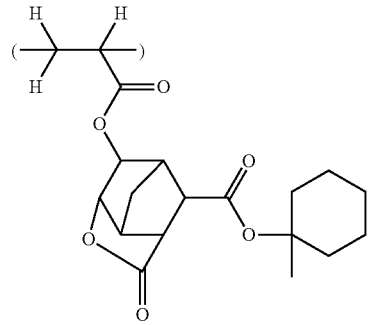

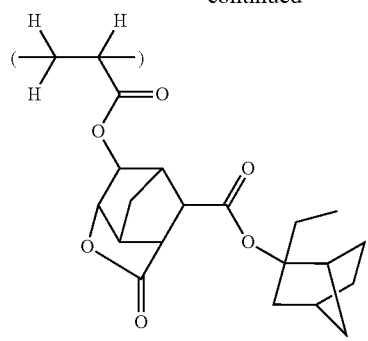
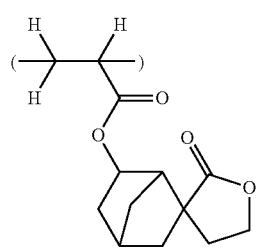
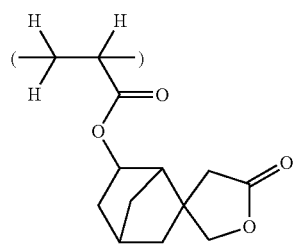
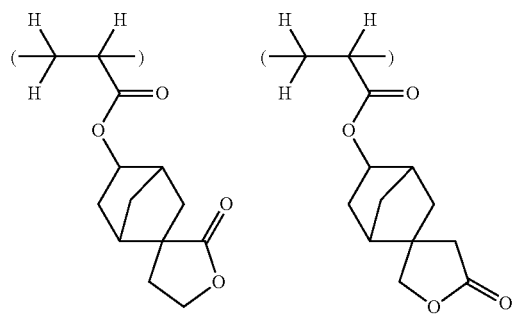
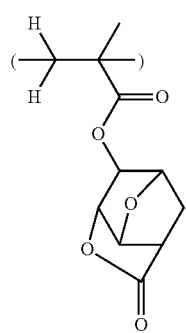
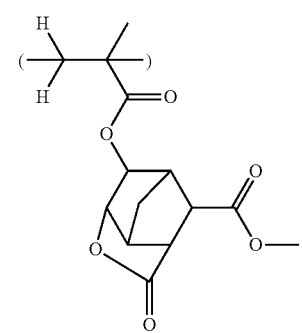
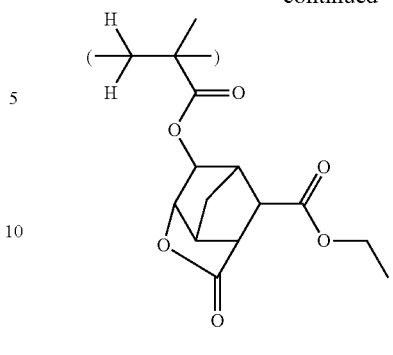
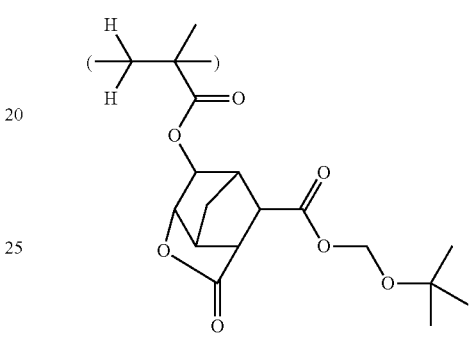
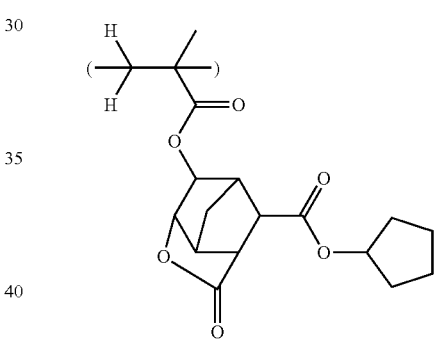
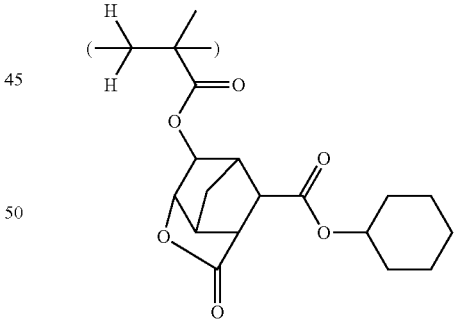
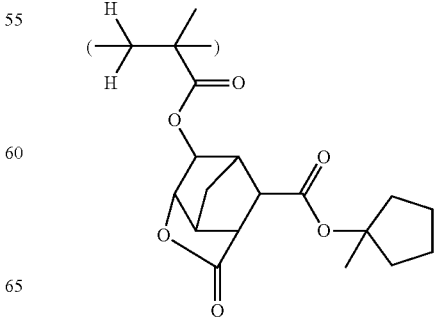

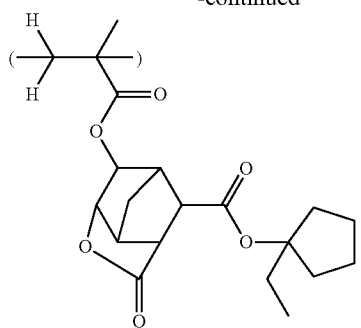
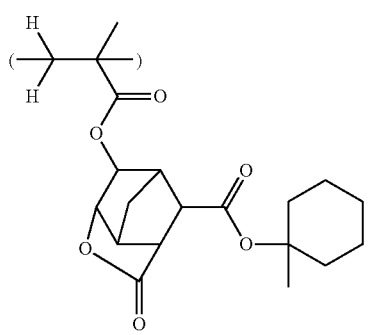
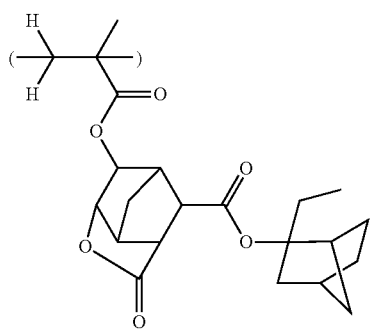
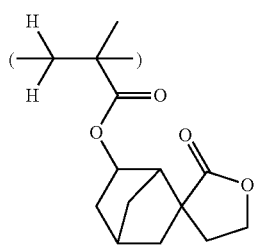
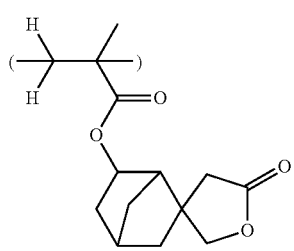
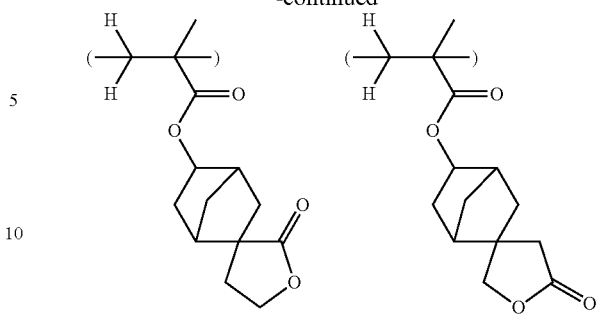
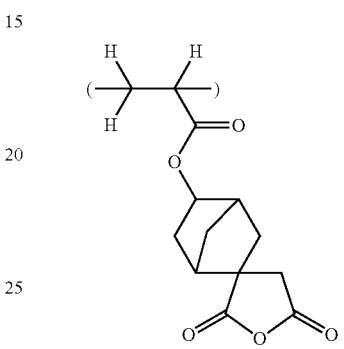
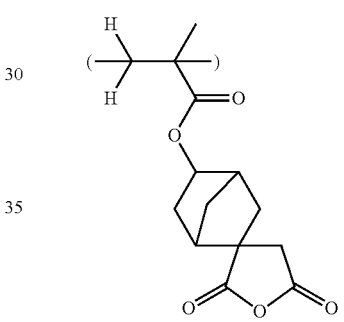
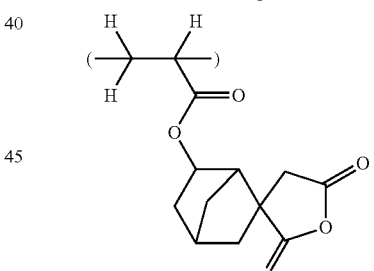
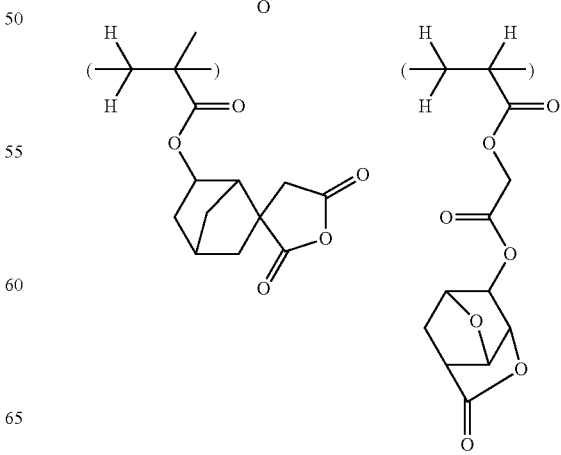

-continued
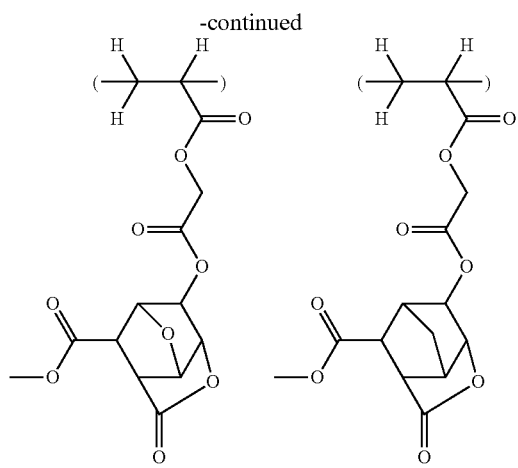
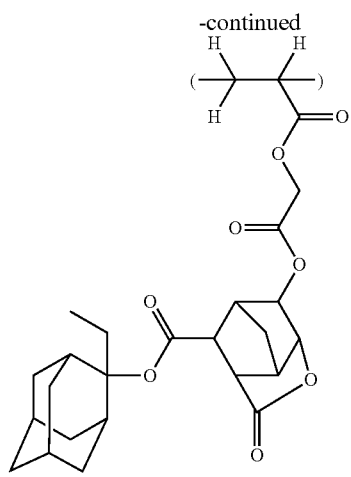
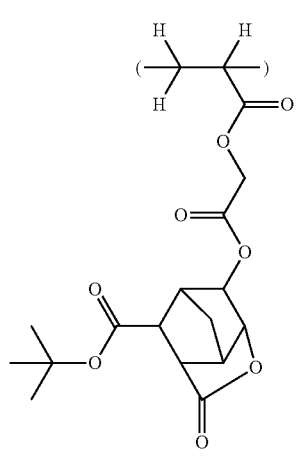
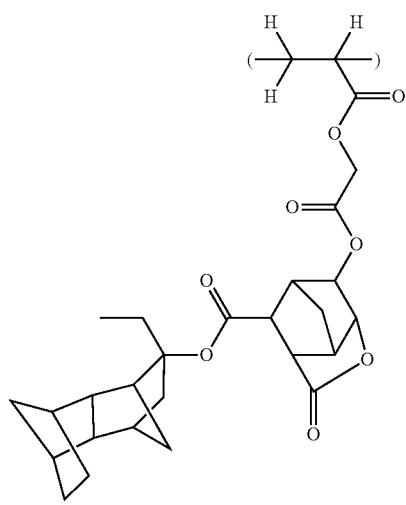
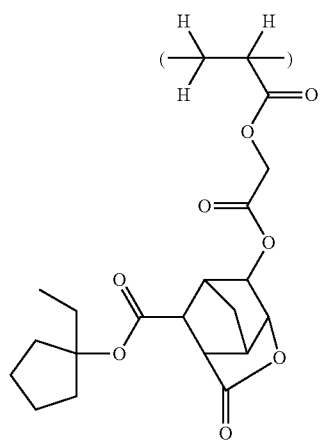
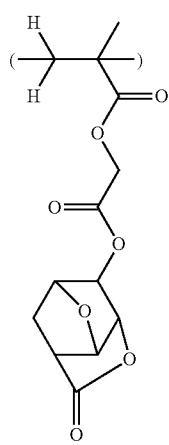
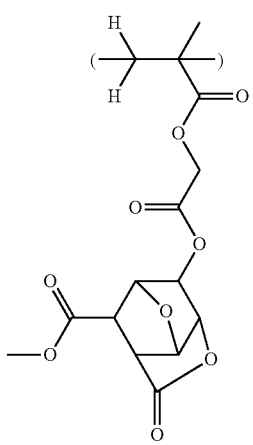

49
-continued
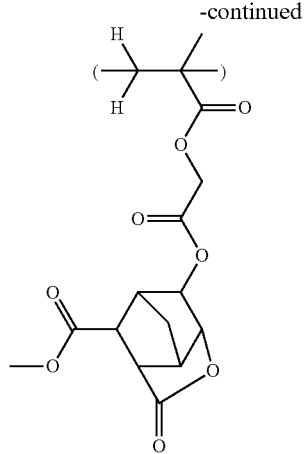
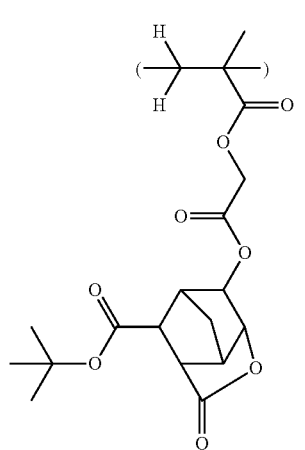
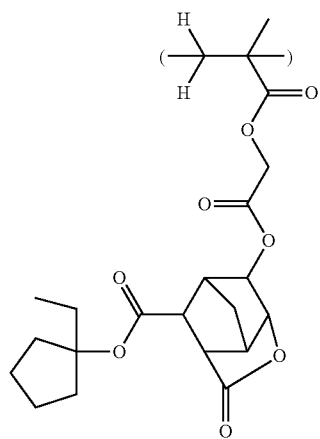
50
-continued
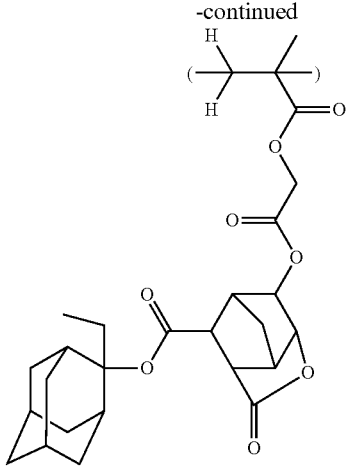
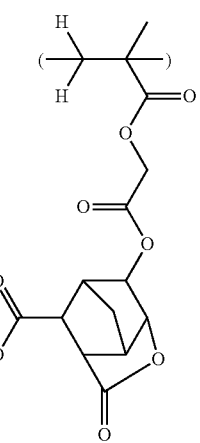
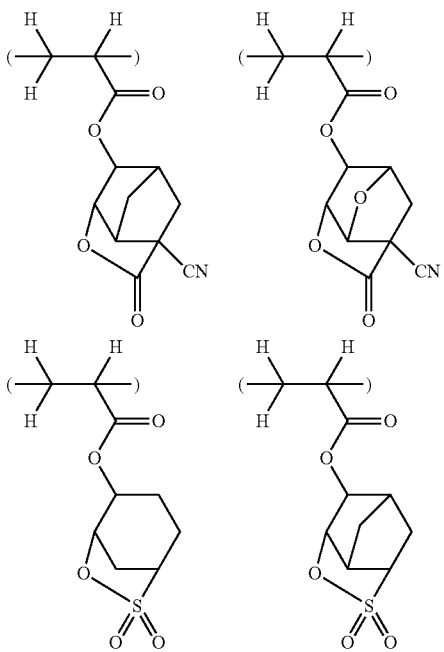

51
-continued
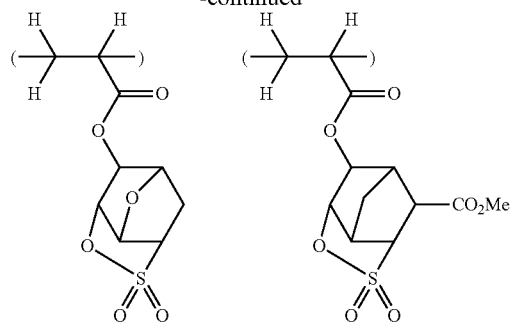
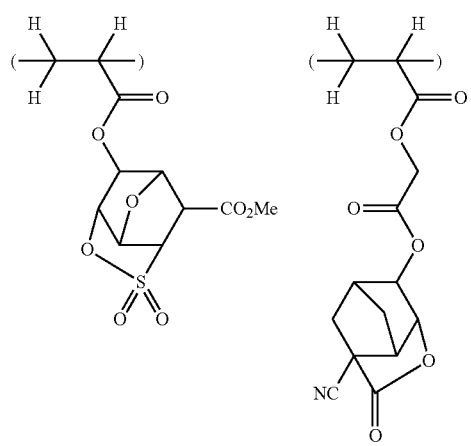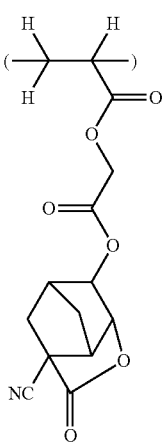
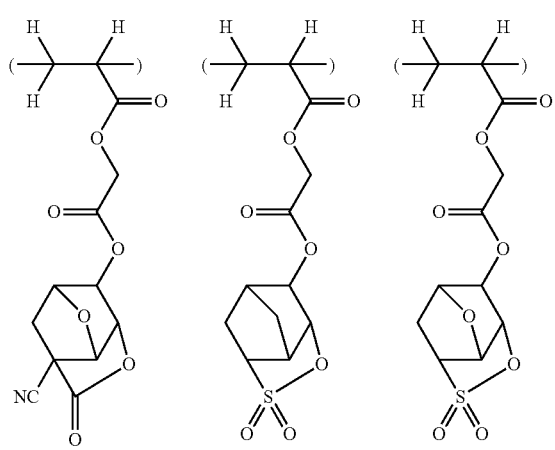
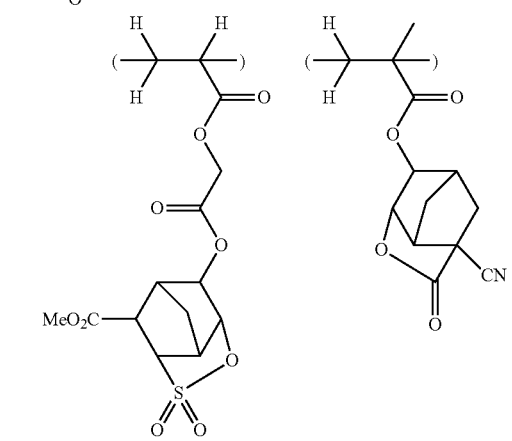
52
-continued
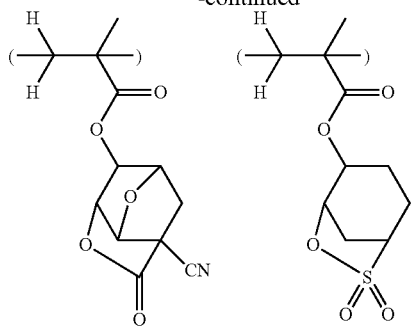
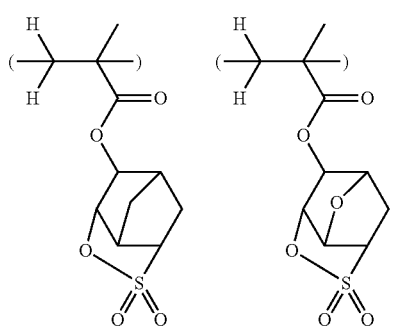
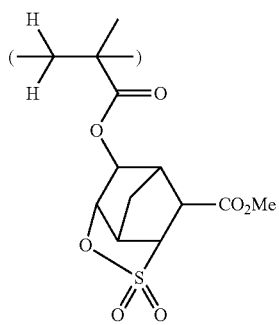
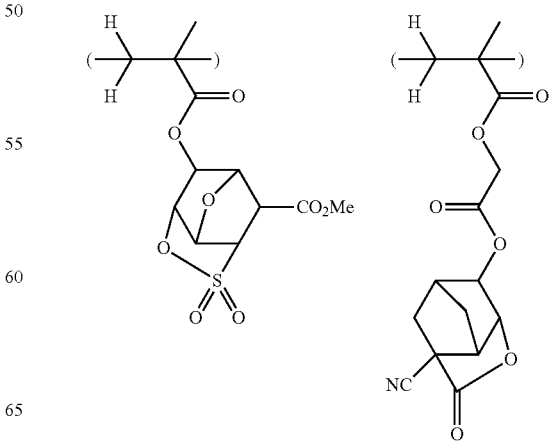

53
-continued
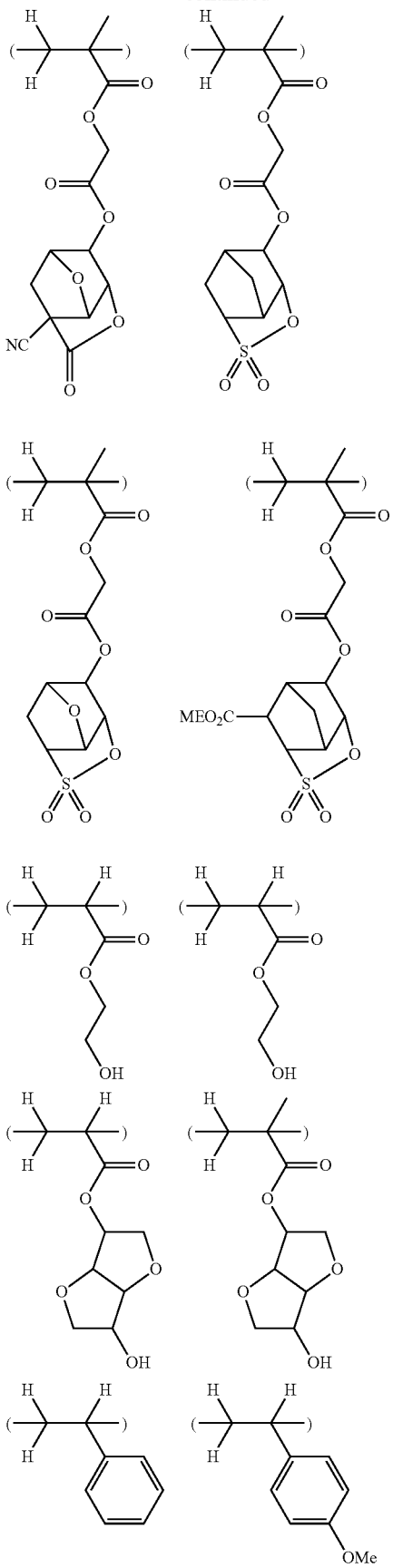
54
-continued
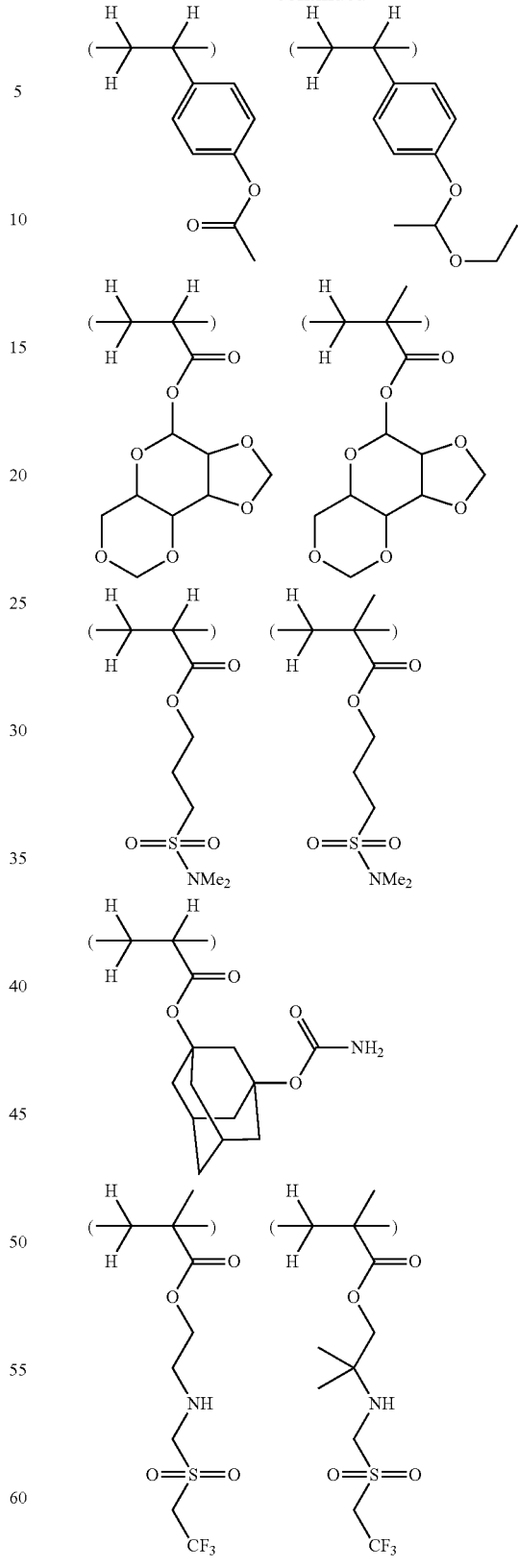
In addition to the foregoing units, the inventive polymer may further comprise recurring units of at least one type selected from recurring units having formulae (f1) to (f3).

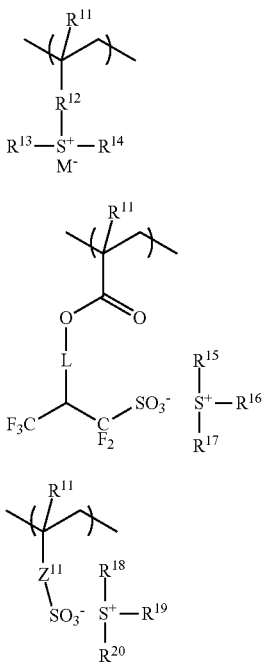

Herein $R^{11}$ is each independently hydrogen or methyl. $R^{12}$ is a single bond, phenylene, —O—$R^{21}$—, or —C(=O)—$Z^{22}$—$R^{21}$— wherein $Z^{22}$ is oxygen or NH and $R^{21}$ is a straight, branched or cyclic $C_1$-$C_6$ alkylene group, straight, branched or cyclic $C_2$-$C_6$ alkenylene group or phenylene group, which may contain a carbonyl (—CO—), ester (—COO—), ether (—O—) or hydroxyl moiety. L is a single bond or —$Z^{33}$—C(=O)—O— wherein $Z^{33}$ is a straight, branched or cyclic $C_1$-$C_{20}$ divalent hydrocarbon group which may be substituted with a heteroatom. $Z^{11}$ is a single bond, methylene, ethylene, phenylene, fluorinated phenylene, —O—$R^{22}$—, or —C(=O)—$Z^{44}$—$R^{22}$— wherein $Z^{44}$ is oxygen or NH and $R^{22}$ is a straight, branched or cyclic $C_1$-$C_6$ alkylene group, straight, branched or cyclic $C_2$-$C_6$ alkenylene group or phenylene group, which may contain a carbonyl, ester, ether or hydroxyl moiety. $M^-$ is a non-nucleophilic counter ion.

$R^{13}$ to $R^{20}$ are each independently a straight, branched or cyclic $C_1$-$C_{20}$ monovalent hydrocarbon group which may be substituted with or separated by a heteroatom. Suitable monovalent hydrocarbon groups include alkyl groups such as methyl, ethyl, n-propyl, isopropyl, n-butyl, t-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl, and thienyl; and aralkyl groups such as benzyl, 1-phenylethyl, and 2-phenylethyl, with the aryl groups being preferred. Also included are modified forms of the foregoing groups in which at least one hydrogen atom is replaced by a heteroatom such as oxygen, sulfur, nitrogen or halogen, or in which a heteroatom such as oxygen, sulfur or nitrogen intervenes, and as a result, a hydroxyl group, cyano group, carbonyl group, ether bond, ester bond, sulfonic acid ester bond, carbonate bond, lactone ring, sultone ring, carboxylic acid anhydride, or haloalkyl group forms or intervenes. Also, a pair of $R^{13}$ and $R^{14}$ may bond together to form a ring with the sulfur atom to which they are attached, and any two or more of $R^{15}$, $R^{16}$ and $R^{17}$, or any two or more of $R^{18}$, $R^{19}$ and $R^{20}$ may bond together to form a ring with the sulfur atom to which they are attached.

When L is —$Z^{33}$—C(=O)—O—, examples of the optionally heteroatom-substituted, straight, branched or cyclic $C_1$-$C_{20}$ divalent hydrocarbon group represented by $Z^{33}$ are shown below, but not limited thereto.

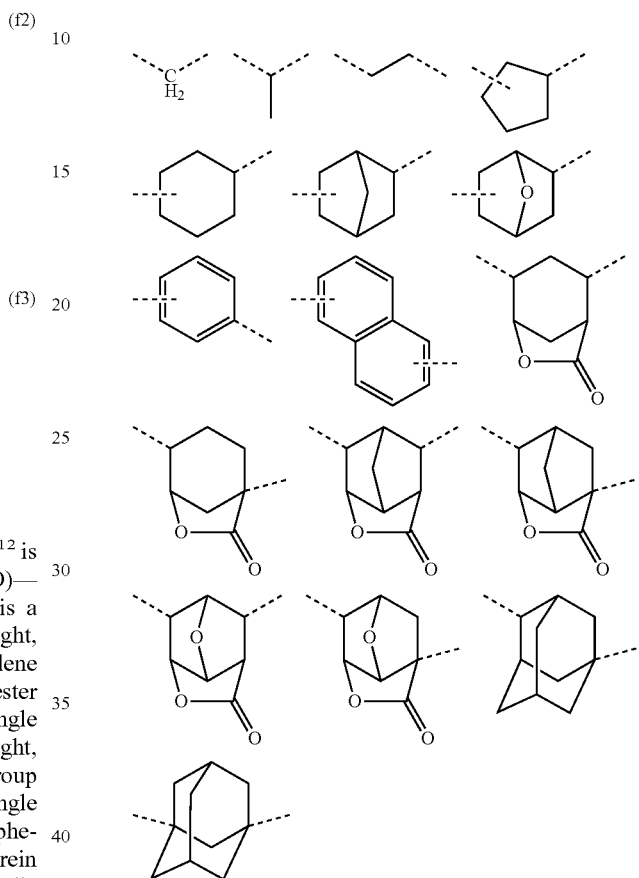

When a pair of R13 and R14 bond together to form a ring with the sulfur atom to which they are attached, and any two or more of R15, R16 and R17, or any two or more of R18, R19 and R20 bond together to form a ring with the sulfur atom to which they are attached, examples of the ring are shown below, but not limited thereto.

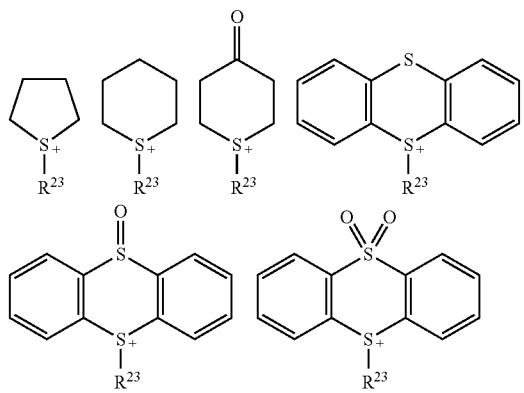

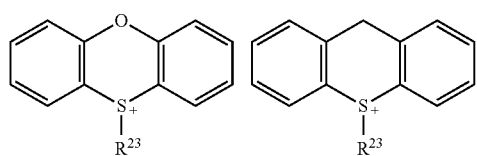
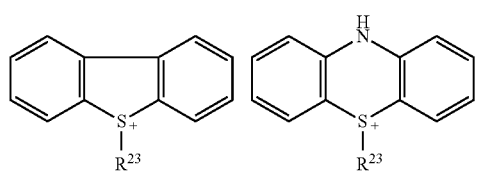
In the formulae, $R^{23}$ is a straight, branched or cyclic $C_1$-$C_{20}$ monovalent hydrocarbon group which may be substituted with or separated by a heteroatom. Suitable monovalent hydrocarbon groups are as exemplified above for $R^{13}$ to $R^{20}$.
Illustrative, non-limiting examples of the sulfonium cation in formulae (f2) and (f3) are given below.
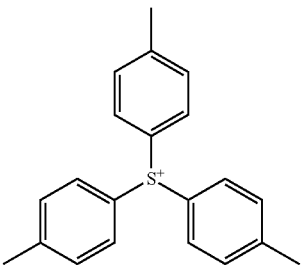
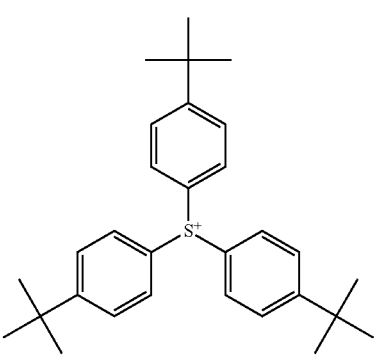
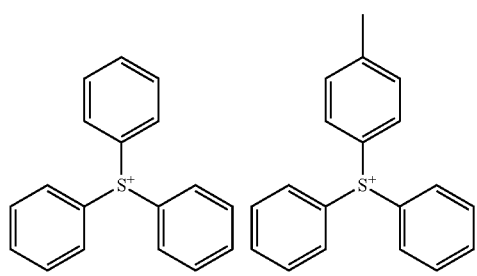
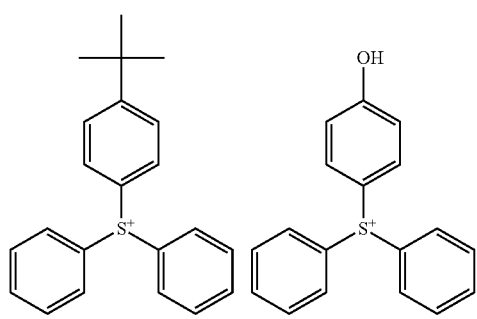
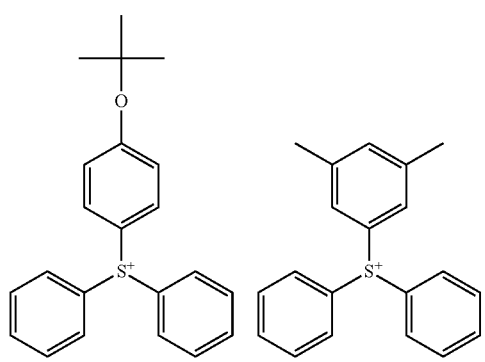
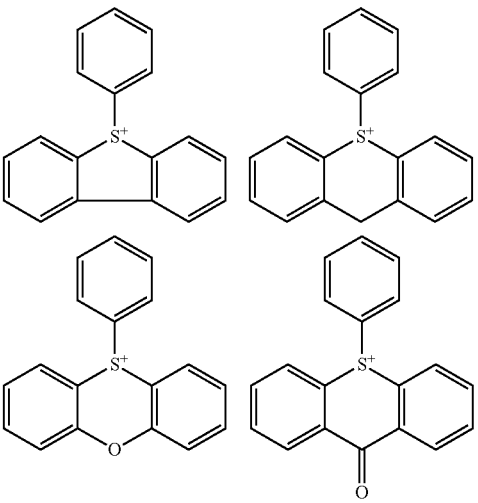

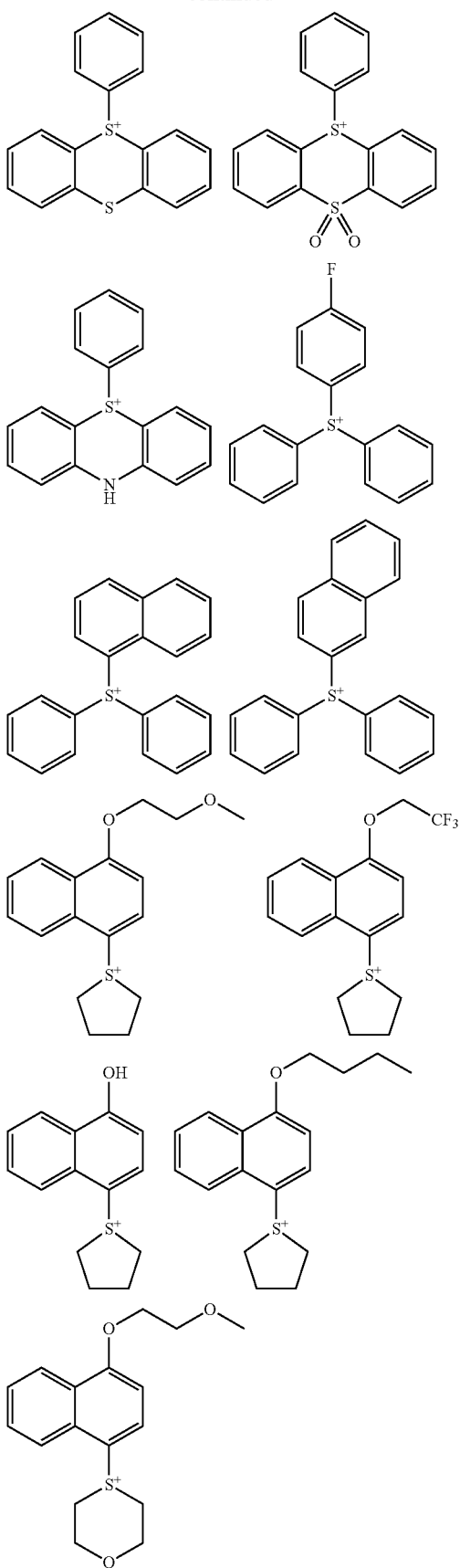

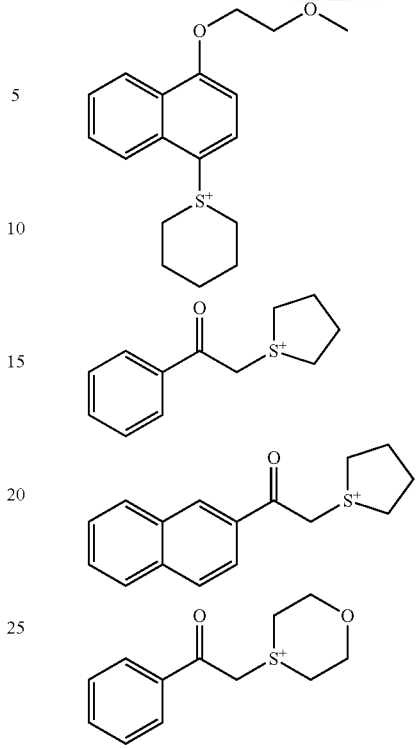

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl) imide; and methidates such as tris(trifluoromethylsulfonyl)methide and tris(perfluoroethylsulfonyl)methide.

Also included are a sulfonate which is fluorinated at α-position as represented by the general formula (F-1) and a sulfonate which is fluorinated at α- and β-positions as represented by the general formula (F-2).

$$R^{31}-CF_2-SO_3^- \quad (F-1)$$

$$R^{32}-O-\underset{F_3C}{\overset{}{C}}H-CF_2-SO_3^- \quad (F-2)$$

In formula (F-1), $R^{31}$ is hydrogen, or a straight, branched or cyclic $C_1$-$C_{20}$ alkyl group, straight, branched or cyclic $C_2$-$C_{20}$ alkenyl group or $C_6$-$C_{20}$ aryl group, which may have an ether, ester, carbonyl moiety, lactone ring or fluorine atom. In formula (F-2), $R^{32}$ is hydrogen, or a straight, branched or cyclic $C_1$-$C_{30}$ alkyl group, straight, branched or cyclic $C_2$-$C_{30}$ acyl group, straight, branched or cyclic $C_2$-$C_{20}$ alkenyl group, $C_6$-$C_{20}$ aryl group or $C_6$-$C_{20}$ aryloxy group, which may have an ether, ester, carbonyl moiety or lactone ring.

Furthermore, recurring units (g) having an oxirane or oxetane ring may be copolymerized. When recurring units (g) are copolymerized, it is expected that when the polymer is used in a resist composition, the exposed region of a resist film is crosslinked, leading to improvements in insolubilization in alkaline developer and etch resistance of negative pattern. Examples of recurring units (g) having an oxirane or oxetane ring are shown below, but not limited thereto. Note that $R^1$ is as defined above.

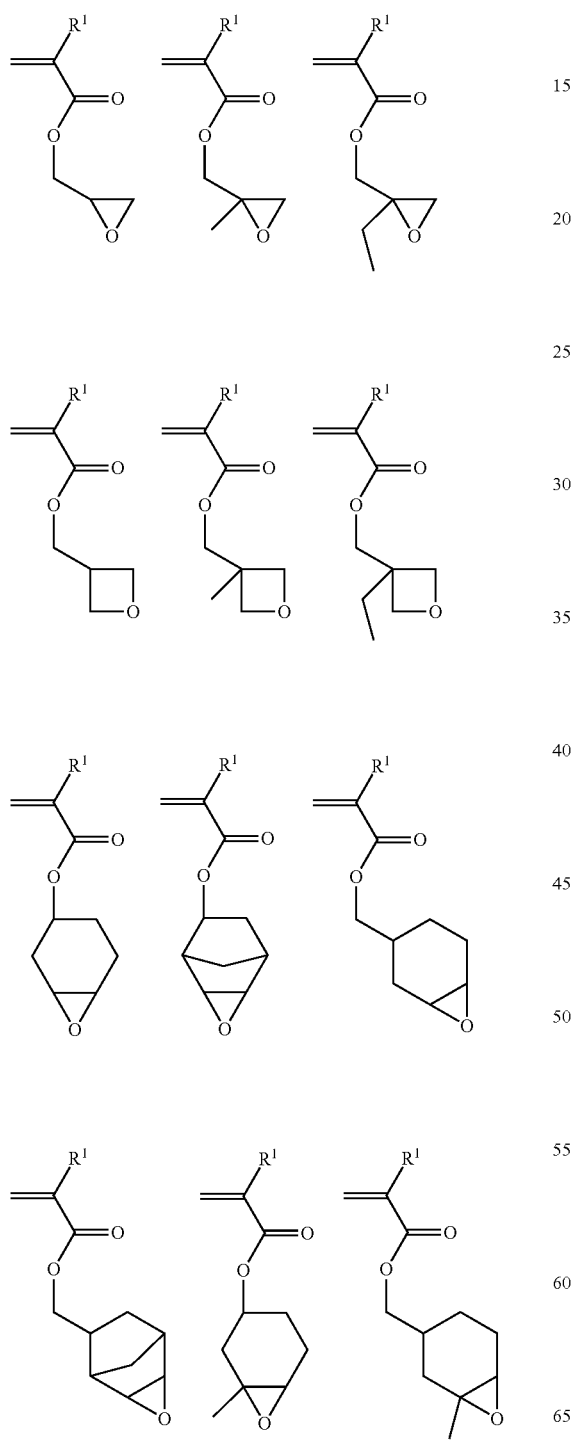

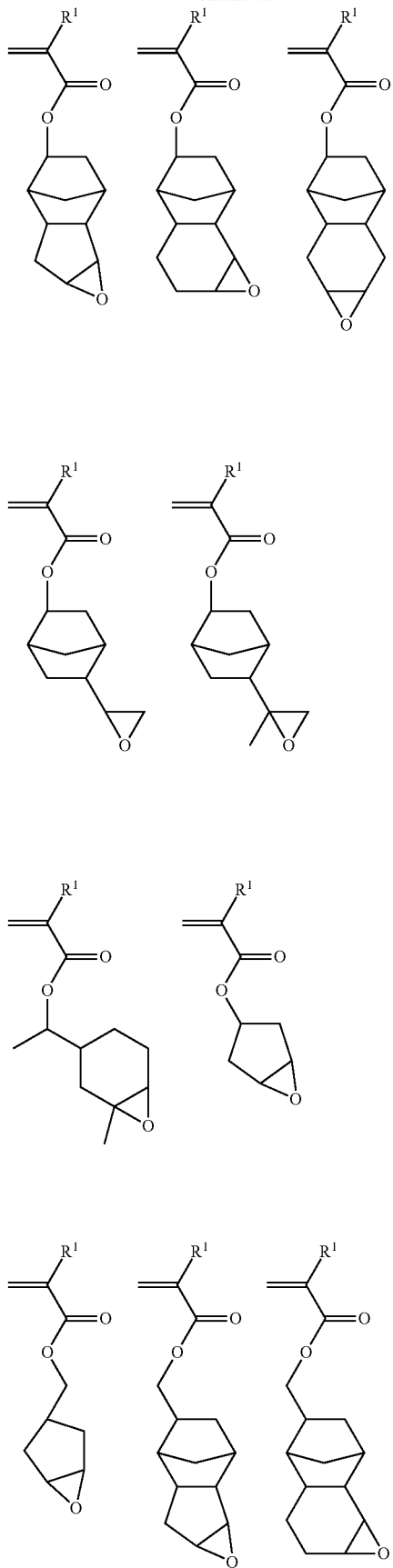

-continued
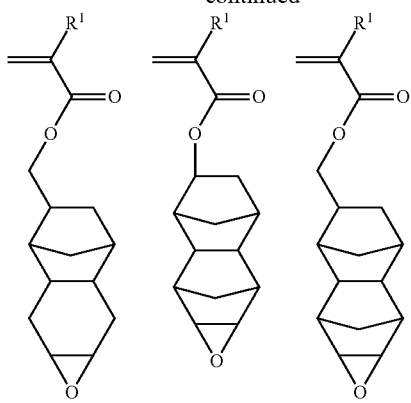
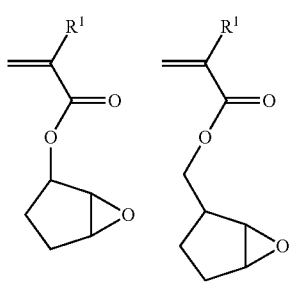
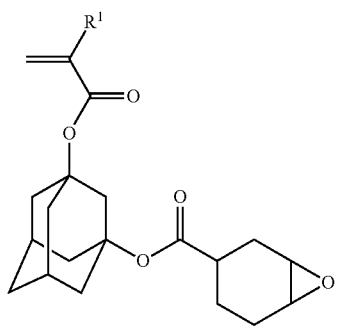
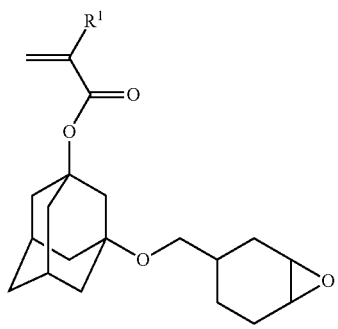
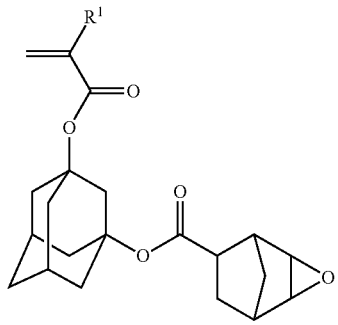
-continued
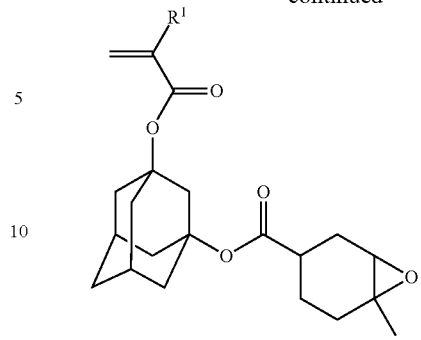
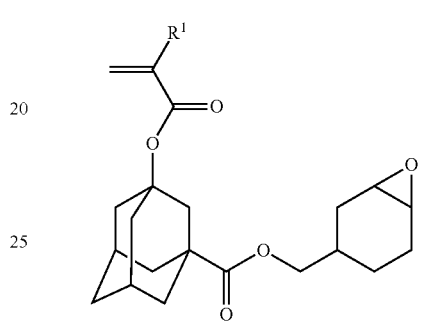
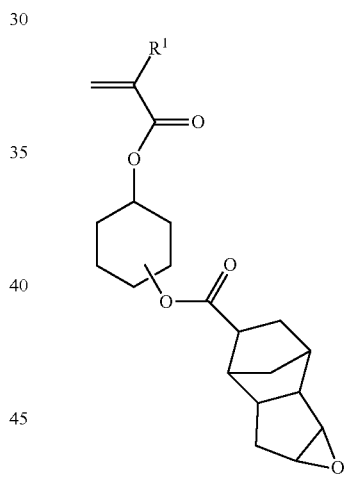
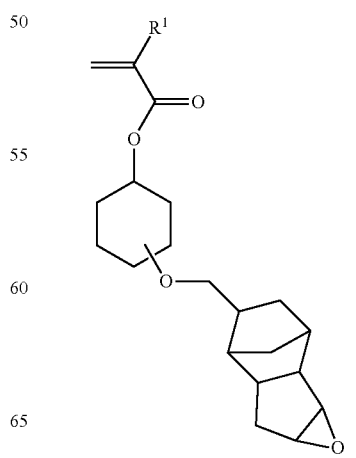

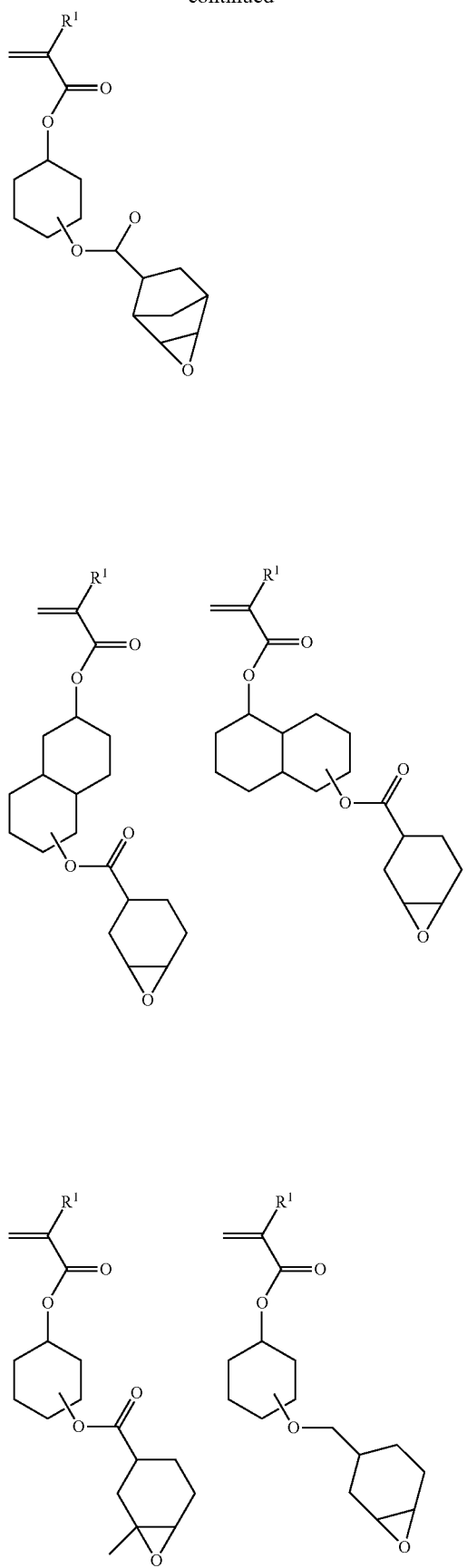
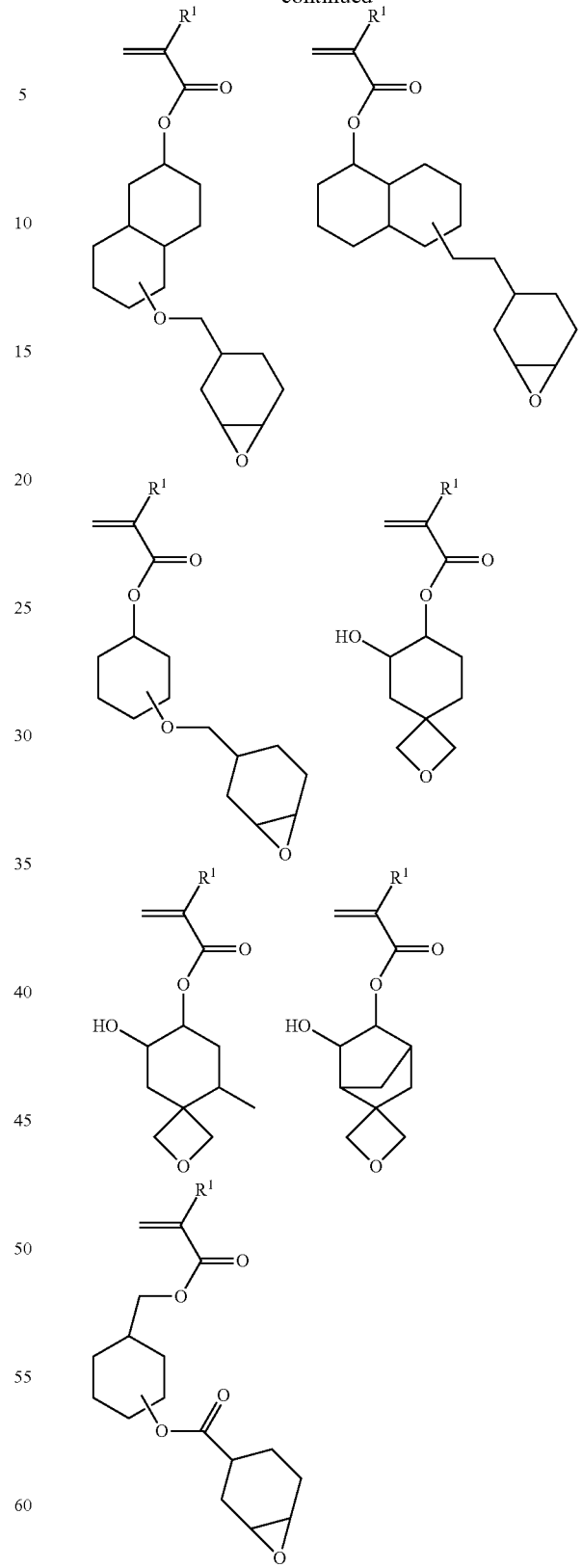
In addition to the foregoing units, the polymer may further comprise recurring units (h) derived from carbon-to-carbon double bond-bearing monomers. Examples include recurring units derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo [4.4.0.1$^{2,5}$.1$^{7,10}$]dodecene derivatives, unsaturated acid anhydrides such as itaconic anhydride, and other monomers shown below. In the following examples, $R^1$ is as defined above.

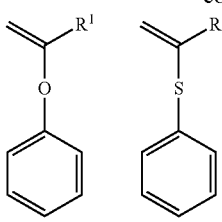

-continued

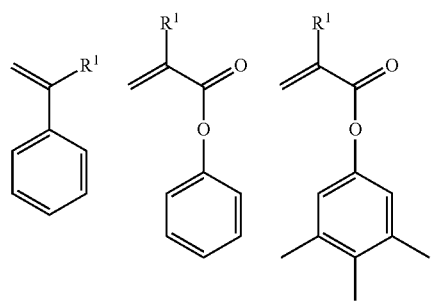

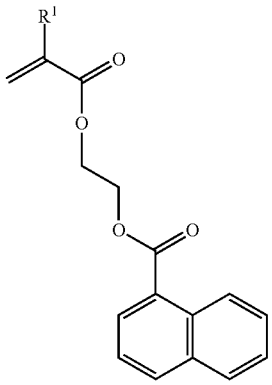

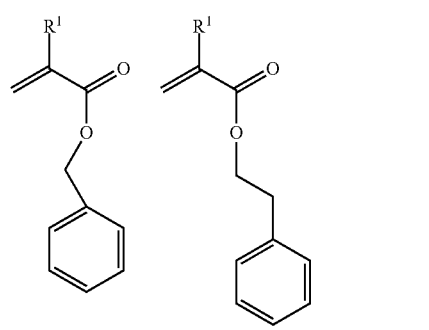

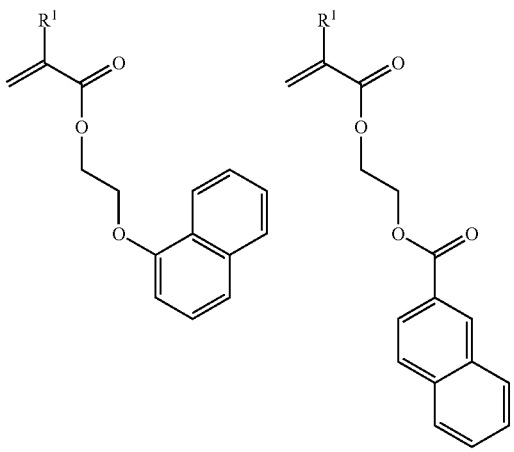

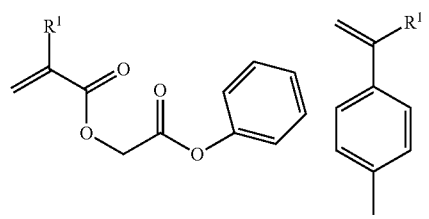

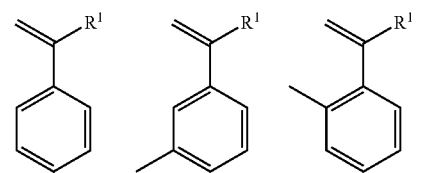

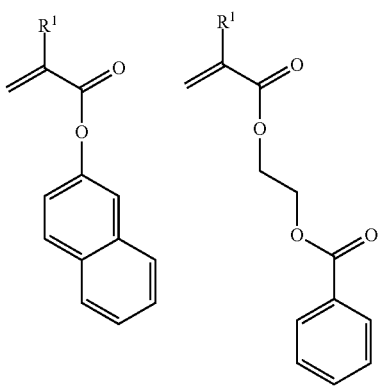

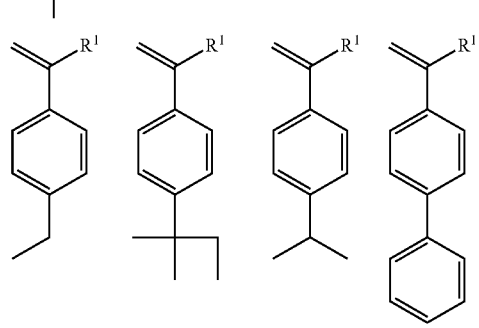

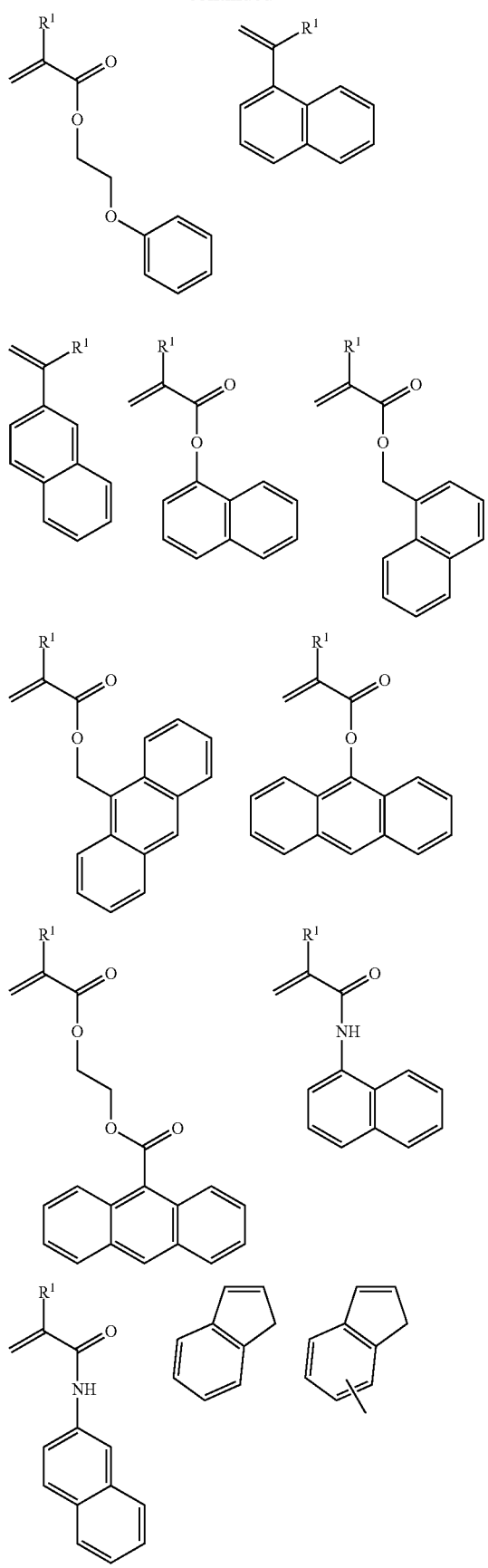
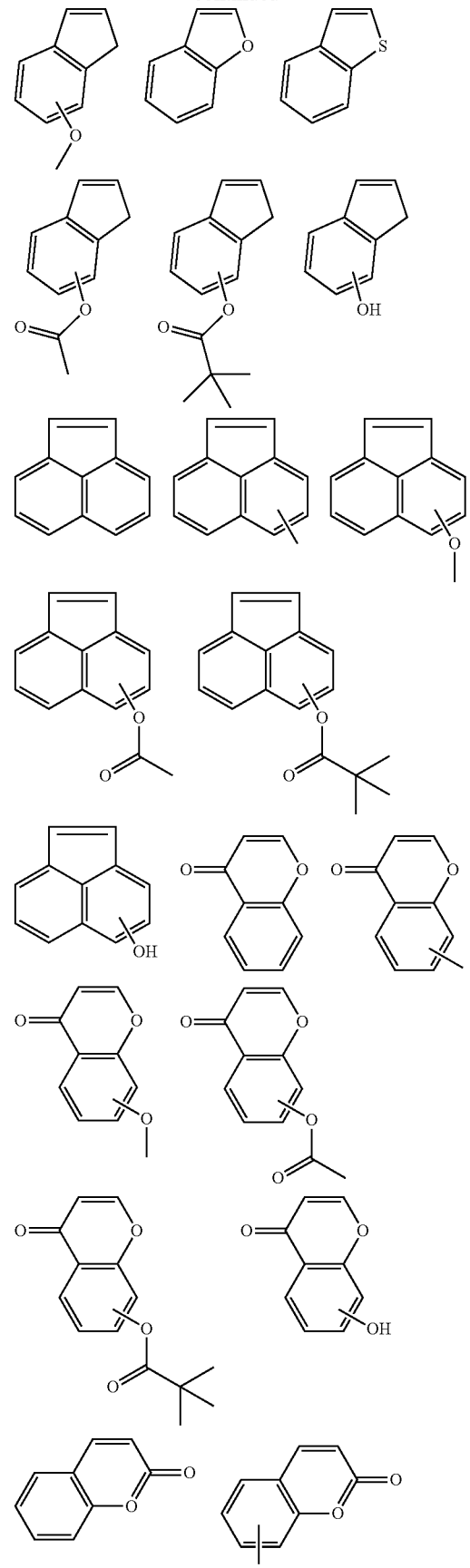

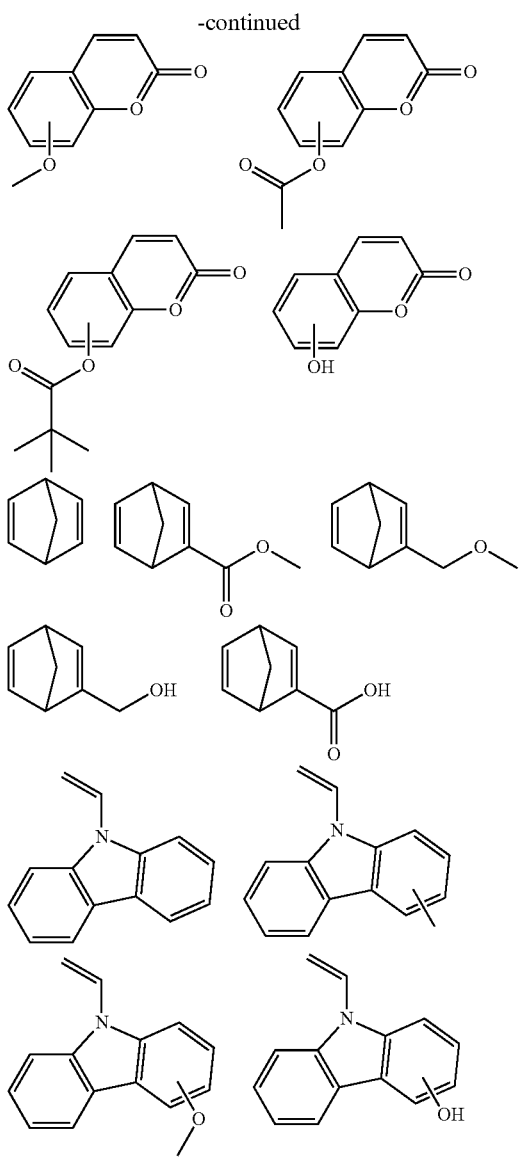

In the polymer, the recurring units derived from the inventive monomer and other monomers are preferably incorporated in the following molar fractions (mol %):

(I) more than 0 mol % to 100 mol %, preferably 5 to 80 mol %, and more preferably 10 to 60 mol % of constituent units of at least one type having formula (3) derived from monomer of formula (1);

(II) 0 mol % to less than 100 mol %, preferably 20 to 95 mol %, and more preferably 40 to 90 mol % of constituent units of at least one type selected from units (A) to (D);

(III) 0 to 30 mol %, preferably 0 to 20 mol %, and more preferably 0 to 10 mol % of constituent units of at least one type selected from units (f1) to (f3); and (IV) 0 to 80 mol %, preferably 0 to 70 mol %, and more preferably 0 to 50 mol % of constituent units of at least one type selected from units (g) and (h).

The polymer may be synthesized by any desired methods, for example, by dissolving one or more monomers corresponding to the selected recurring units in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, a copolymer may be obtained by dissolving hydroxystyrene or hydroxyvinylnaphthalene and another monomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The polymer should preferably have a weight average molecular weight (Mw) in the range of 1,000 to 500,000, and more preferably 3,000 to 50,000, as measured versus polystyrene standards by GPC using tetrahydrofuran solvent. Outside the range, there may result an extreme decline of etch resistance, a failure to provide a differential dissolution rate before and after exposure, and a lowering of resolution. Also preferably, the polymer has a molecular weight distribution or dispersity (Mw/Mn) of 1.20 to 2.20, more preferably 1.30 to 1.80.

Resist Composition

The inventive polymer is advantageously used as a base resin in a resist composition. Specifically, the polymer is used as a base resin and combined with any desired components including an organic solvent, acid generator, dissolution regulator, basic compound, surfactant, and acetylene alcohol to formulate a resist composition.

The resist composition comprising the inventive polymer has a very high sensitivity in that the dissolution rate in alkaline developer of the polymer in the exposed region is reduced by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Inclusion of a dissolution regulator may lead to an increased difference in dissolution rate between exposed and unexposed regions and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified negative resist composition. Typical of the acid generator used herein is a photoacid generator (PAG) capable of generating an acid in response to actinic light or radiation. Preferably the PAG is used in an amount of 0.5 to parts, more preferably 1 to 20 parts by weight per 100 parts by weight of the base resin. The PAG is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used. These compounds may be used alone or in admixture. Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection. Where the base polymer having recurring units (f1), (f2) or (f3) of acid generator copolymerized therein is used, the acid generator of addition type is not essential.

The preferred acid generators are those having the general formulae (Z1) and (Z2).

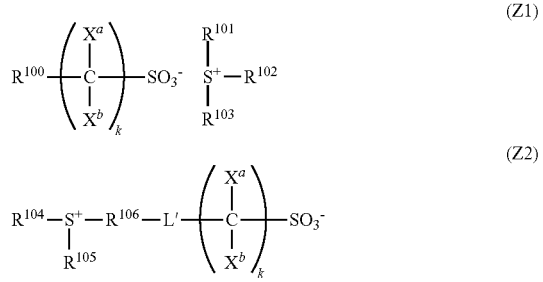

Herein $R^{100}$ is hydrogen, fluorine, or a straight, branched or cyclic $C_1$-$C_{35}$ monovalent hydrocarbon group which may contain a heteroatom. $X^a$ and $X^b$ are each independently hydrogen, fluorine, or trifluoromethyl, k is an integer of 1 to 4. $R^{101}$, $R^{102}$, and $R^{103}$ are each independently an optionally substituted, straight or branched $C_1$-$C_{10}$ alkyl, $C_1$-$C_{10}$ oxoalkyl or $C_2$-$C_{10}$ alkenyl group, or an optionally substituted $C_6$-$C_{18}$ aryl, $C_7$-$C_{19}$ aralkyl or aryloxoalkyl group, or any two or more of $R^{101}$, $R^{102}$, and $R^{103}$ may bond together to form a ring with the sulfur atom to which they are attached. $R^{104}$ and $R^{105}$ are each independently a straight, branched or cyclic $C_1$-$C_{20}$ monovalent hydrocarbon group which may be substituted with or separated by a heteroatom, or $R^{104}$ and $R^{105}$ may bond together to form a ring with the sulfur atom to which they are attached. $R^{106}$ is a straight, branched or cyclic $C_1$-$C_{20}$ divalent hydrocarbon group which may be substituted with or separated by a heteroatom. L' is a single bond or a straight, branched or cyclic $C_1$-$C_{20}$ divalent hydrocarbon group which may be substituted with or separated by a heteroatom.

Also preferred are acid generators having the general formulae (Z3) and (Z4).

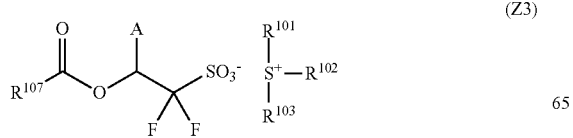

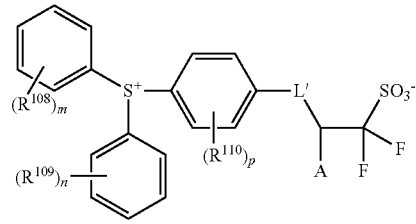

Herein A is hydrogen or trifluoromethyl. $R^{101}$, $R^{102}$, and $R^{103}$ are as defined above. $R^{107}$ is a straight, branched or cyclic $C_1$-$C_{35}$ monovalent hydrocarbon group which may contain a heteroatom. $R^{108}$, $R^{109}$, and $R^{110}$ are each independently hydrogen or a straight, branched or cyclic $C_1$-$C_{20}$ monovalent hydrocarbon group which may be separated by a heteroatom. Each of m and n is an integer of 0 to 5, p is an integer of 0 to 4. L' is a single bond, ether bond, or a straight, branched or cyclic $C_1$-$C_{20}$ divalent hydrocarbon group which may be substituted with or separated by a heteroatom.

When the acid generator is one having formula (Z3) or (Z4), preferably formula (Z3) or (Z4) wherein A is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of the acid generators having formulae (Z1) to (Z4) are shown below. Notably A is as defined above.

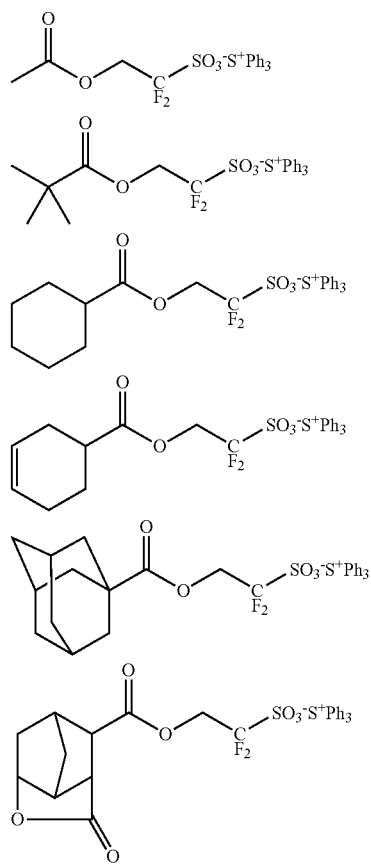

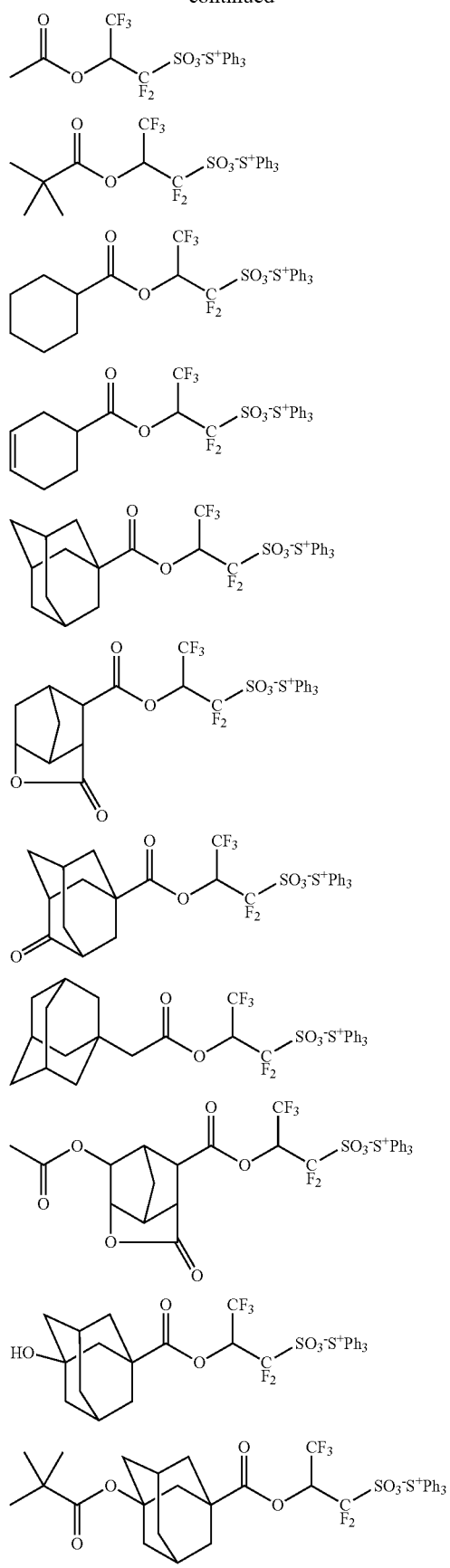
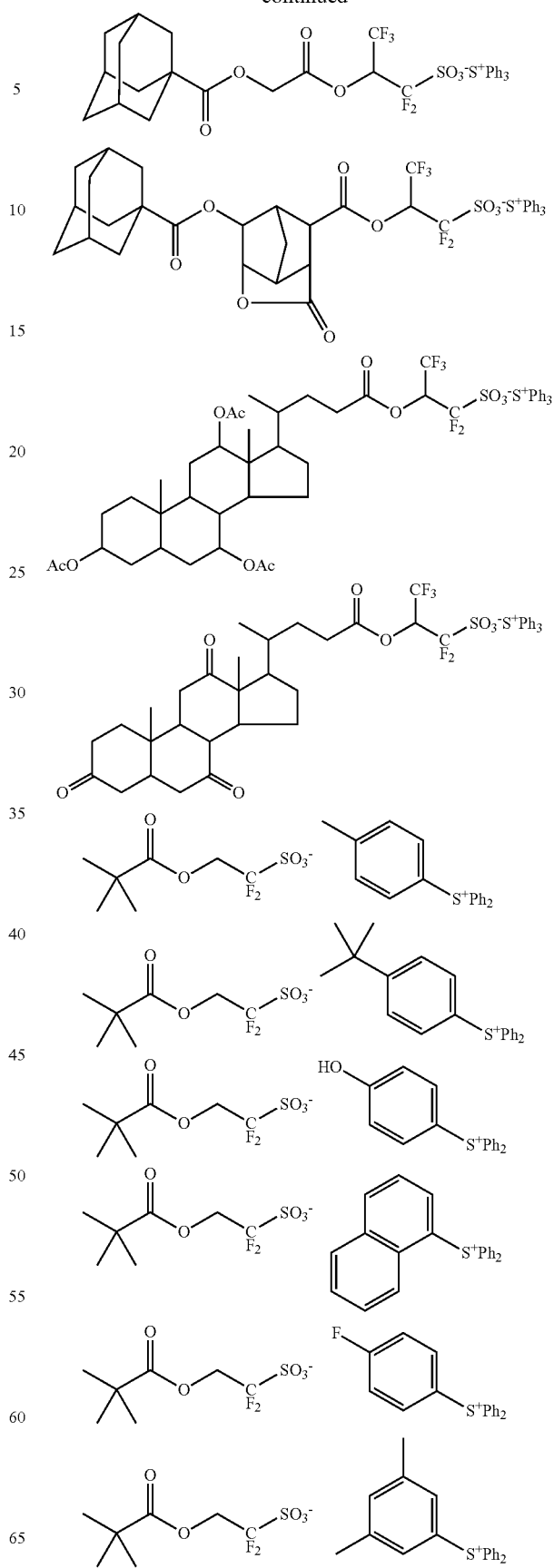

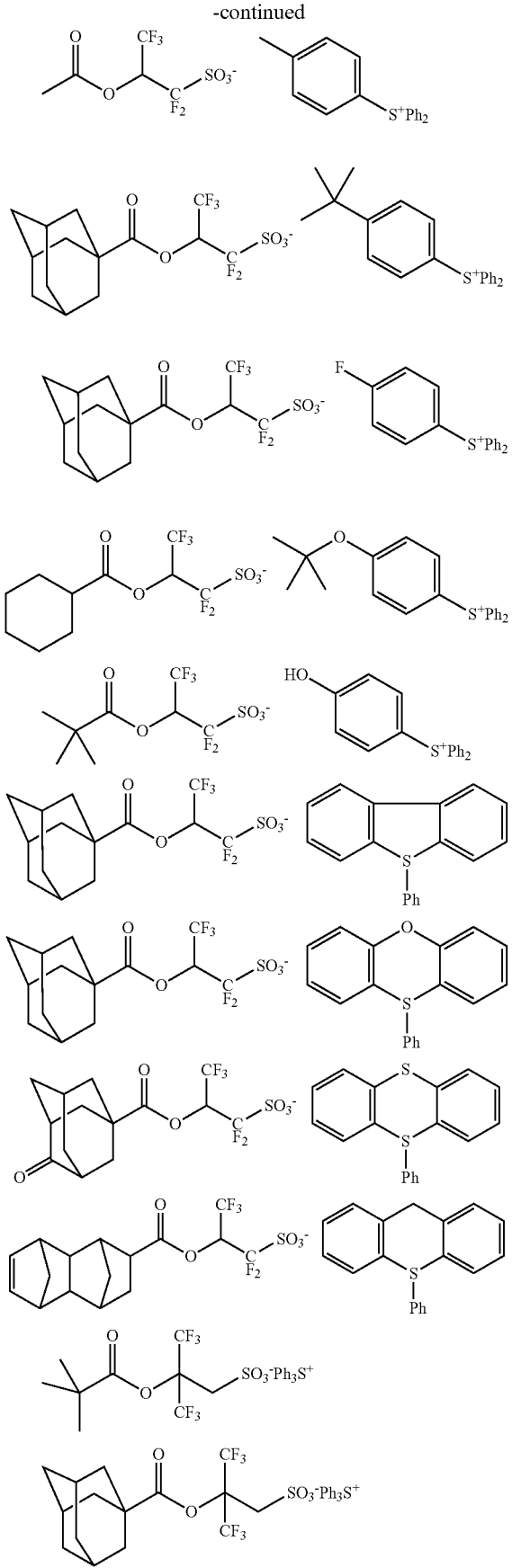
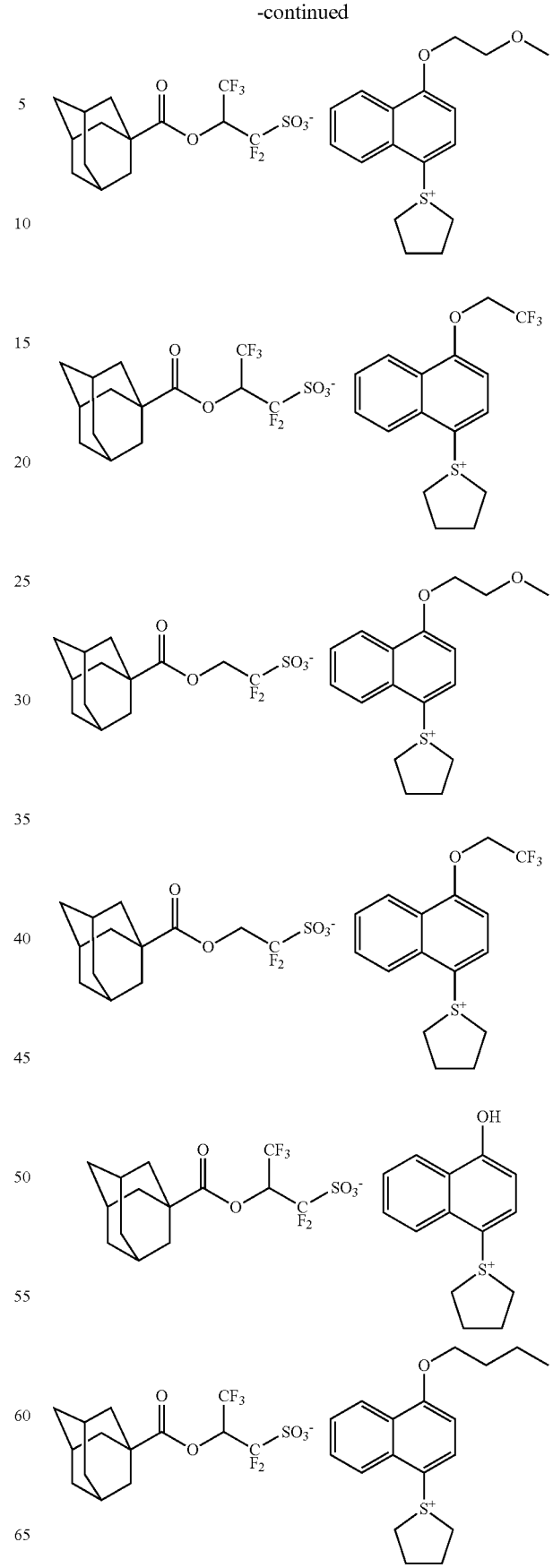

79
-continued
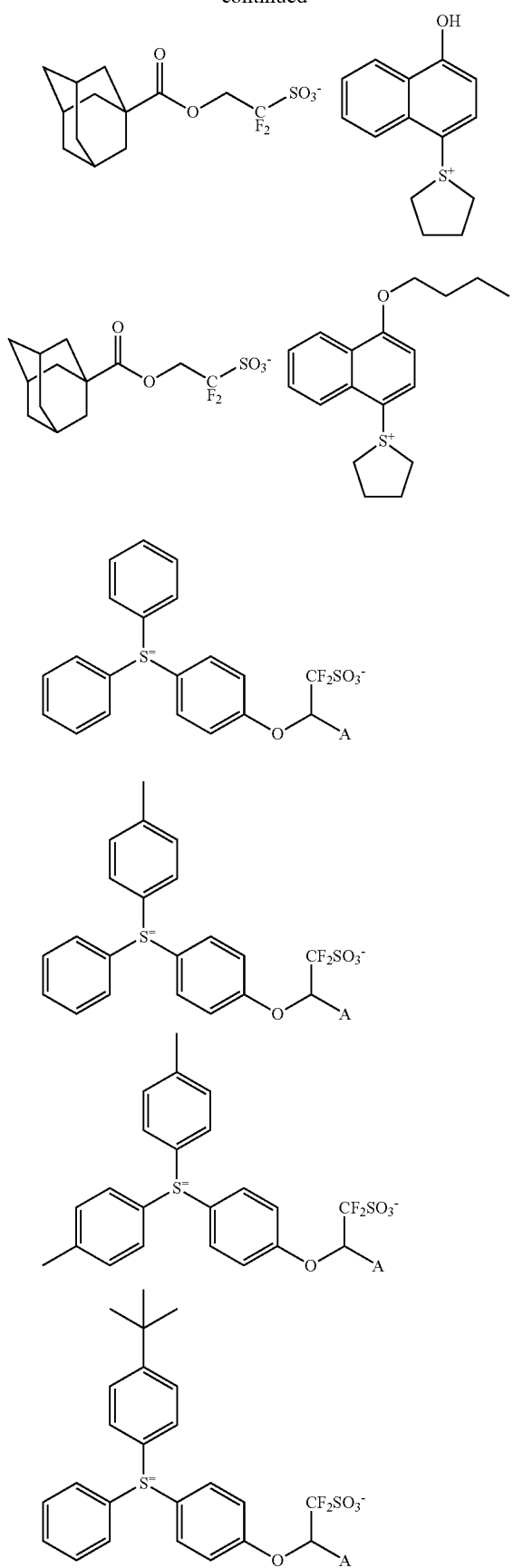
80
-continued
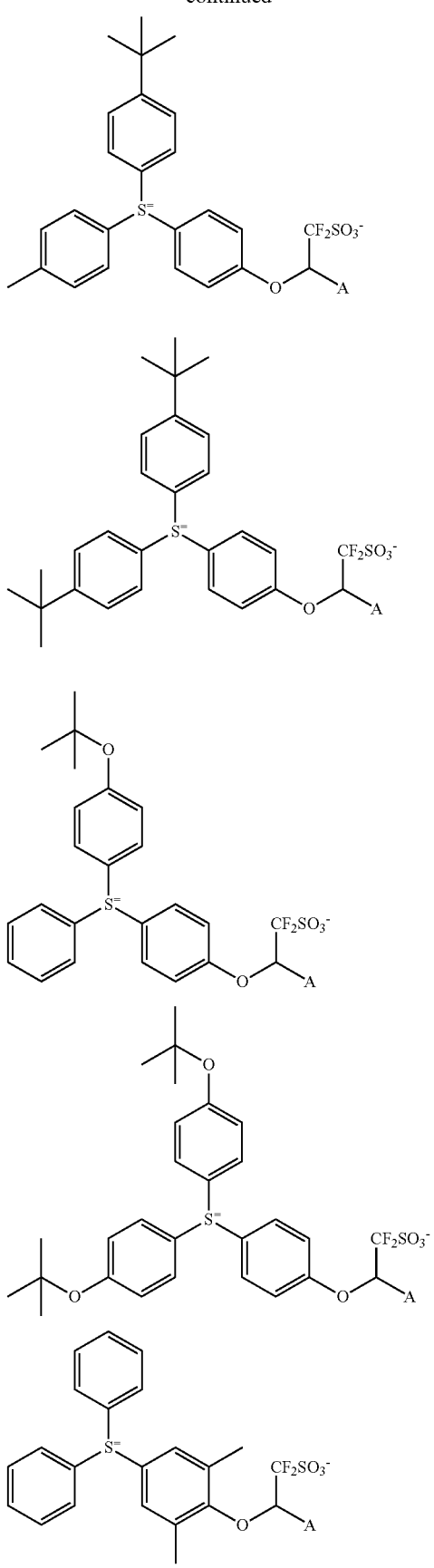

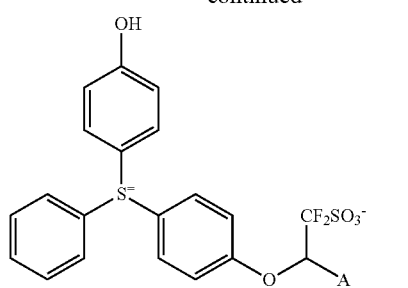
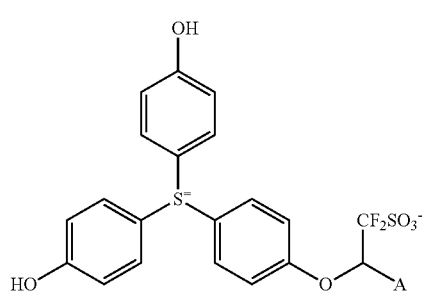
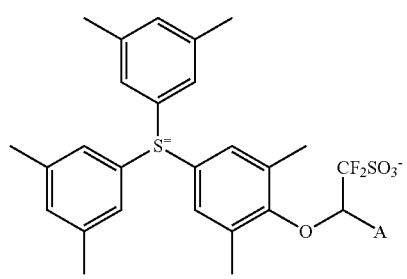
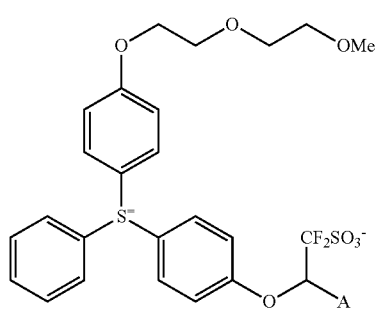
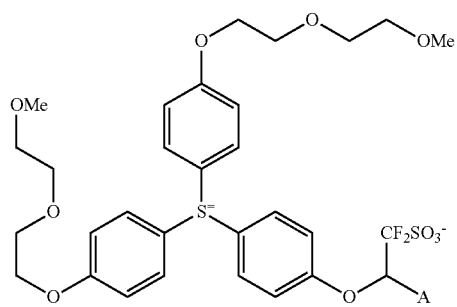
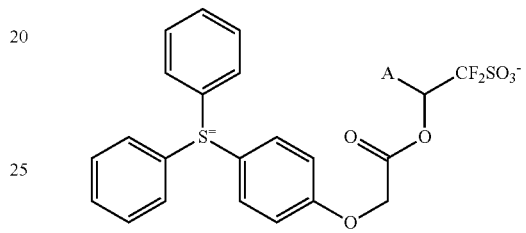
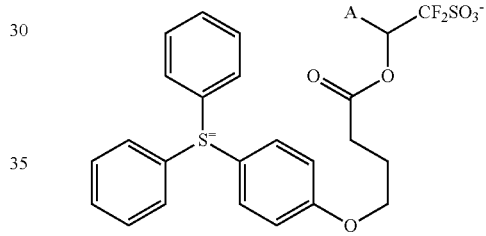
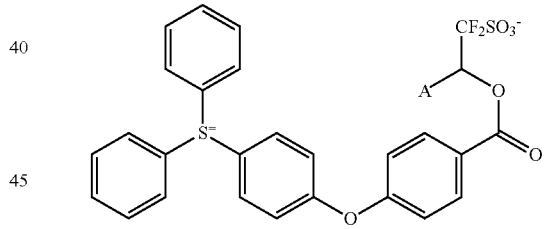
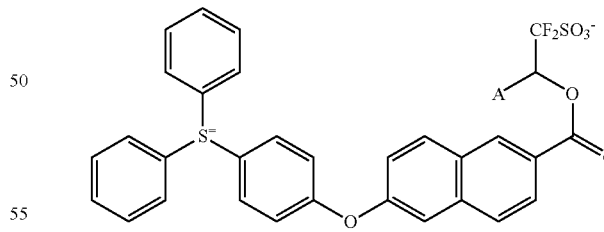
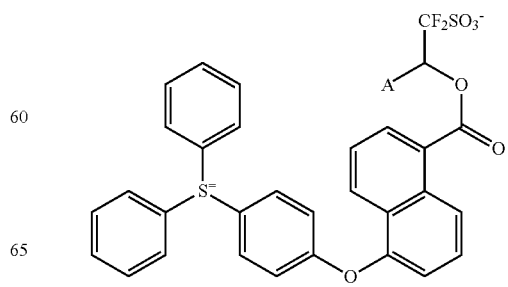

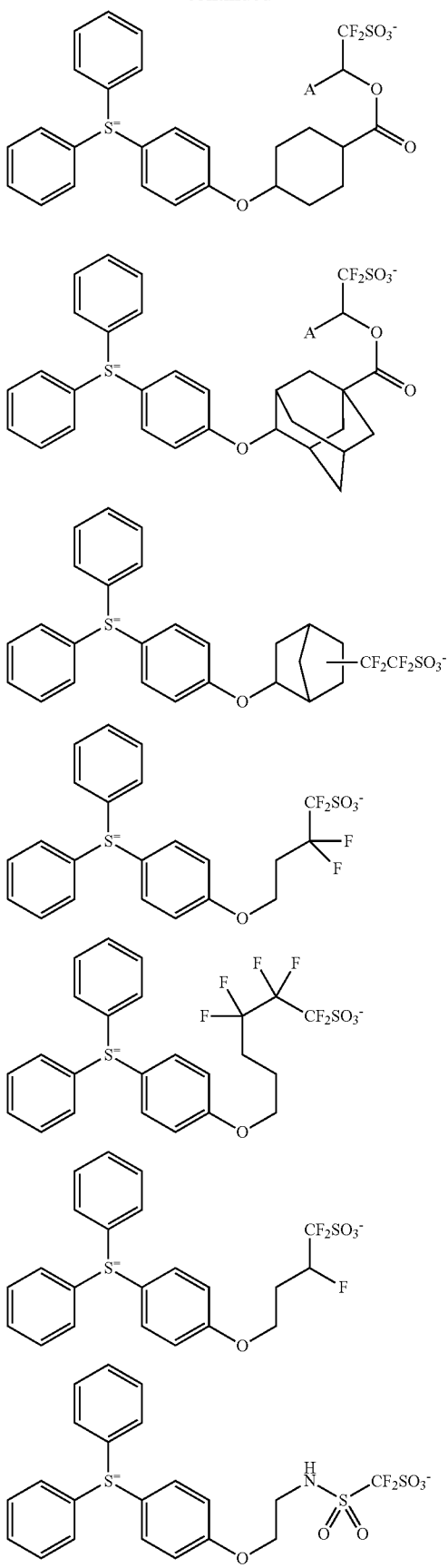
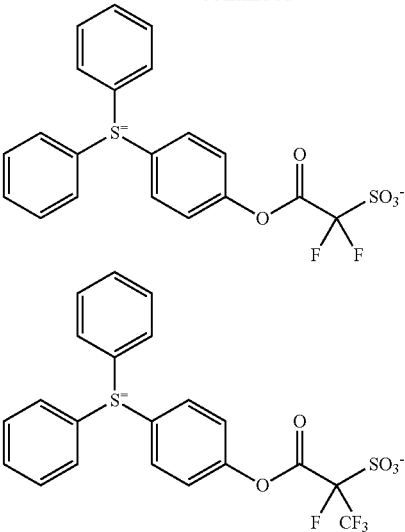

Suitable organic solvents include ketones such as cyclohexanone, cyclopentanone, methyl-2-n-amyl ketone, and diacetone alcohol; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone, which may be used alone or in admixture.

Examples of the basic compound used herein include primary, secondary, and tertiary amine compounds as described in JP-A 2008-111103 (U.S. Pat. No. 7,537,880), paragraphs [0146] to [0164], specifically amine compounds having a hydroxyl, ether, ester, lactone, cyano or sulfonic ester group, and compounds having a carbamate group as described in JP 3790649.

Onium salts such as sulfonium salts, iodonium salts and ammonium salts of sulfonic acids which are not fluorinated at α-position as described in US 2008153030 (JP-A 2008-158339) and similar onium salts of carboxylic acids as described in JP-A 2013-037092 may be used as the quencher. Where an α-position non-fluorinated sulfonic acid salt or carboxylic acid salt and an α-position fluorinated sulfonic acid, imide acid, or methide acid generated by a PAG are co-present, salt exchange occurs to generate an α-position non-fluorinated sulfonic acid or carboxylic acid. Since this α-position non-fluorinated sulfonic acid or carboxylic acid has an insufficient acid strength to induce deprotection reaction to the resist resin, the relevant sulfonium salt, iodonium salt or ammonium salt functions as a quencher. In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved focus margin or DOF and satisfactory dimensional control.

In case the polarity switching unit of formula (3) in the base resin has a high reactivity with acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Illustrative, non-limiting examples of the α-position non-fluorinated sulfonic acid salt and carboxylic acid salt are given below.

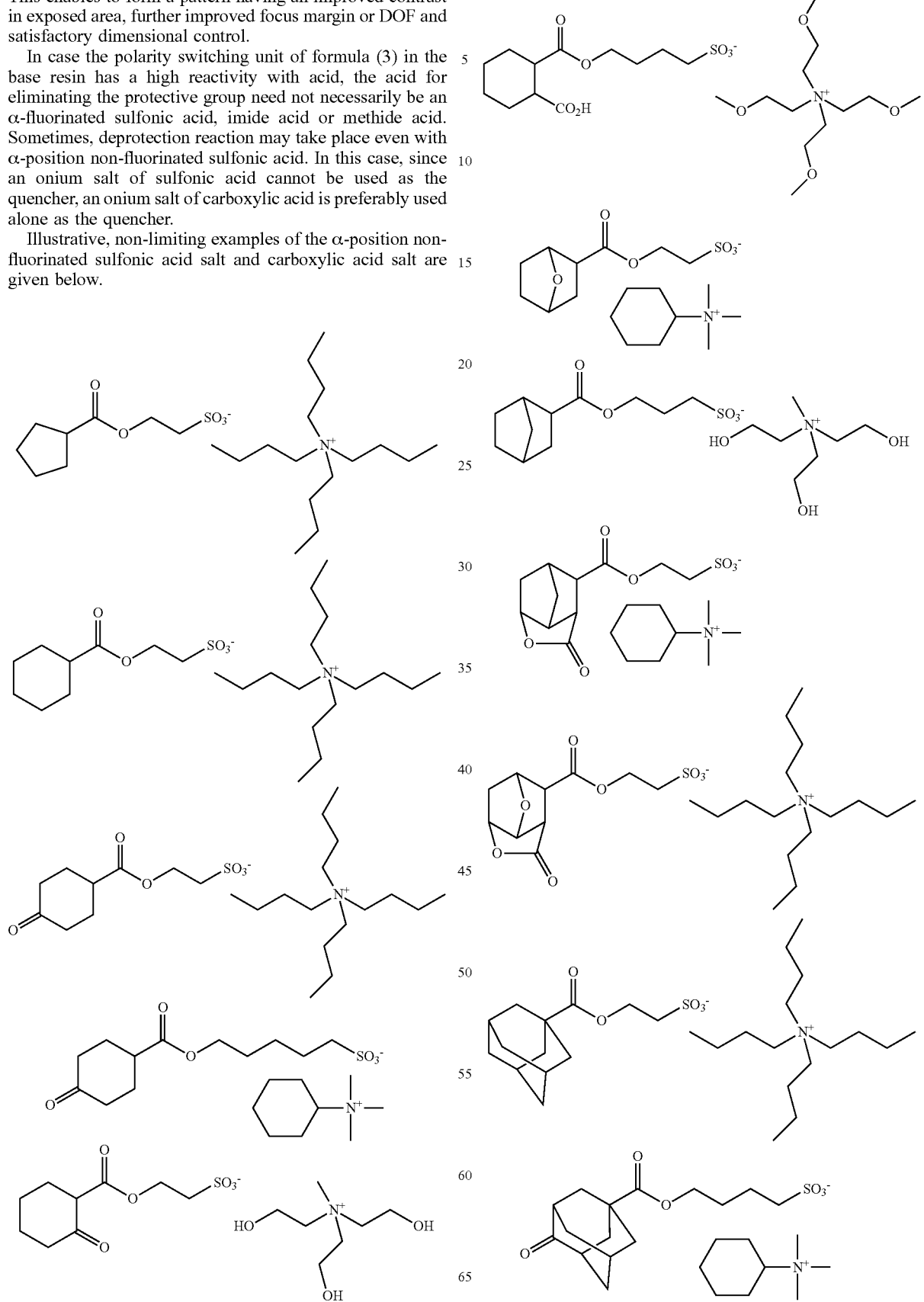

87
-continued
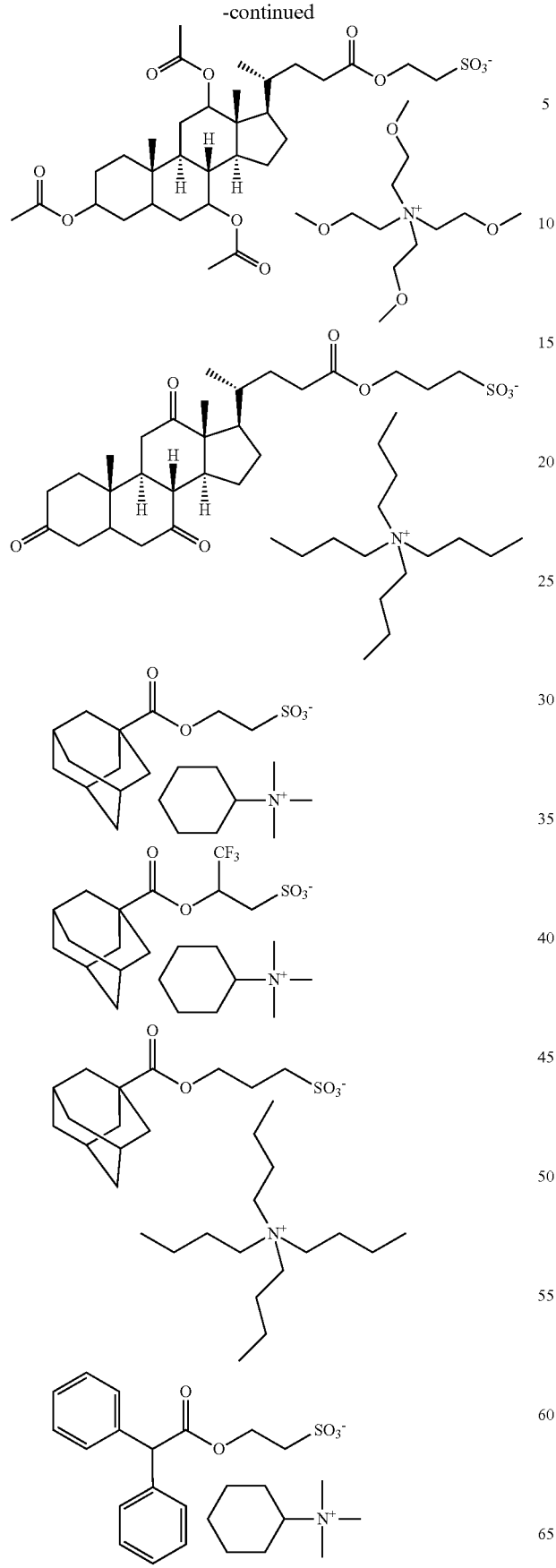
88
-continued
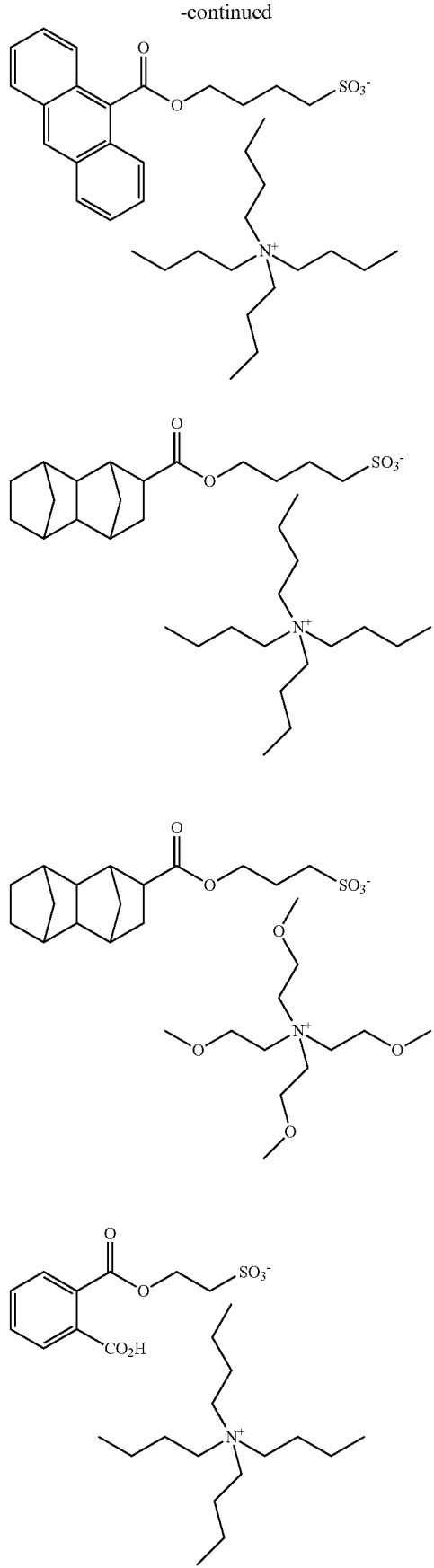

89
-continued
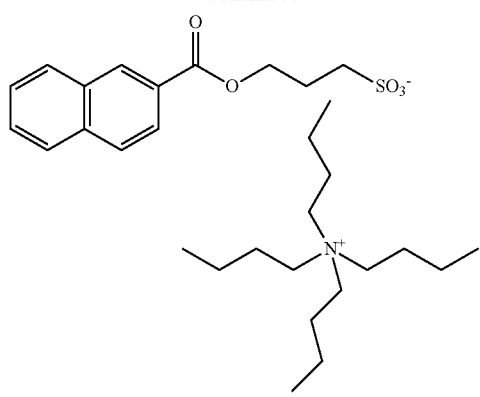
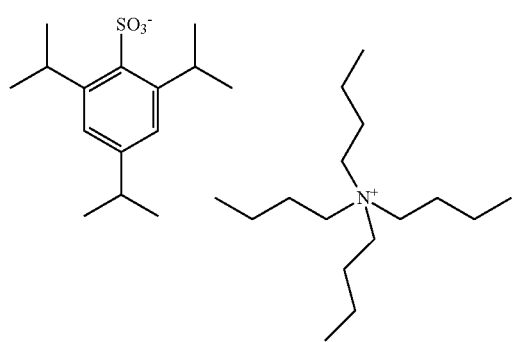
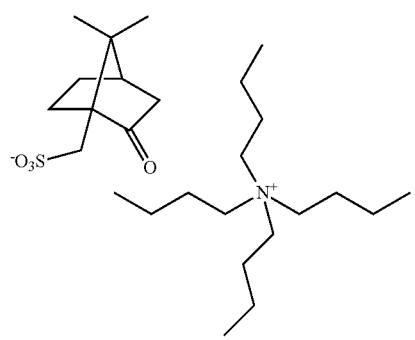
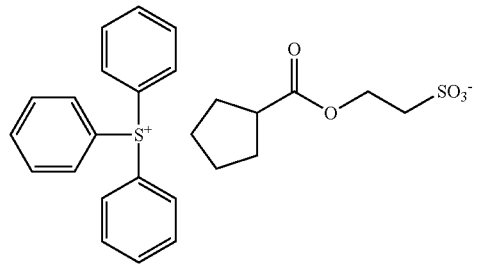
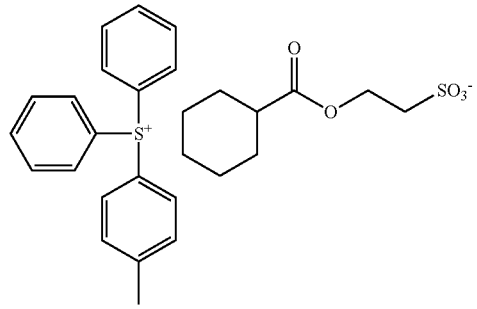
90
-continued
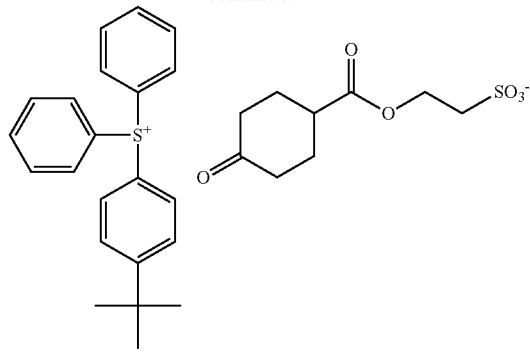

91
-continued
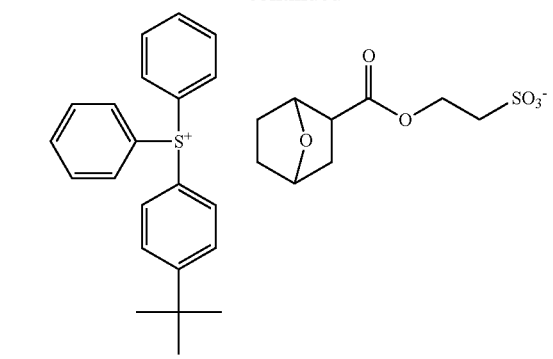
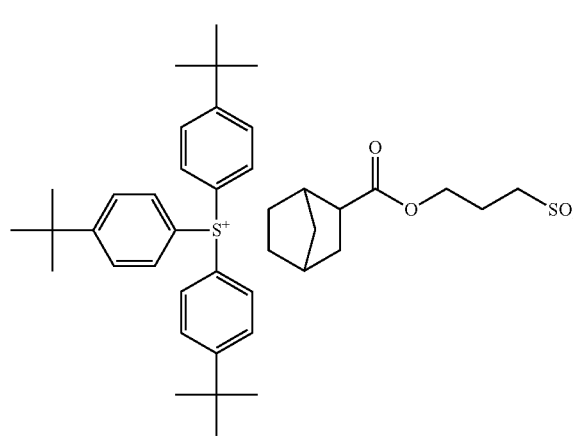
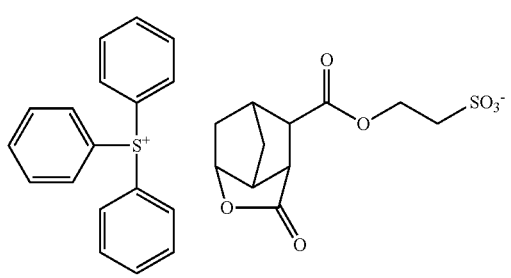
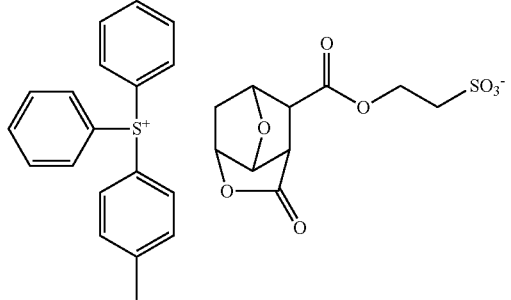
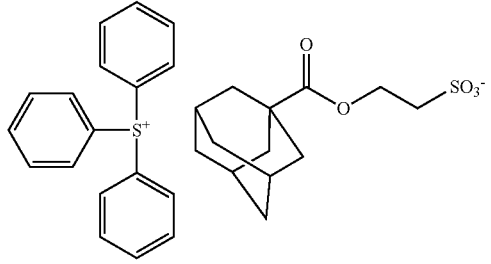
92
-continued
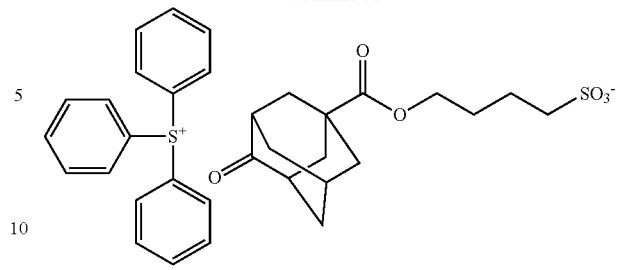
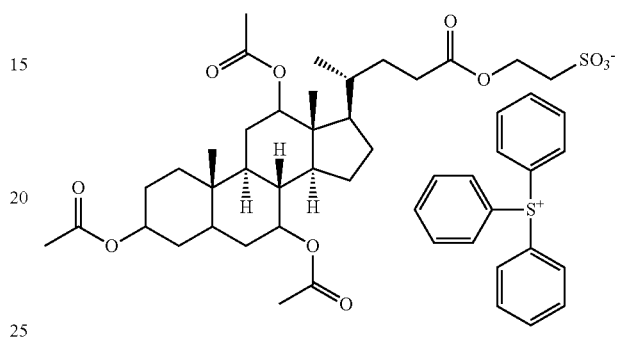
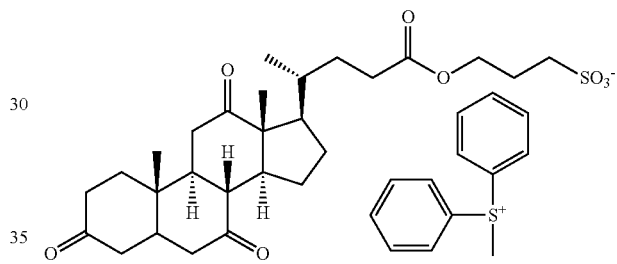
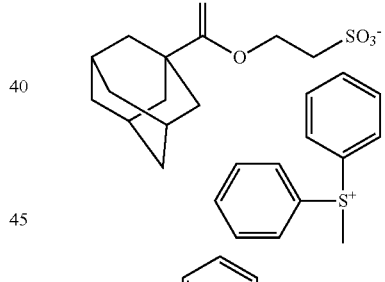
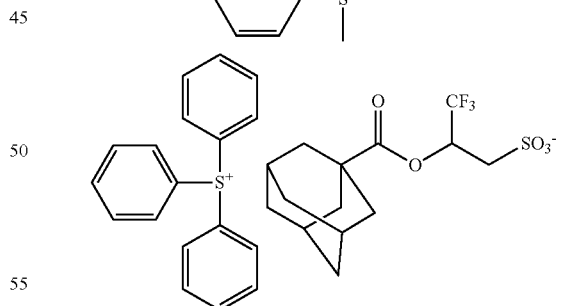
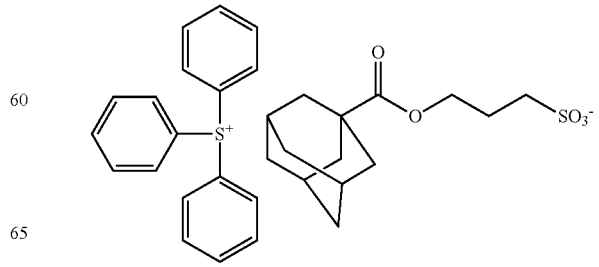

93
-continued
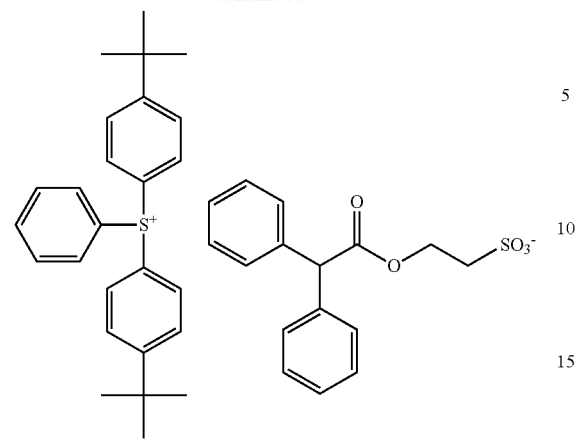
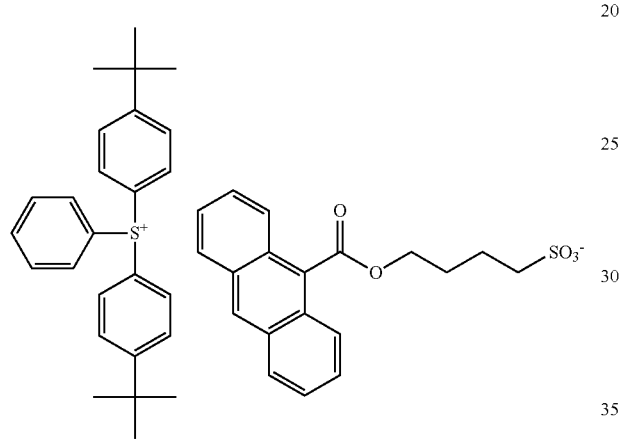
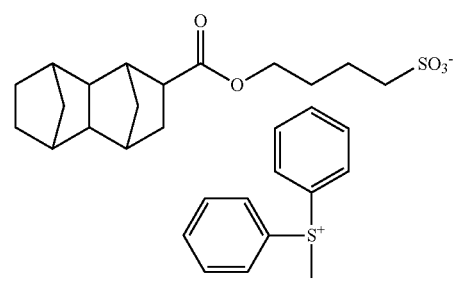
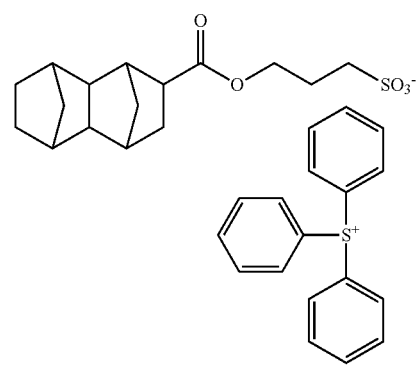
94
-continued
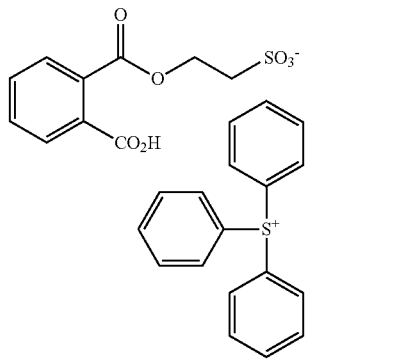
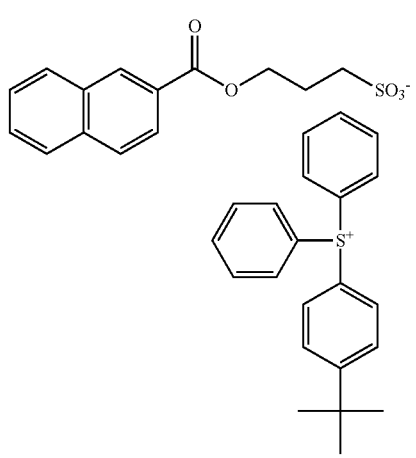
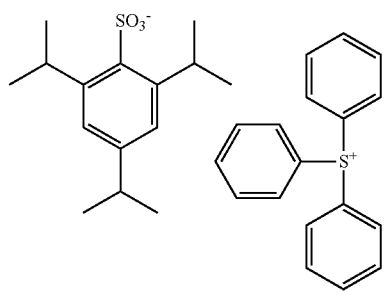
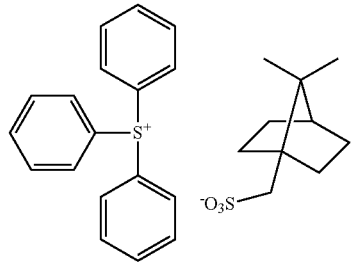
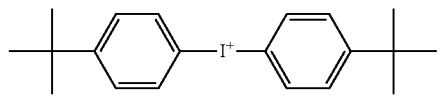

95
-continued
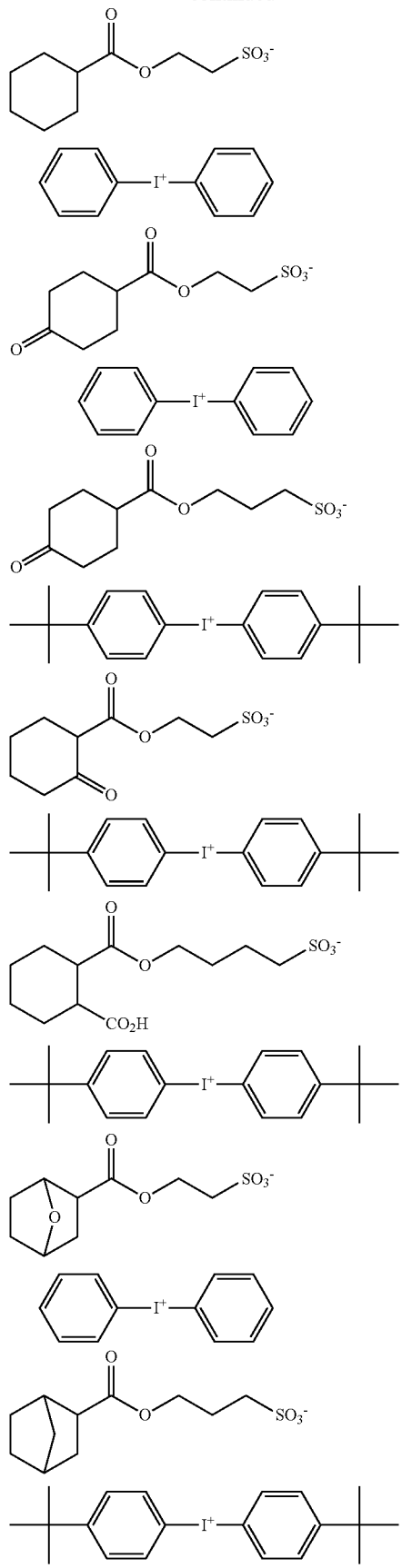
96
-continued
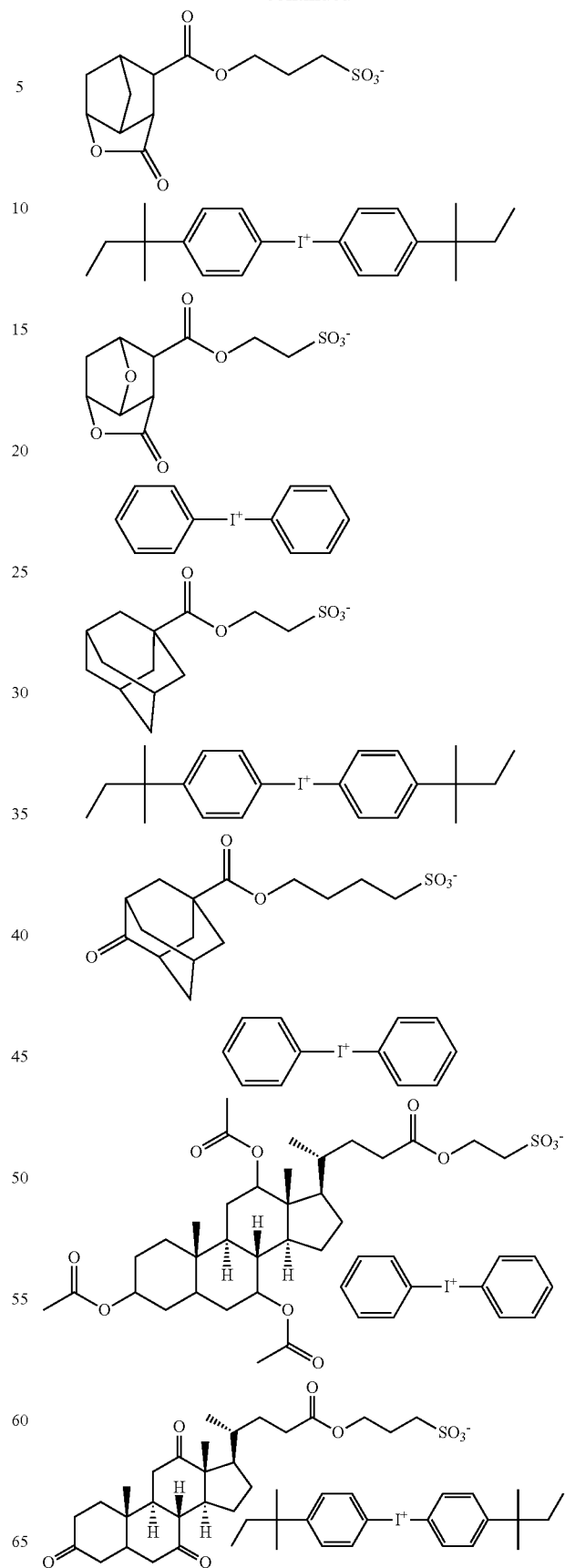

97
-continued
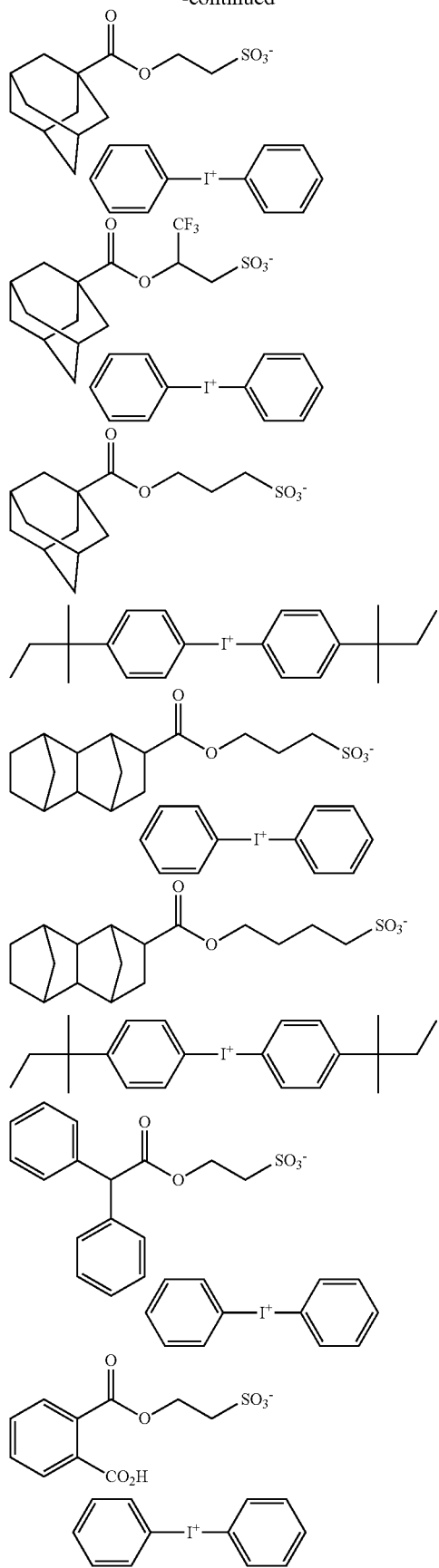
98
-continued
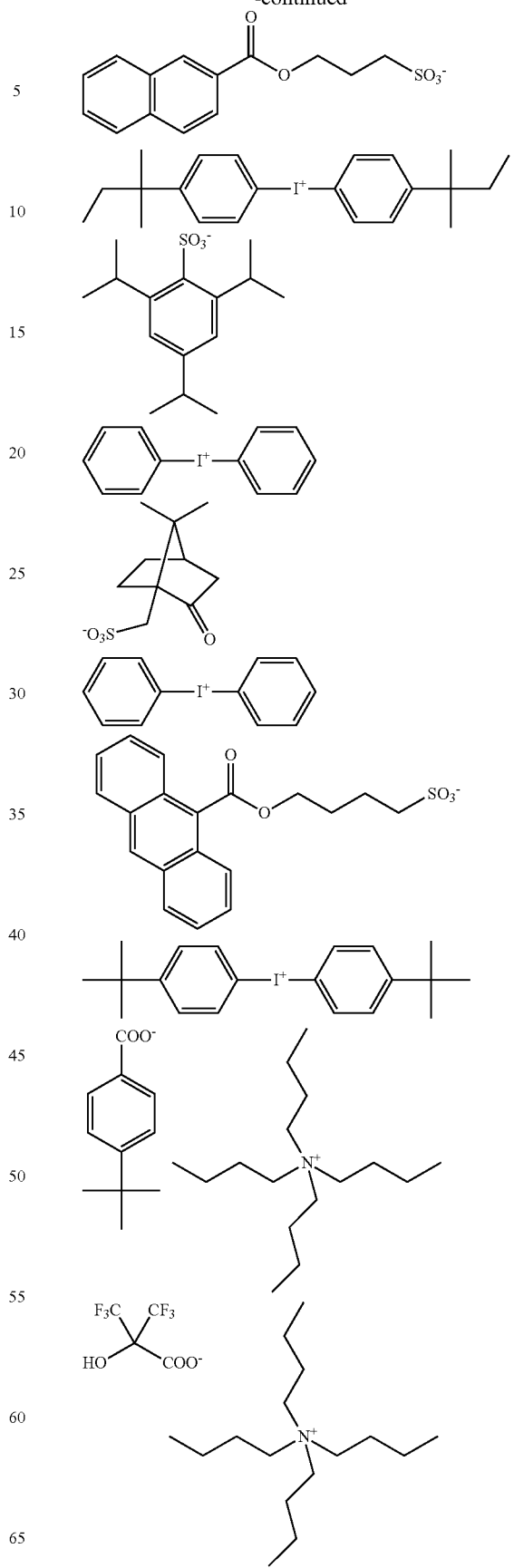

99
-continued
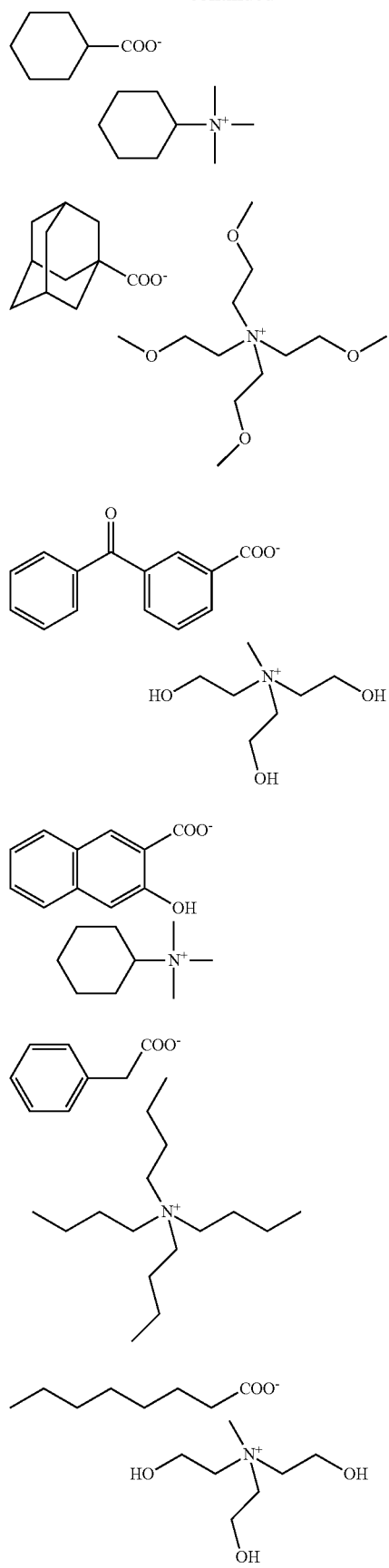
100
-continued
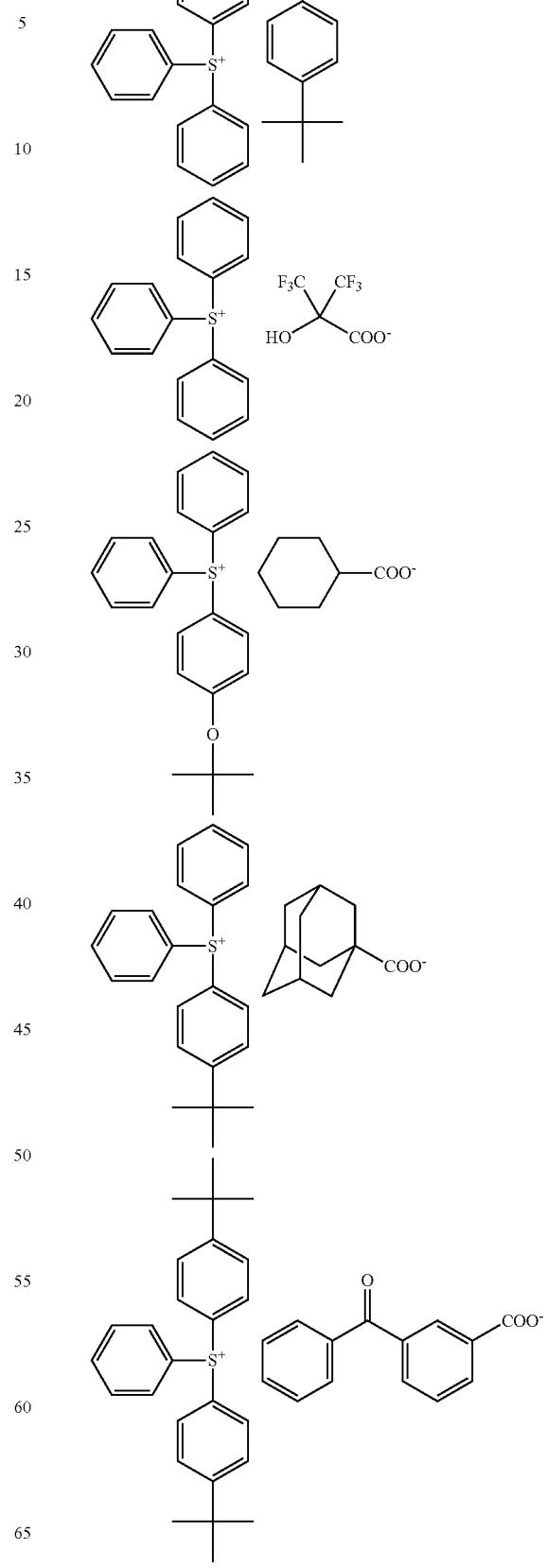

101
-continued
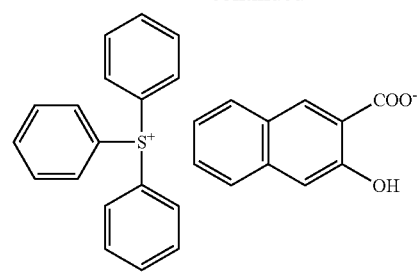
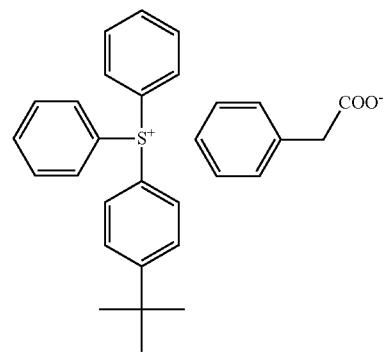
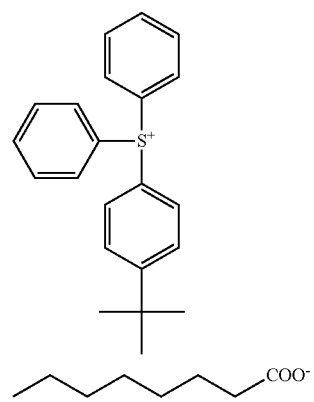
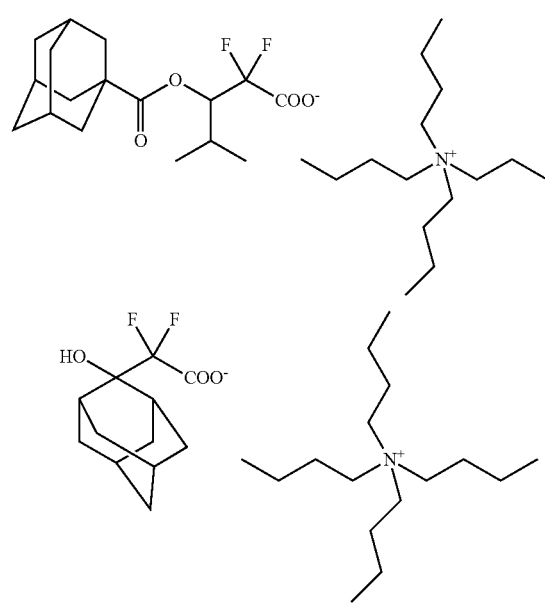
102
-continued
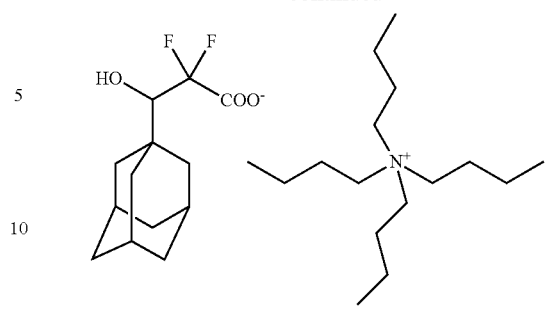
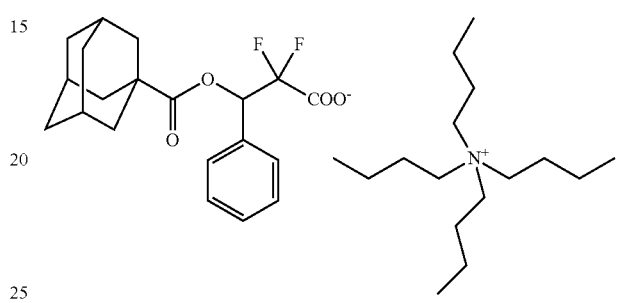
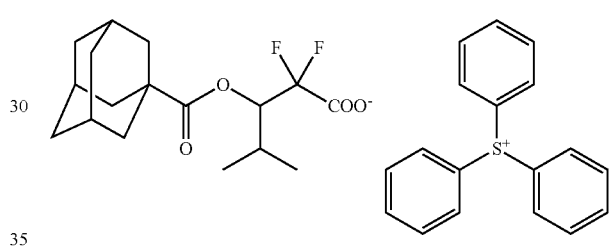
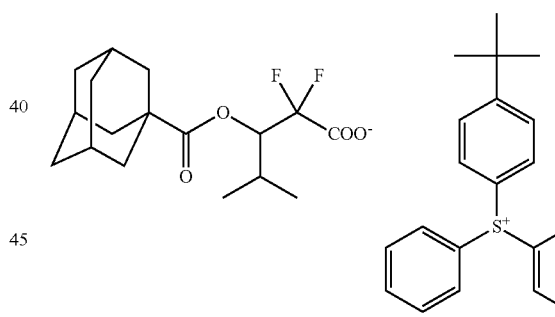
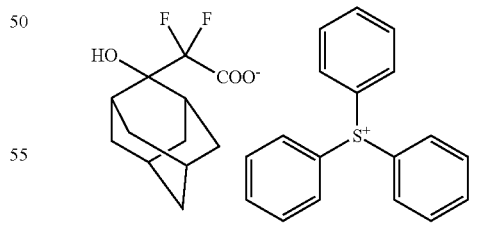
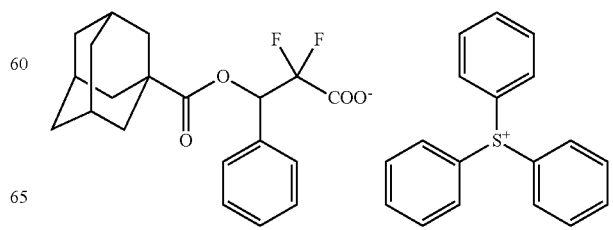

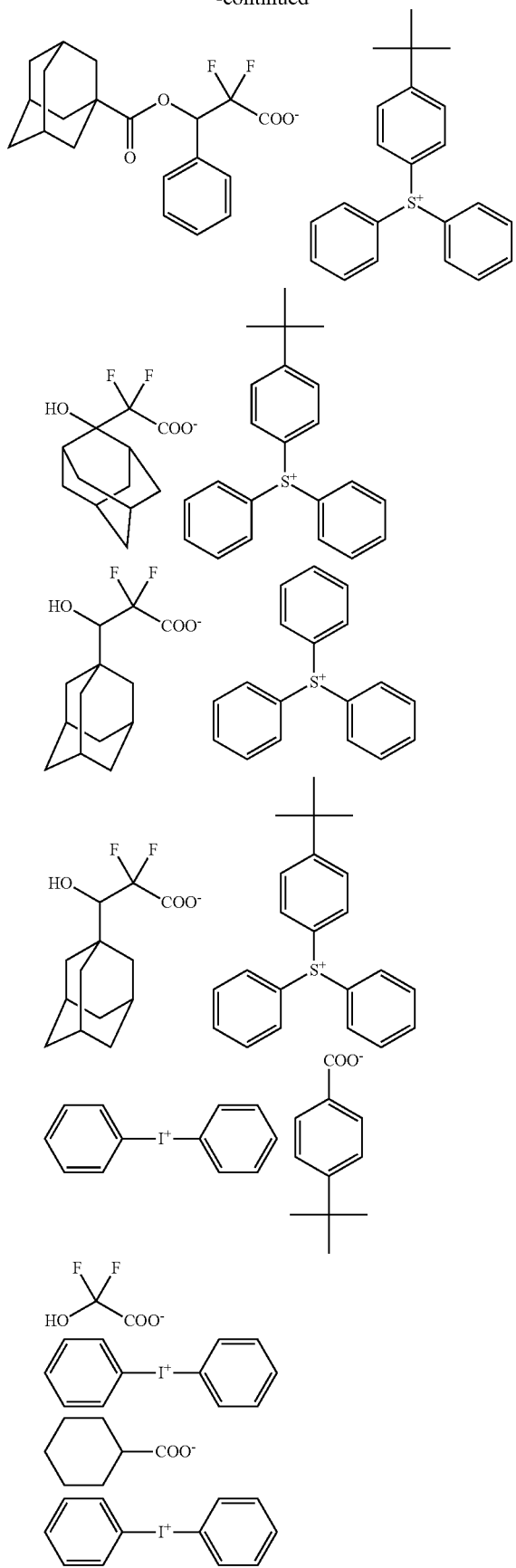

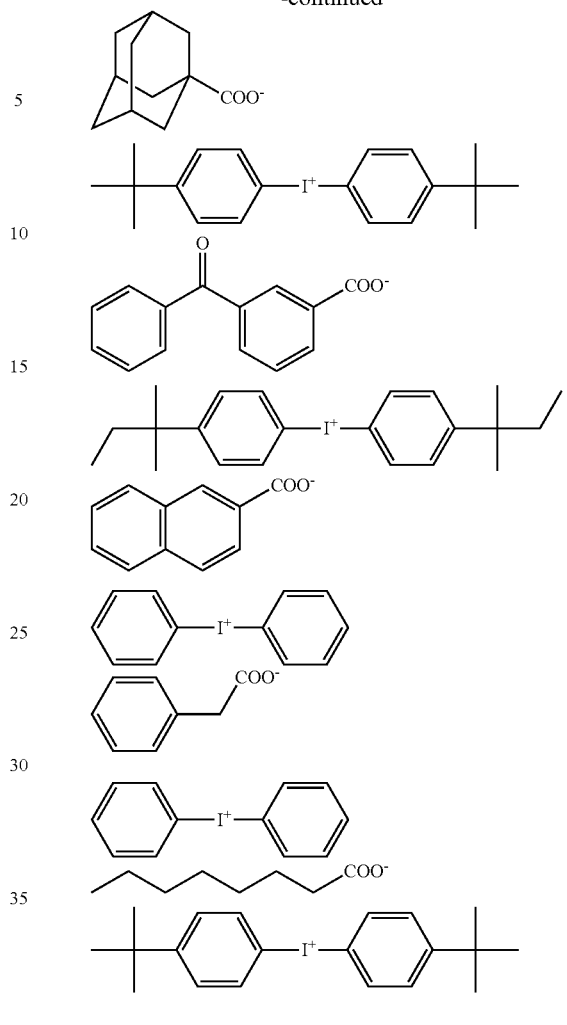

Exemplary surfactants are described in JP-A 2008-111103, paragraphs [0165] to [0166]. Exemplary dissolution regulators are described in JP-A 2008-122932 (US 2008090172), paragraphs [0155] to [0178], and exemplary acetylene alcohols in paragraphs [0179] to [0182].

Notably, an appropriate amount of the organic solvent used is 50 to 10,000 parts, preferably 100 to 5,000 parts by weight, an appropriate amount of the dissolution regulator is 0 to 50 parts, preferably 0 to 40 parts by weight, and an appropriate amount of the basic compound is 0 to 100 parts, preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. This water repellency improver may be used in the topcoatless immersion lithography. These water repellency improvers have a specific structure with a 1,1,1,3,3,3-hexafluoro-2-propanol residue and are described in JP-A 2007-297590, JP-A 2008-111103, JP-A 2008-122932, JP-A 2012-128067, and JP-A 2013-057836.

The water repellency improver is described in more detail. Preferred are a homopolymer consisting of fluorine-containing units of one type, a copolymer consisting of fluorine-containing units of more than one type, and a copolymer consisting of fluorine-containing units and other units. Suitable fluorine-containing units and other units are shown below, but not limited thereto. Notably $R^{55}$ is hydrogen or methyl.
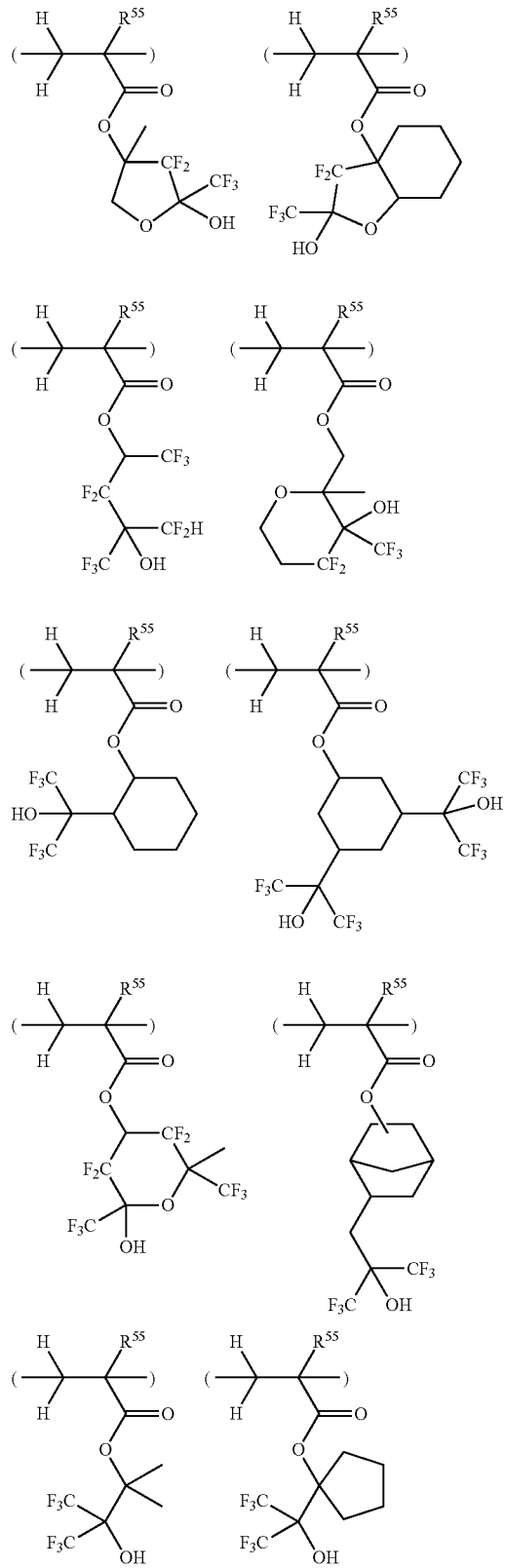
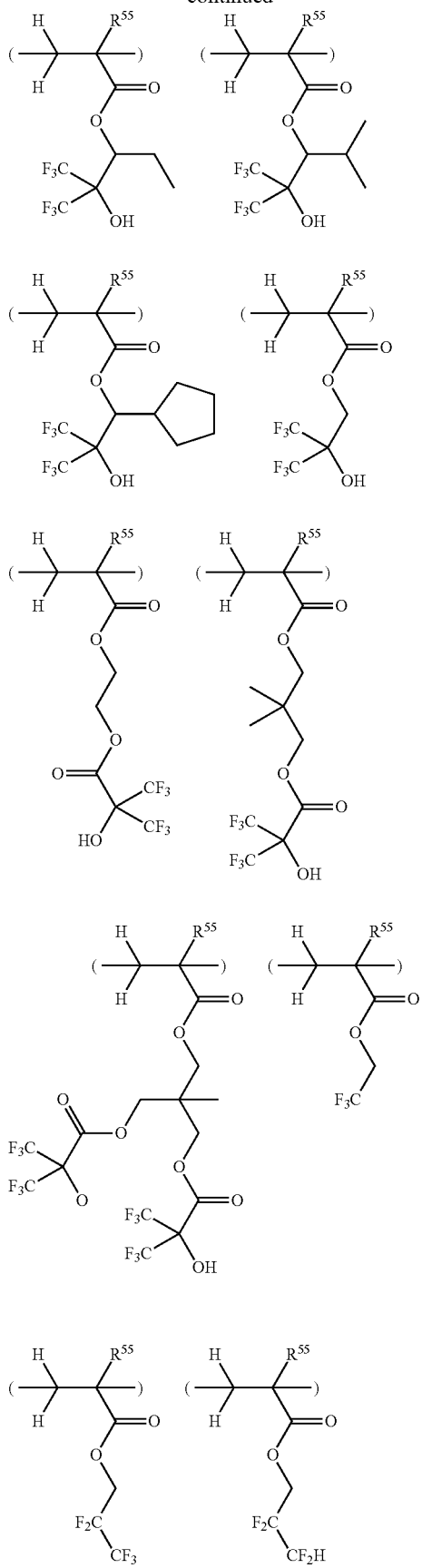

107
-continued
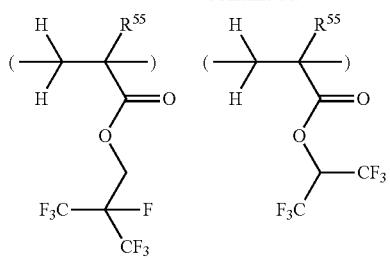
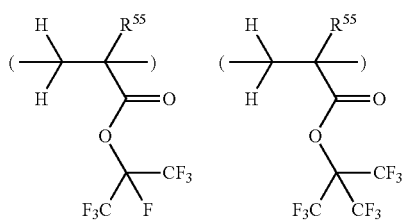
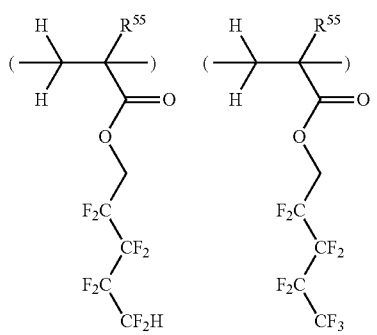
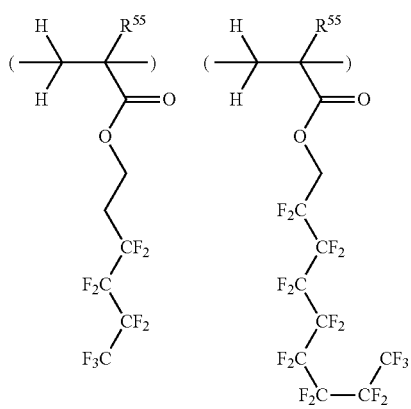
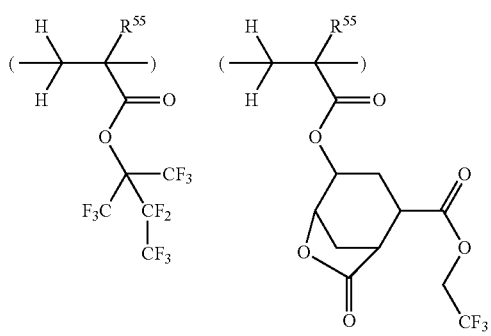
108
-continued
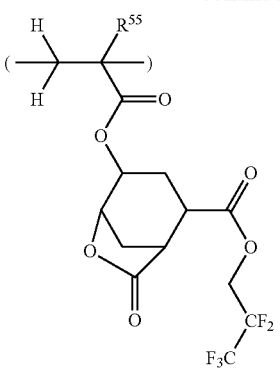
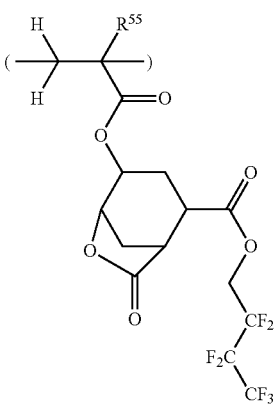
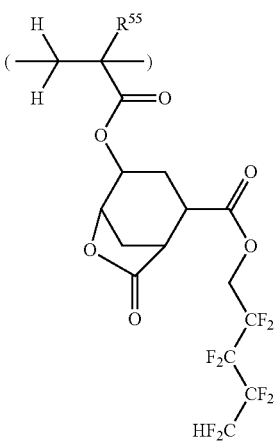
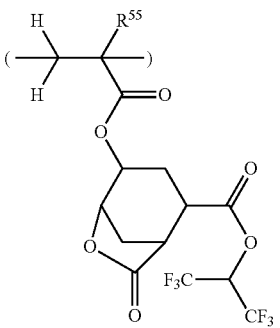

109
-continued
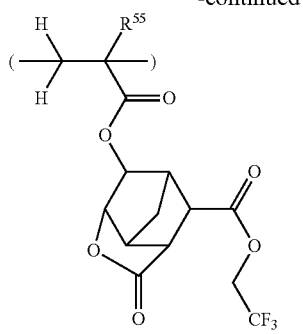
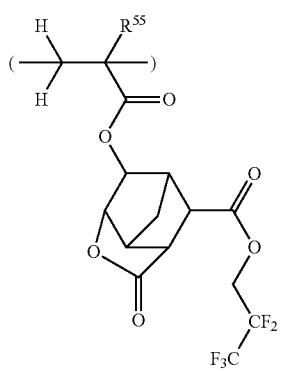
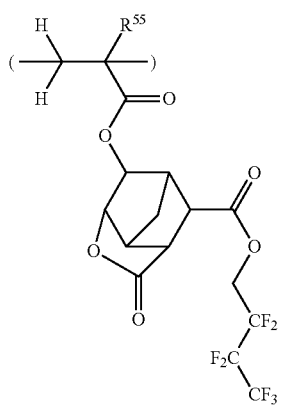
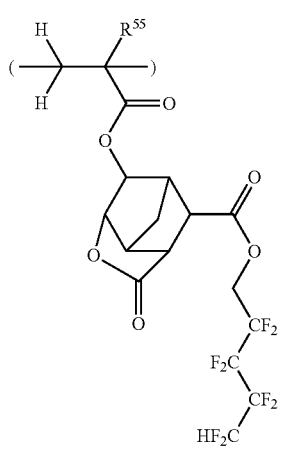
110
-continued
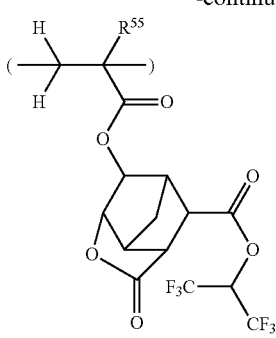
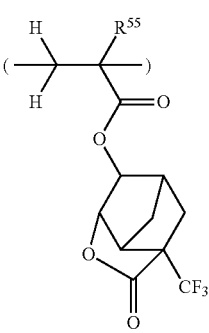
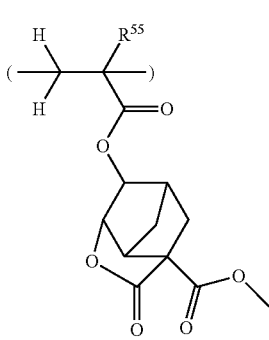
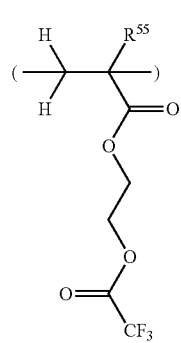
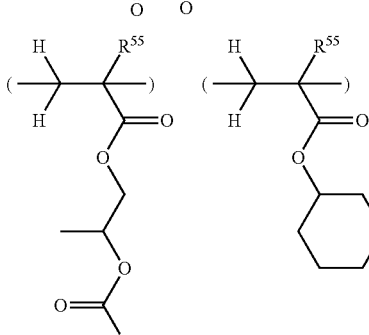
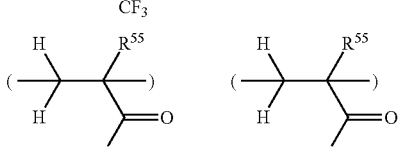
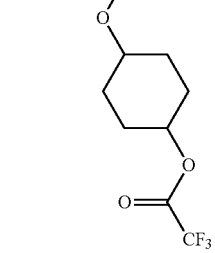
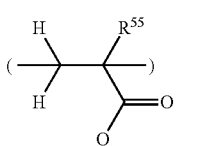
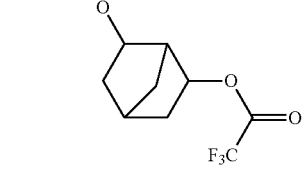

111
-continued
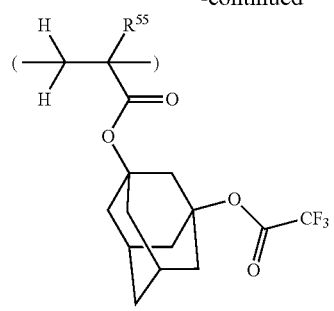
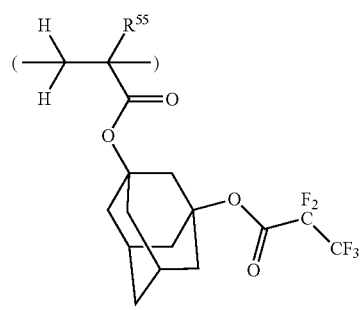
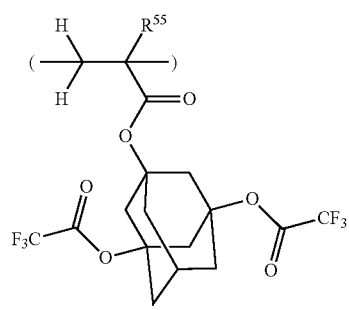
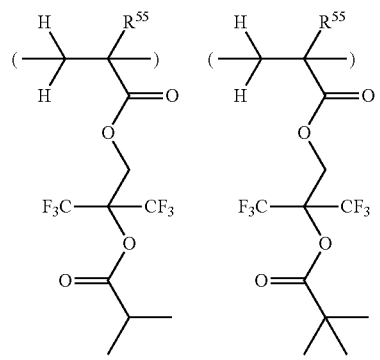
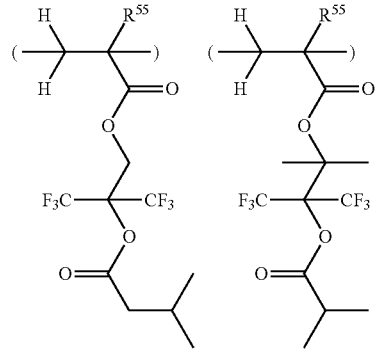
112
-continued
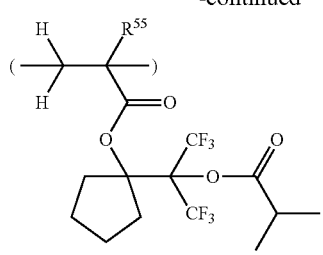
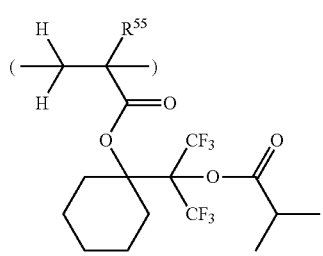
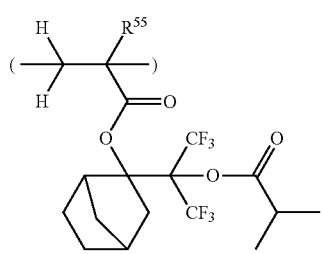
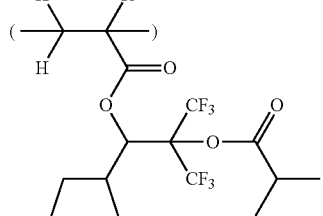
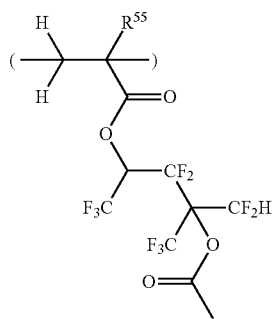
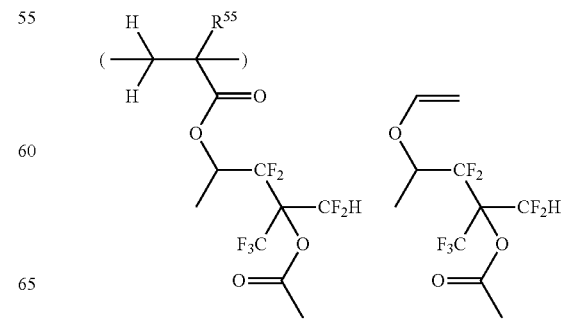

-continued
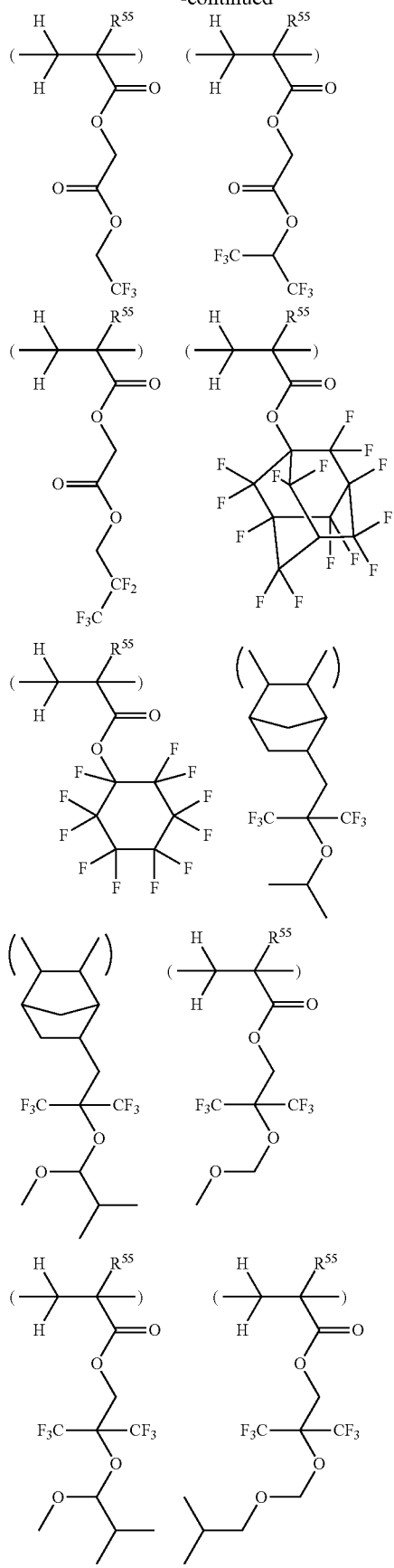
-continued
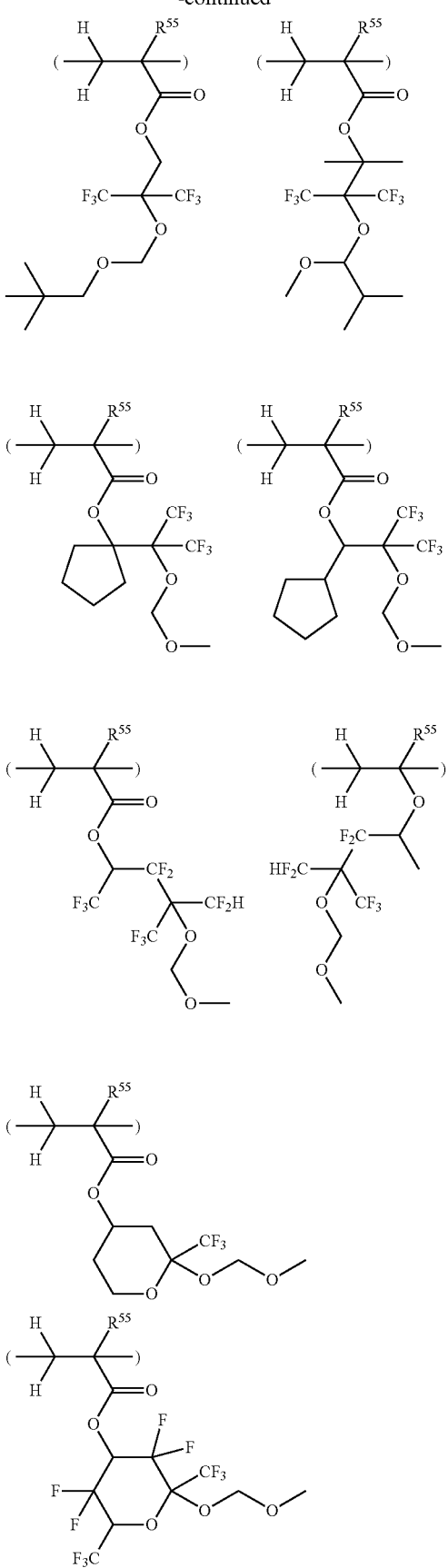

-continued
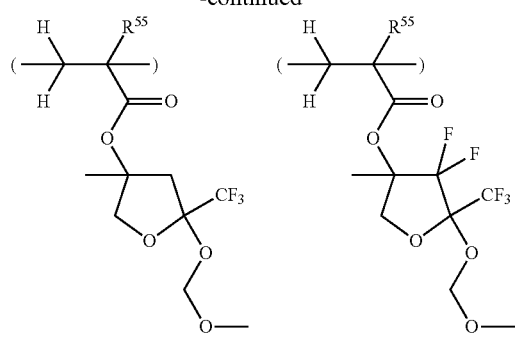
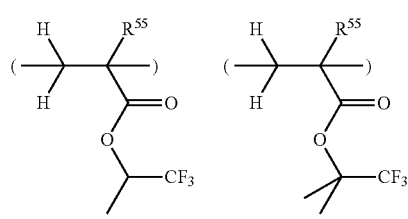
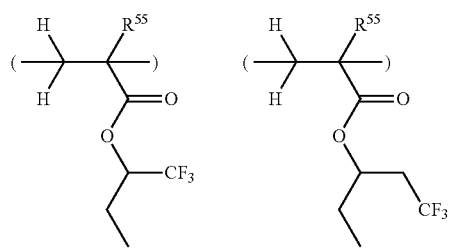
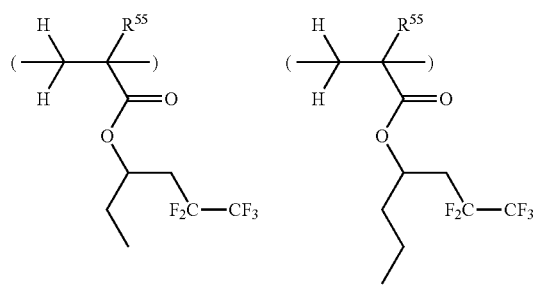
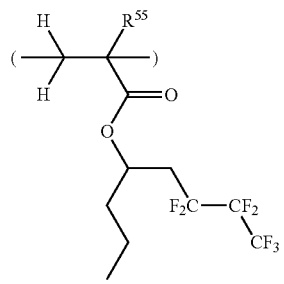
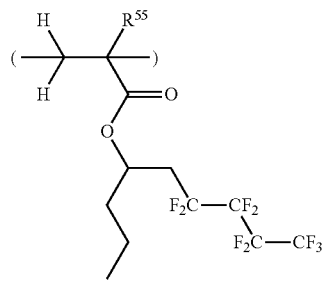
-continued
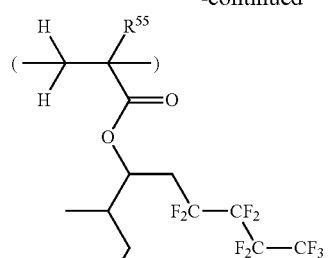
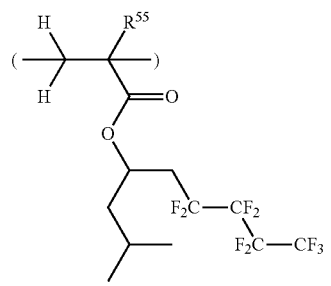
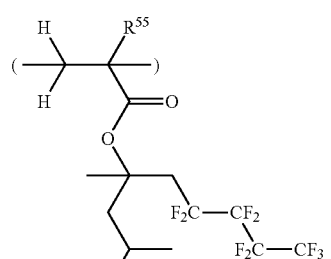
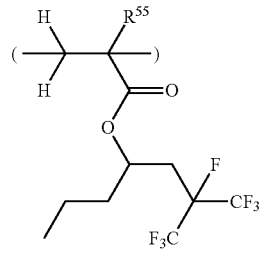
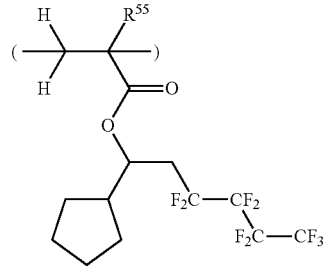
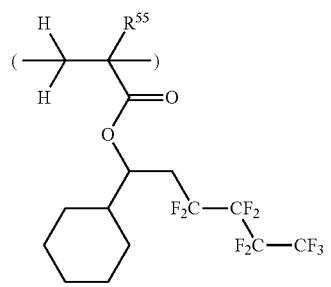

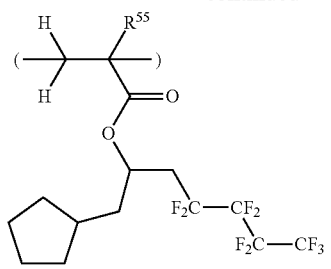
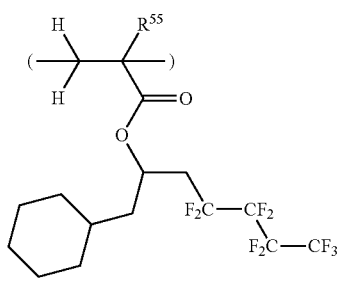
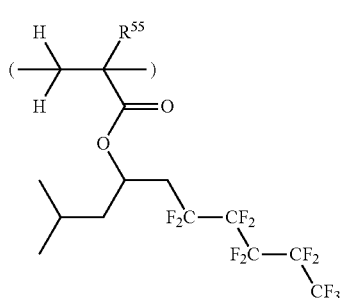
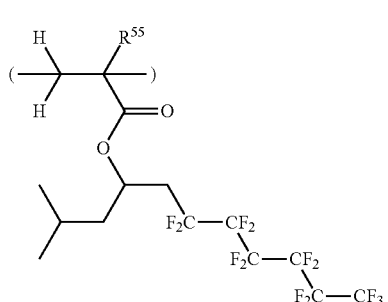
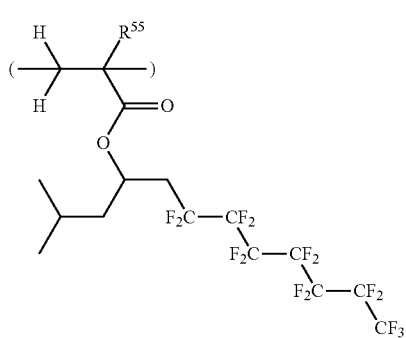
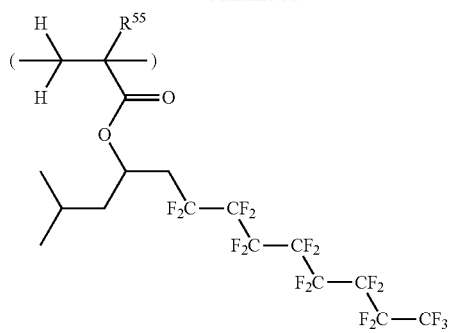
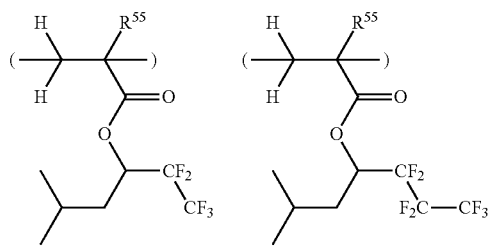
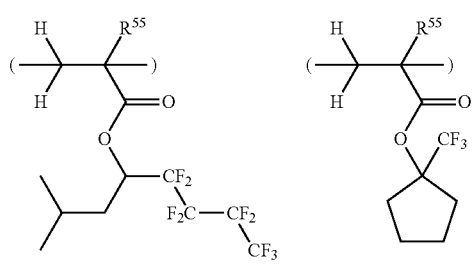
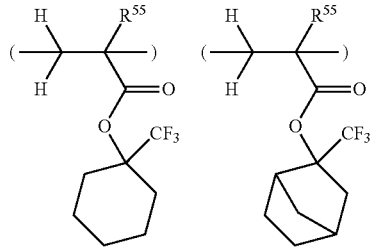
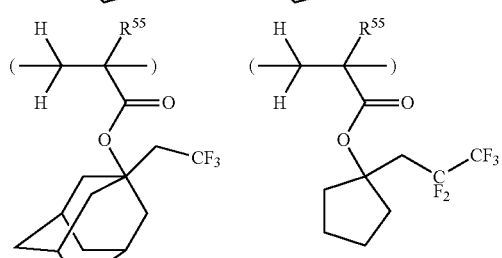
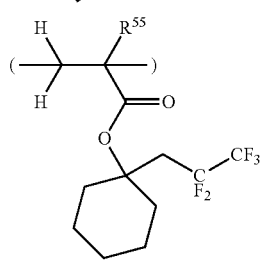

-continued

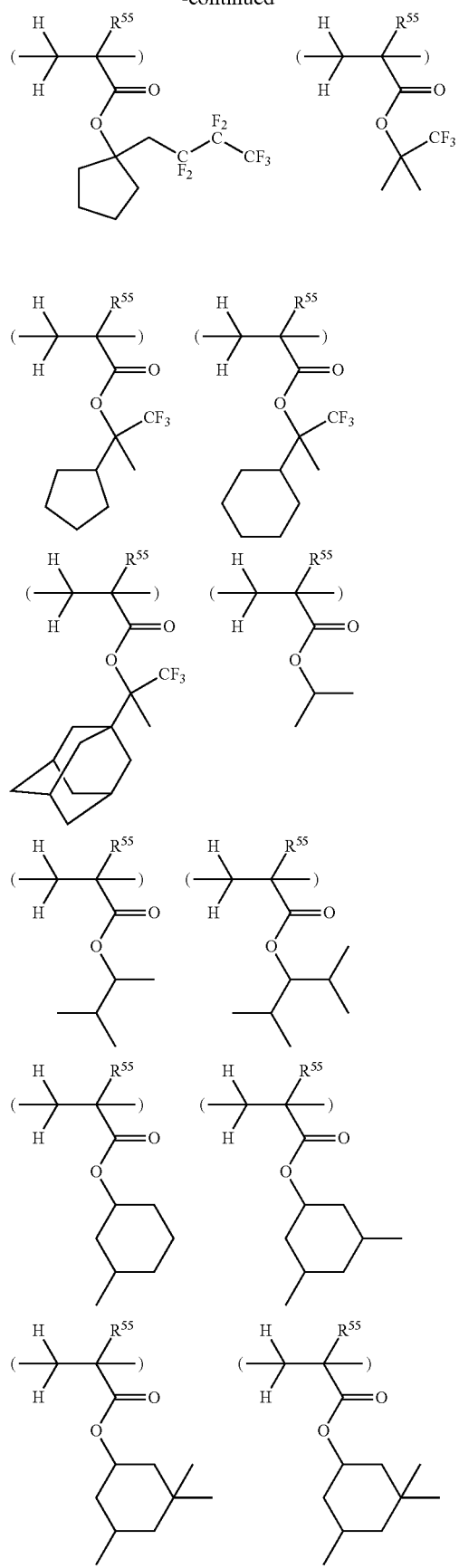

-continued

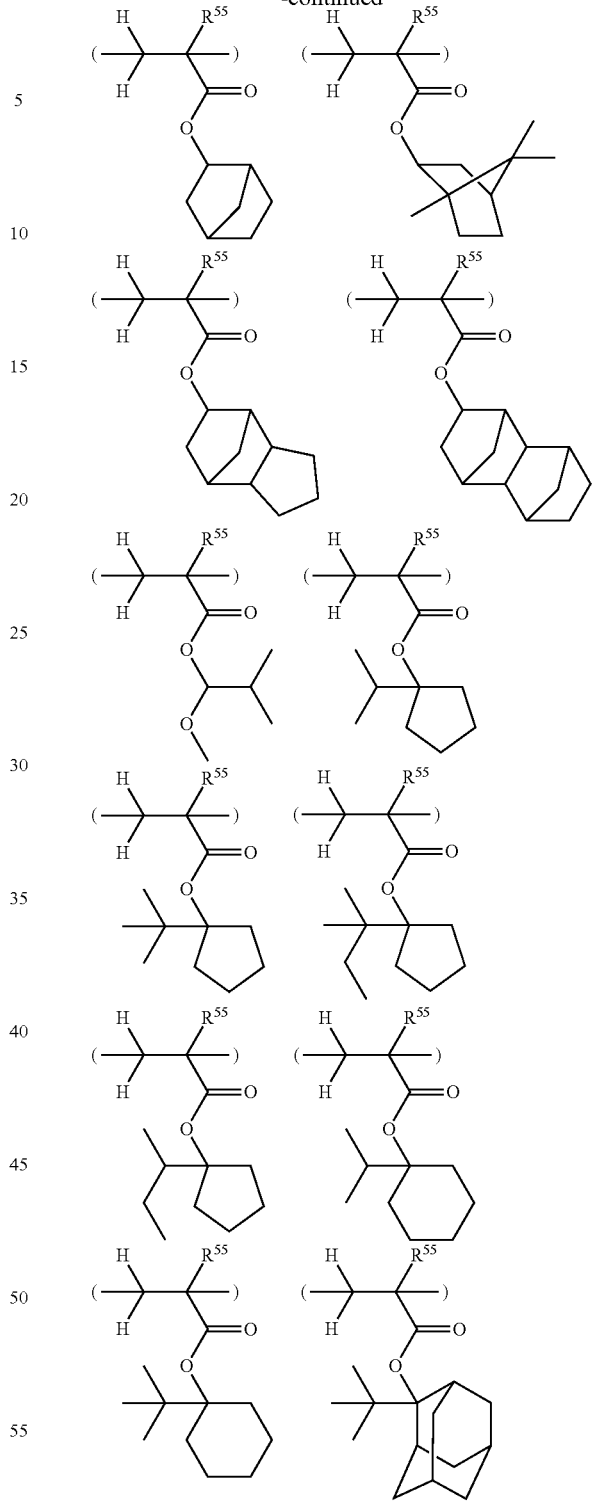

The water repellency improver to be added to the resist composition should be soluble in alkaline aqueous solution as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, any hole pattern opening failure after development, and bridging of a line-and-space pattern. An appropriate amount of the water repellency improver is 0.1 to 20 parts, preferably 0.5 to 10 parts by weight per 100 parts by weight of the base resin.

A crosslinker may be added to the resist composition to facilitate formation of a negative pattern via a polarity switch of the inventive polymer. Suitable crosslinkers are described in JP-A 2006-145755. The crosslinker is preferably used in such an amount as not to interfere with high resolution performance by a polarity switch and solubility change induced by dehydration reaction of the recurring unit derived from the inventive monomer. An appropriate amount of the crosslinker is 1 to 30 parts, preferably 3 to 20 parts by weight per 100 parts by weight of the base resin.

Process

The resist composition comprising the inventive polymer, typically chemically amplified resist composition comprising the inventive polymer, optionally a basic compound and an acid generator, in an organic solvent is used in the fabrication of various integrated circuits. Pattern formation using the resist composition may be performed by well-known lithography processes. The process generally involves coating, prebaking, exposure, PEB, and development. If necessary, any additional steps may be added.

The negative resist composition is first applied onto a substrate on which an integrated circuit is to be formed (e.g., Si, $SiO_2$, SiN, SiON, TiN, WSi, BPSG, SOG, or a multilayer film including silicon-containing antireflective coating or organic hydrocarbon film) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2.0 µm thick.

The resist film is then exposed to a desired pattern of high-energy radiation such as UV, deep-UV, EB, EUV (soft x-ray), x-ray, excimer laser light, γ-ray, or synchrotron radiation, directly or through a mask. The exposure dose is preferably about 1 to 200 mJ/cm$^2$, more preferably about 10 to 100 mJ/cm$^2$, or about 0.1 to 100 µC/cm$^2$, more preferably about 0.5 to 50 µC/cm$^2$. The resist film is further baked (PEB) on a hot plate preferably at 60 to 150° C. for 10 seconds to 30 minutes, more preferably at 80 to 120° C. for 30 seconds to 20 minutes.

Thereafter the resist film is developed in an alkaline developer for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is not dissolved in the developer whereas the resist film in the unexposed region is dissolved. In this way, the desired negative pattern is formed on the substrate. After the development step, the patterned resist film is rinsed with water, preferably for 3 seconds to 3 minutes, more preferably 5 seconds to 2 minutes, by conventional techniques such as dip, puddle and spray techniques. It is appreciated that the resist composition of the invention is best suited for micro-patterning using such high-energy radiation as KrF and ArF excimer laser, EB, EUV (soft x-ray), x-ray, γ-ray and synchrotron radiation.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight. For all polymers, Mw and Mn are determined versus polystyrene standards by GPC using tetrahydrofuran solvent, and dispersity Mw/Mn is computed therefrom.

[1] Synthesis of Monomers

Example 1

Synthesis of Monomer 1

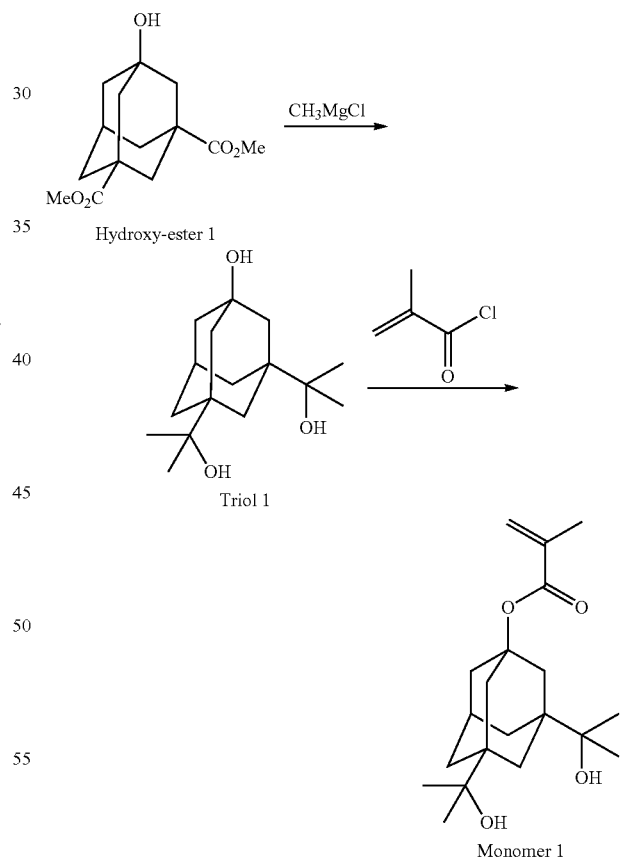

Example 1-1

Synthesis of Triol 1

In nitrogen atmosphere, a solution of 56 g of Hydroxy-ester 1 in 150 mL of THF was added dropwise to 1,080 mL of a THF solution of 1.0 mol/L methylmagnesium chloride at 25-45° C. The contents were stirred at 50° C. for 10 hours. Then the reaction solution was ice cooled, to which a mixture of 108 g of ammonium chloride and 908 g of a 2.4 wt % hydrochloric acid aqueous solution was added dropwise to quench the reaction. This was followed by ordinary aqueous workup, solvent distillation, recrystallization from acetone/diisopropyl ether, filtration, and drying, obtaining 48 g of Triol 1 (yield 85%).

IR (D-ATR): ν=3331, 2972, 2930, 2909, 2855, 1453, 1417, 1380, 1367, 1337, 1327, 1275, 1237, 1208, 1175, 1161, 1138, 1119, 1107, 1055, 1032, 1025, 987, 970, 950, 910, 869, 841, 832, 786, 749, 633, 617, 601, 592 cm$^{-1}$ $^1$H-NMR (600 MHz in DMSO-d$_6$):

δ=1.00 (12H, s), 1.26-1.38 (12H), 2.12 (1H, m), 3.84 (2H, s), 4.19 (1H, s) ppm

Example 1-2

Synthesis of Monomer 1

In nitrogen atmosphere, 23.3 g of methacryloyl chloride was added dropwise to a mixture of 37 g of Triol 1, 30 g of triethylamine, 1.7 g of N,N-dimethylaminopyridine, and 200 mL of acetonitrile at 25-45° C. The contents were stirred at 45° C. for 8 hours. Then the reaction solution was ice cooled, to which 100 mL of a saturated aqueous solution of sodium hydrogencarbonate was added dropwise to quench the reaction. This was followed by ordinary aqueous workup, solvent distillation, recrystallization from acetone/hexane, filtration, and drying, obtaining 37 g of Monomer 1 (yield 80%).

IR (D-ATR): ν=3385, 2974, 2941, 2885, 2869, 1709, 1636, 1558, 1450, 1409, 1377, 1342, 1323, 1304, 1169, 1139, 1116, 1095, 1010, 995, 986, 947, 914, 872, 813, 783, 748, 659, 618, 559 cm$^{-1}$ $^1$H-NMR (600 MHz in DMSO-d):

δ=1.00 (12H, s), 1.30-1.38 (3H), 1.42-1.48 (3H), 1.78 (2H, d), 1.81 (3H, s), 1.89 (2H, d), 1.92 (2H, s), 2.23 (1H, m), 3.99 (2H, s), 5.56 (1H, s), 5.91 (1H, s) ppm Example 2

Synthesis of Monomer 2

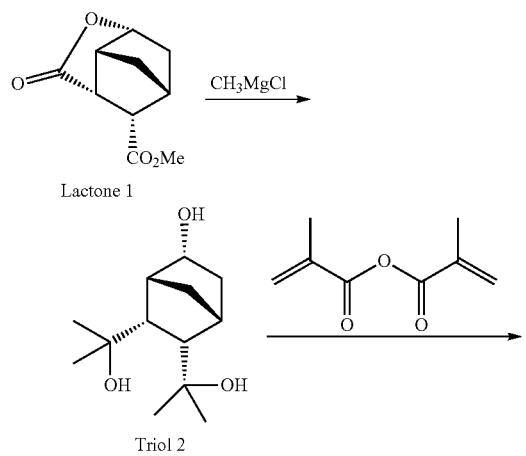

Example 2-1

Synthesis of Triol 2

In nitrogen atmosphere, a solution of 50 g of Lactone 1 in 200 mL of THF was added dropwise to 1,150 mL of a THF solution of 1.0 mol/L methylmagnesium chloride at 25-45° C. The contents were stirred at 50° C. for 10 hours. Then the reaction solution was ice cooled, to which a mixture of 115 g of ammonium chloride and 960 g of a 2.4 wt % hydrochloric acid aqueous solution was added dropwise to quench the reaction. This was followed by ordinary aqueous workup, recrystallization from acetone and diisopropyl ether, filtration, and drying, obtaining 52 g of Triol 2 (yield 90%).

$^1$H-NMR (600 MHz in DMSO-d$_6$):

δ=1.11 (1H, dd), 1.19 (3H, s), 1.28 (1H, m), 1.29 (3H, s), 1.40 (3H, s), 1.50 (3H, s), 1.68-1.76 (2H), 2.09 (1H, d), 2.27-2.35 (2H), 2.44 (1H, m), 3.98 (1H, m), 6.21 (1H, s), 6.37 (1H, d), 7.30 (1H, s) ppm Example 2-2

Synthesis of Monomer 2

In nitrogen atmosphere, 43 g of methacrylic anhydride was added dropwise to a mixture of 45 g of Triol 2, 40 g of triethylamine, 2.4 g of N,N-dimethylaminopyridine, and 200 mL of THF at 25-45° C. The contents were stirred at 45° C. for 10 hours. Then the reaction solution was ice cooled, to which 100 mL of a saturated aqueous solution of sodium hydrogencarbonate was added dropwise to quench the reaction. This was followed by ordinary aqueous workup, solvent distillation, recrystallization from ethyl acetate and hexane, filtration, and drying, obtaining 53 g of Monomer 2 (yield 90%).

IR (D-ATR): ν=3254, 3164, 3022, 2960, 2933, 2883, 1704, 1636, 1498, 1576, 1449, 1412, 1381, 1363, 1328, 1301, 1259, 1202, 1180, 1162, 1135, 1107, 1047, 1018, 953, 934, 862, 850, 835, 814, 776, 733, 627, 570 cm$^{-1}$ $^1$H-NMR (600 MHz in DMSO-d$_6$):

δ=1.12 (3H, s), 1.25 (1H, m), 1.24 (3H, s), 1.30 (1H, m), 1.41 (3H, s), 1.42 (3H, s), 1.68 (1H, m), 1.86 (3H, s), 2.16 (1H, ddd), 2.23 (1H, dd), 2.42 (1H, m), 2.58 (1H, m), 2.63 (1H, m), 4.94 (1H, m), 5.56 (2H, s), 5.81 (1H, s), 6.31 (1H, s) ppm

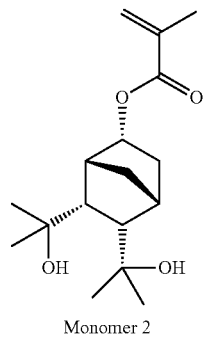

Monomer 2

Example 3

Synthesis of Monomer 3

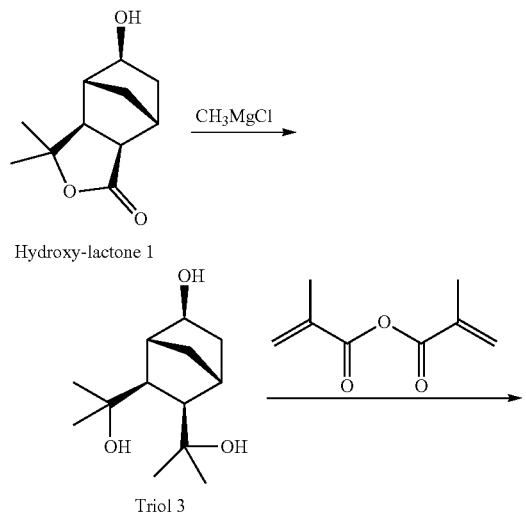

Example 4

Synthesis of Monomer 4

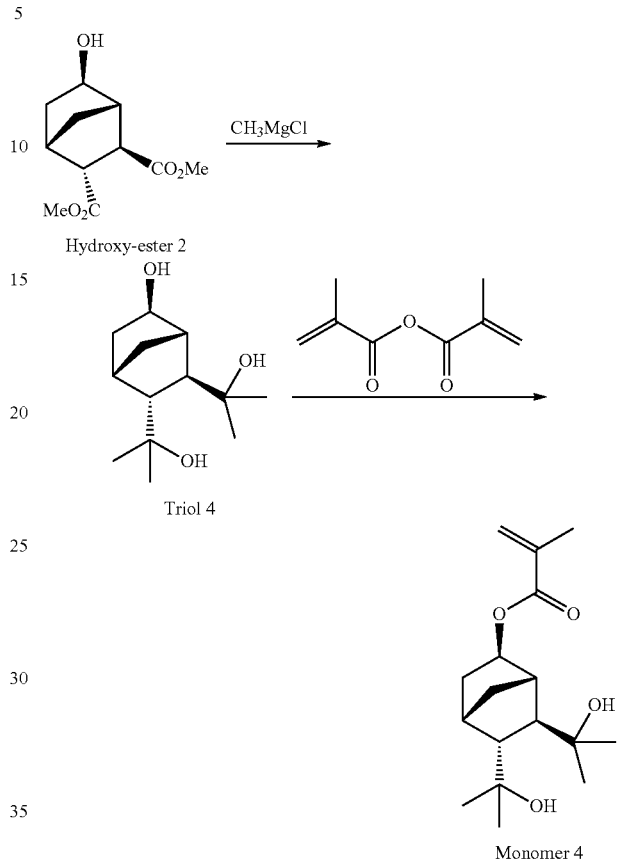

Example 3-1

Synthesis of Triol 3

Triol 3 was synthesized by the same procedure as in Example 2-1 aside from using Hydroxy-lactone 1 as the starting reactant. Just after the workup following reaction, without further purification, Triol 3 was ready for use in the subsequent step.

Example 3-2

Synthesis of Monomer 3

Monomer 3 was synthesized by the same procedure as in Example 2-2 aside from using Triol 3 as the starting reactant. White crystals, two-step yield 72% from Hydroxy-lactone 1.

IR (D-ATR): ν=3160, 3003, 2977, 2920, 2877, 1709, 1639, 1628, 1498, 1466, 1437, 1393, 1381, 1367, 1322, 1248, 1202, 1153, 1051, 1005, 985, 956, 933, 902, 857, 847, 814, 779, 729, 701, 645, 610, 599 cm$^{-1}$ $^1$H-NMR (600 MHz in DMSO-$d_6$):

δ=1.20 (3H, s), 1.21 (6H), 1.22 (3H, s), 1.31 (1H, d), 1.43 (1H, m), 1.47 (1H, d), 1.75 (1H, m), 1.83 (1H, m), 1.84 (3H, s), 1.87 (1H, m), 2.01 (1H, m), 2.05 (11H, d), 4.62 (1H, d), 5.62 (1H, m), 5.97 (1H, m), 6.03 (1H, s), 6.10 (1H, s) ppm

Example 4-1

Synthesis of Triol 3

Triol 4 was synthesized by the same procedure as in Example 2-1 aside from using Hydroxy-ester 2 as the starting reactant. Just after the work-up following reaction, without further purification, Triol 4 was ready for use in the subsequent step.

Example 4-2

Synthesis of Monomer 4

Monomer 4 was synthesized by the same procedure as in Example 2-2 aside from using Triol 4 as the starting reactant. White crystals, two-step yield 70% from Hydroxy-ester 2.

IR (D-ATR): ν=3314, 2973, 2922, 2898, 1709, 1636, 1468, 1446, 1421, 1384, 1371, 1338, 1322, 1300, 1206, 1173, 1159, 1141, 1120, 1055, 1038, 1008, 979, 968, 939, 905, 896, 850, 815, 658, 620, 608 cm$^{-1}$ $^1$H-NMR (600 MHz in DMSO-$d_6$):

δ=1.07 (3H, s), 1.17 (3H, s), 1.19 (3H, s), 1.28 (3H, s), 1.34 (1H, d), 1.38 (1H, d), 1.45 (1H, d), 1.48 (11H, m), 1.73 (1H, m), 1.84 (3H, s), 1.88 (1H, dd), 2.09 (1H, d), 2.29 (1H, d), 5.11 (1H, d), 5.19 (1H, s), 5.29 (1H, s), 5.62 (1H, m), 5.97 (1H, m) ppm

Example 5

Synthesis of Monomer 5

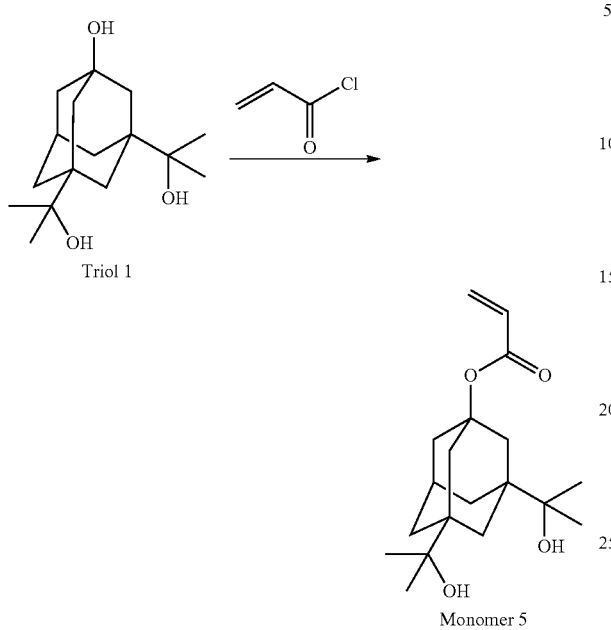

Monomer 5 was synthesized by the same procedure as in Example 1-2 aside from using acryloyl chloride as the starting reactant. White crystals, yield 86%.

Example 6

Synthesis of Monomer 6

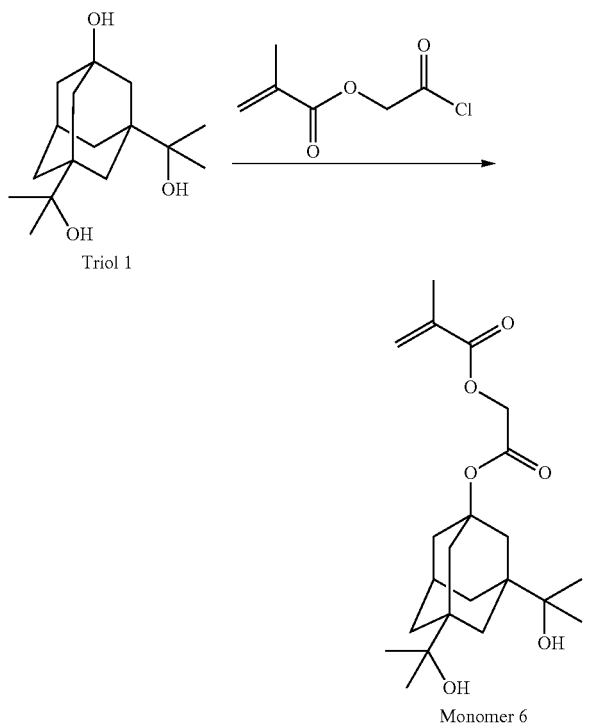

Monomer 6 was synthesized by the same procedure as in Example 1-2 aside from using methacryloyloxyacetyl chloride as the starting reactant. White crystals, yield 76%.

Example 7

Synthesis of Monomer 7

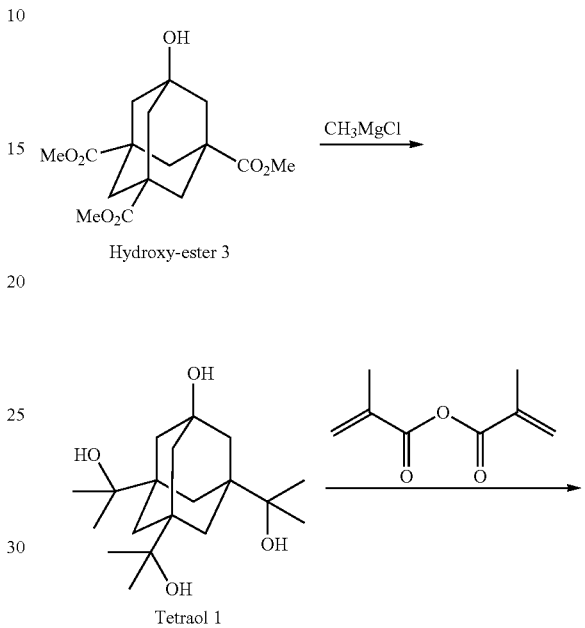

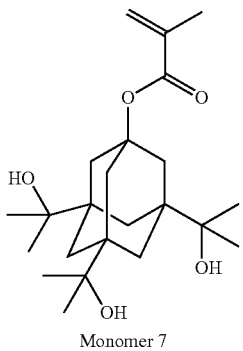

In nitrogen atmosphere, a solution of 61 g of Hydroxy-ester 3 in 500 mL of THF was added dropwise to 1,500 mL of a THF solution of 1.0 mol/L methylmagnesium chloride at 25-45° C. The contents were stirred at 50° C. for 10 hours. Then the reaction solution was ice cooled. In succession, 58 g of methacrylic anhydride was added dropwise to the suspension of alkoxide corresponding to Tetraol 1 below 30° C. The contents were stirred at 25° C. for 4 hours. Then the reaction solution was ice cooled, to which a mixture of 150 g of ammonium chloride and 1,250 g of a 2.4 wt % hydrochloric acid aqueous solution was added dropwise to quench the reaction. This was followed by ordinary aqueous workup, solvent distillation, recrystallization from ethyl acetate/THF/hexane, filtration, and drying, obtaining 37 g of Monomer 7 (two-step yield 51%).

Example 8

Synthesis of Monomer 8

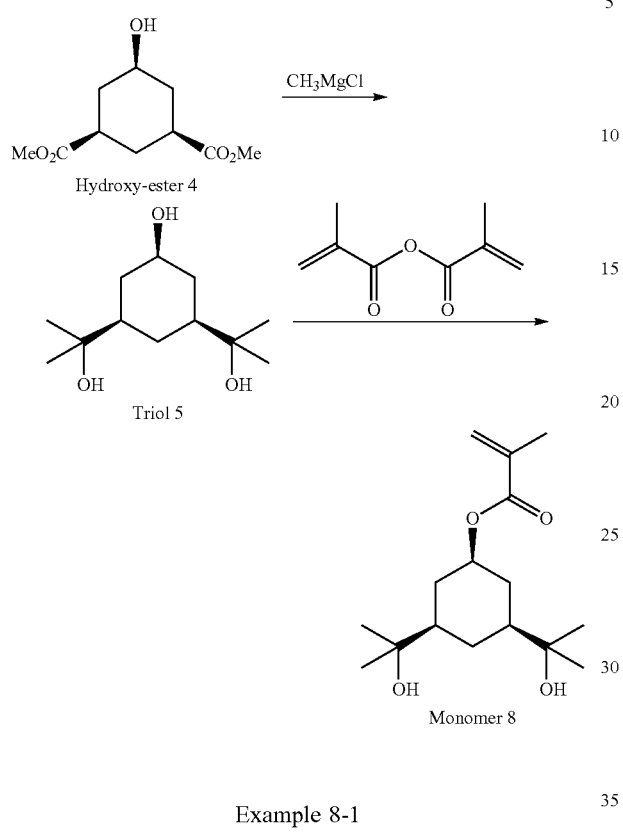

Example 8-1

Synthesis of Triol 5

Triol 5 was synthesized by the same procedure as in Example 2-1 aside from using Hydroxy-ester 4 as the starting reactant. Just after the workup following reaction, without further purification, Triol 5 was ready for use in the subsequent step.

Example 8-2

Synthesis of Monomer 8

Monomer 8 was synthesized by the same procedure as in Example 2-2 aside from using Triol 5 as the starting reactant. White crystals, two-step yield 80% from Hydroxy-ester 4.

IR (D-ATR): ν=3471, 3278, 2969, 2864, 1708, 1639, 1452, 1383, 1317, 1300, 1258, 1219, 1177, 1146, 1120, 1091, 1020, 982, 948, 898, 866, 846, 815, 797, 755, 720, 652, 621, 611, 593, 567, 556 cm$^{-1}$ $^1$H-NMR (600 MHz in DMSO-$d_6$):

δ=0.68 (1H, m), 0.96-1.07 (14H), 1.30 (2H, m), 1.81-1.86 (4H), 2.01 (2H, m), 4.12 (2H, s), 4.66 (1H, m), 5.63 (1H, m), 5.99 (1H, m) ppm

[2] Synthesis of Polymers

Examples 9 to 27 & Comparative Examples 1 to 9

Each of polymers (Polymers 1 to 19 and Comparative Polymers 1 to 9) for use in resist compositions was prepared by combining monomers in cyclopentanone solvent, effecting copolymerization reaction, crystallizing from hexane, washing with hexane several times, isolation and drying. The polymer was analyzed for composition by $^1$H-NMR and $^{13}$C-NMR spectroscopy.

Example 9

Polymer 1

Mw=8,500

Mw/Mn=1.67

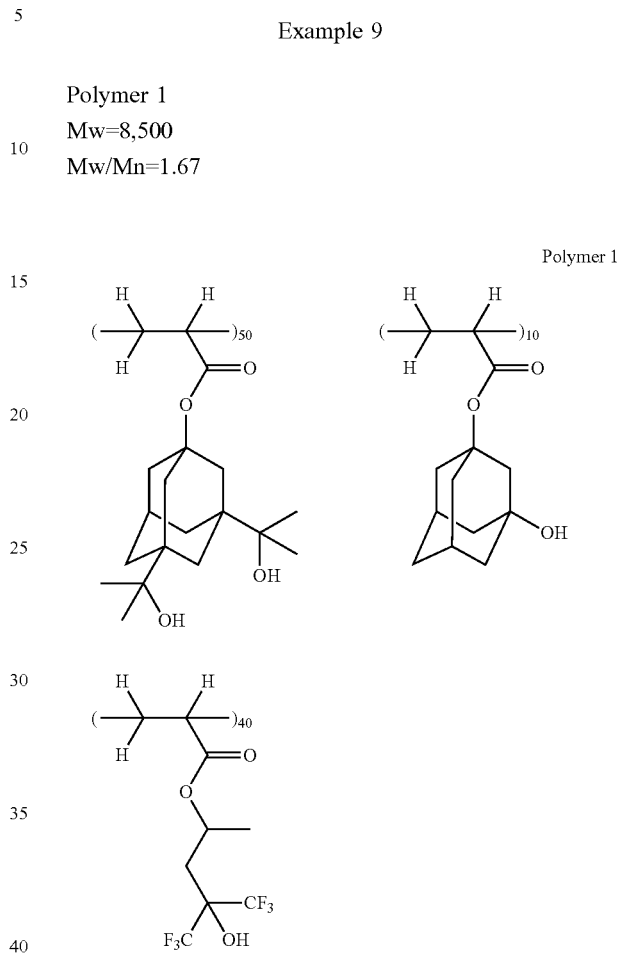

Example 10

Polymer 2

Mw=8,400

Mw/Mn=1.65

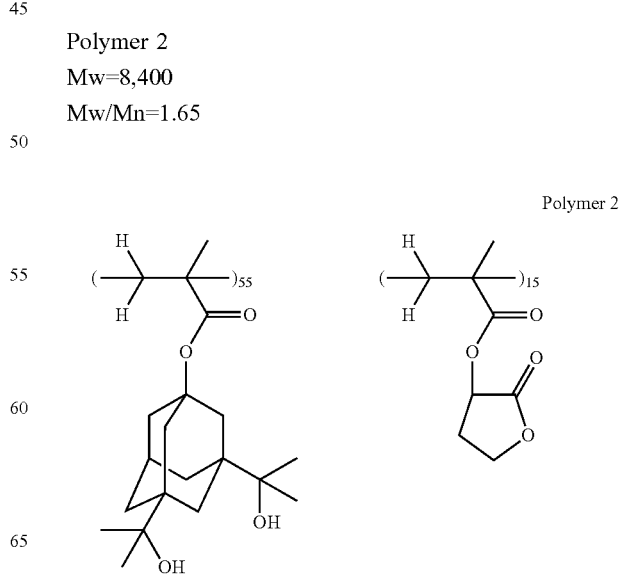

-continued
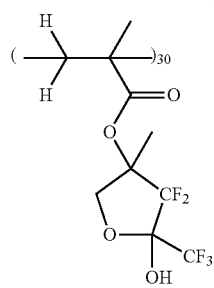
Example 11
Polymer 3
Mw=8,300
Mw/Mn=1.67
Polymer 3
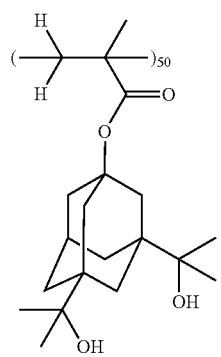 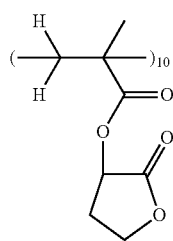
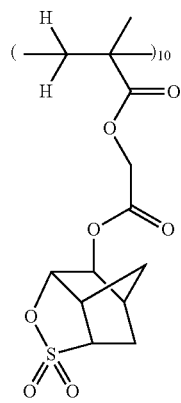 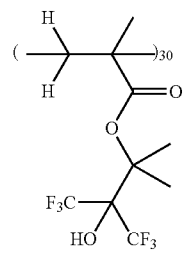
Example 12
Polymer 4
Mw=8,300
Mw/Mn=1.66
Polymer 4
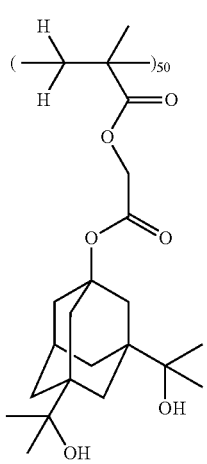 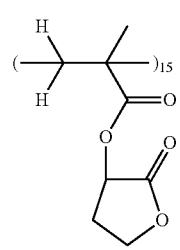
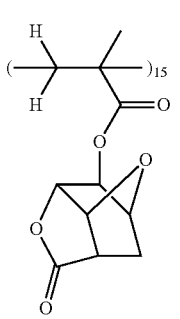 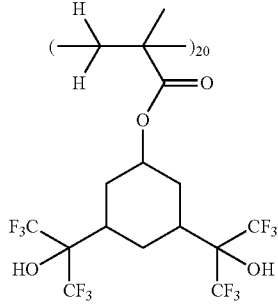
Example 13
Polymer 5
Mw=8,500
Mw/Mn=1.66
Polymer 5
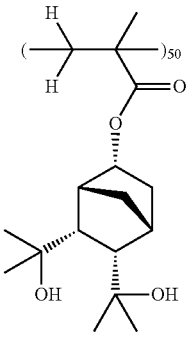 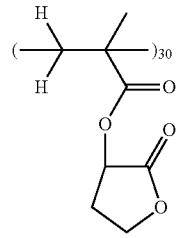

-continued
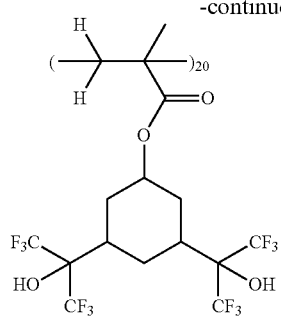
Example 14
Polymer 6
Mw=8,600
Mw/Mn=1.61
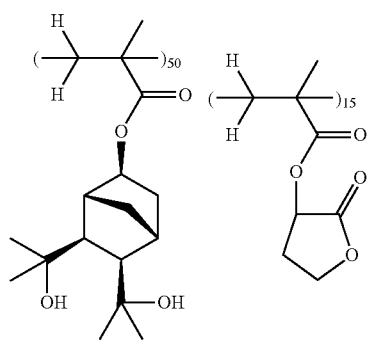
Example 15
Polymer 7
Mw=8,400
Mw/Mn=1.67
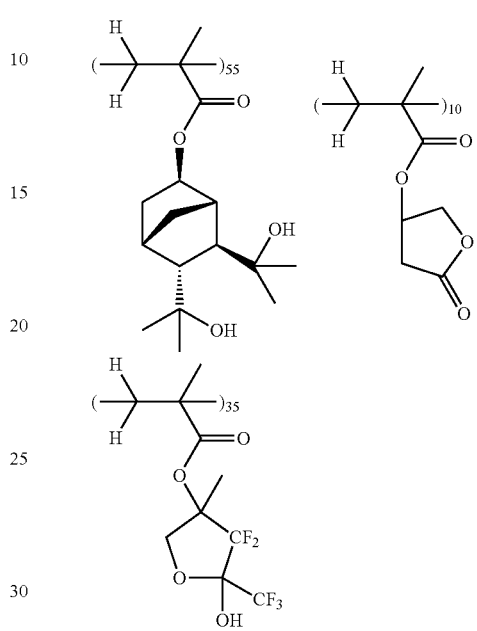
Polymer 7
Polymer 6
Example 16
Polymer 8
Mw=8,500
Mw/Mn=1.62
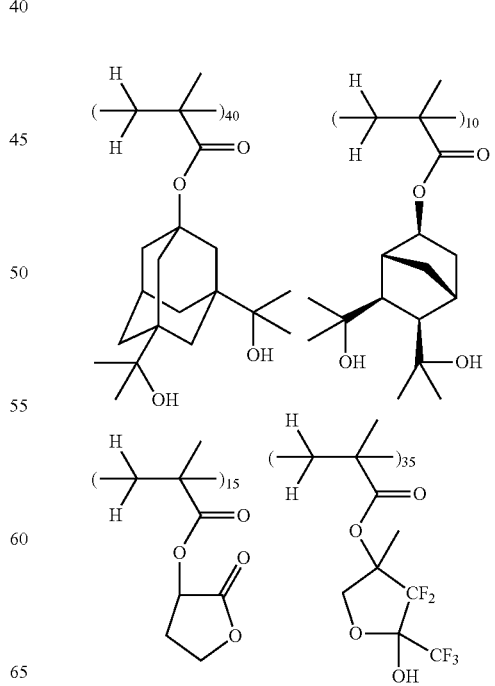
Polymer 8

Example 17
Polymer 9
Mw=8,500
Mw/Mn=1.64
Polymer 9
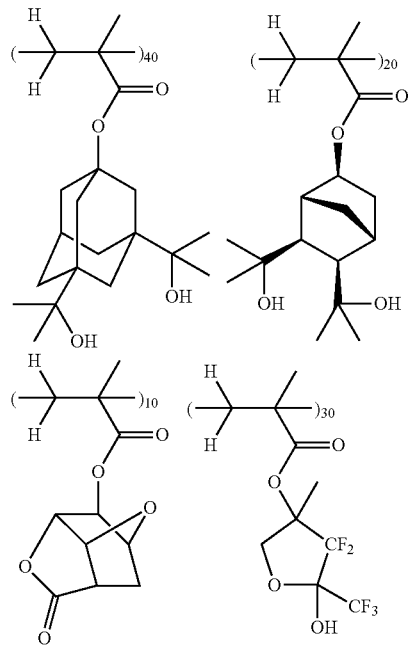
Example 18
Polymer 10
Mw=8,600
Mw/Mn=1.62
Polymer 10
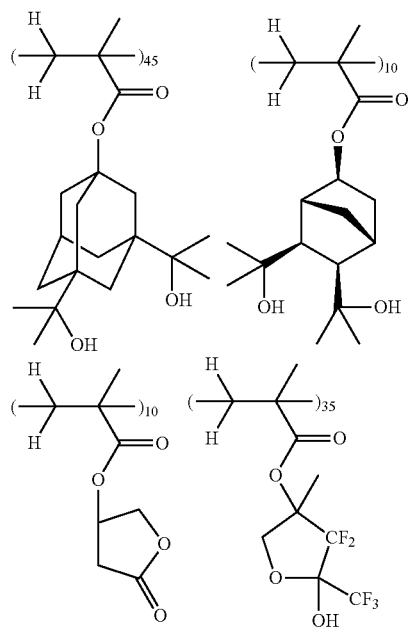
Example 19
Polymer 11
Mw=8,300
Mw/Mn=1.61
Polymer 11
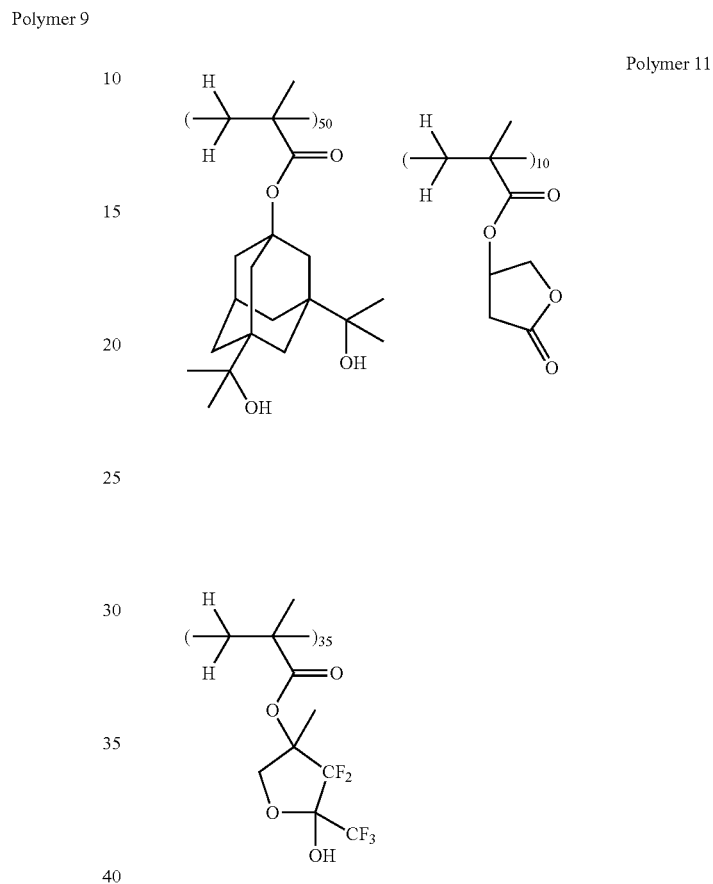
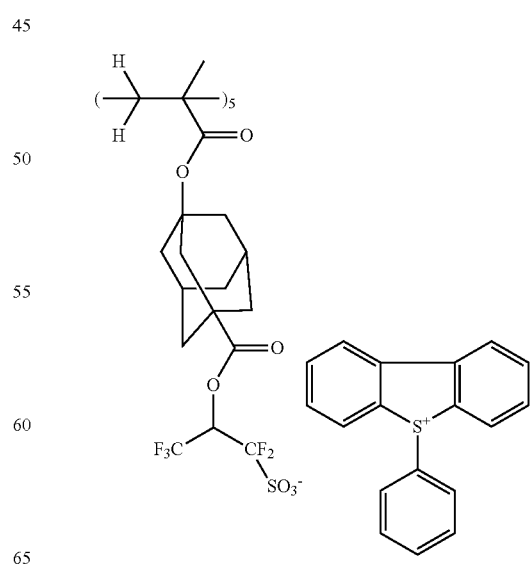

Example 20
Polymer 12
Mw=8,500
Mw/Mn=1.63
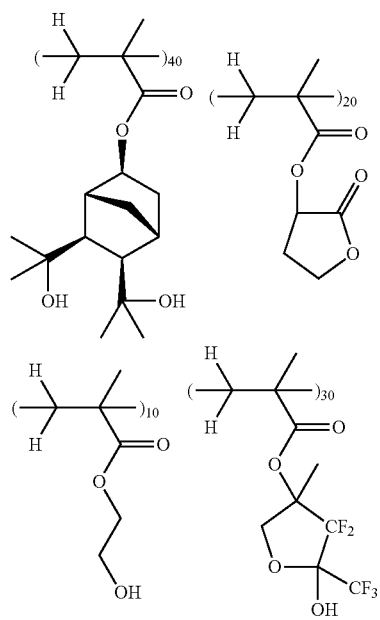
Polymer 12
Example 21
Polymer 13
Mw=8,300
Mw/Mn=1.62
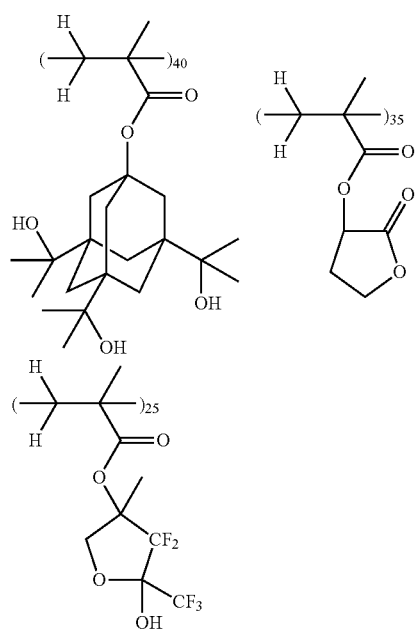
Polymer 13
Example 22
Polymer 14
Mw=8,300
Mw/Mn=1.62
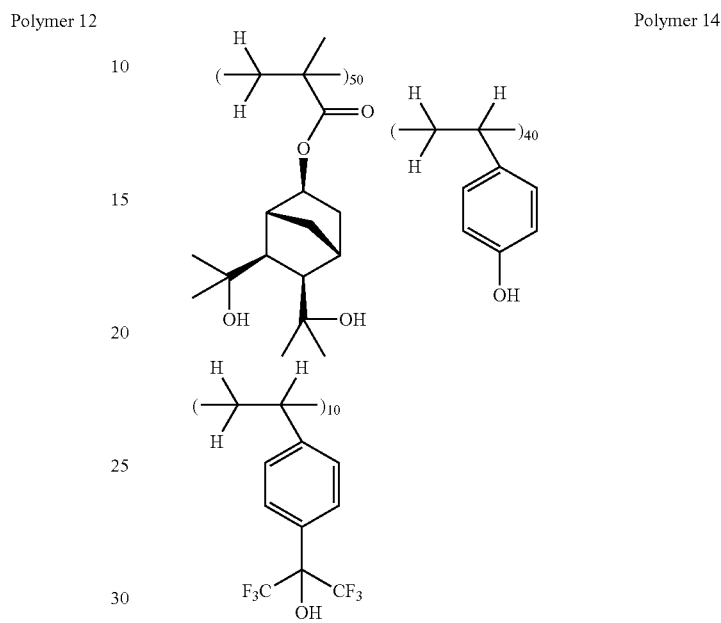
Polymer 14
Example 23
Polymer 15
Mw=8,500
Mw/Mn=1.60
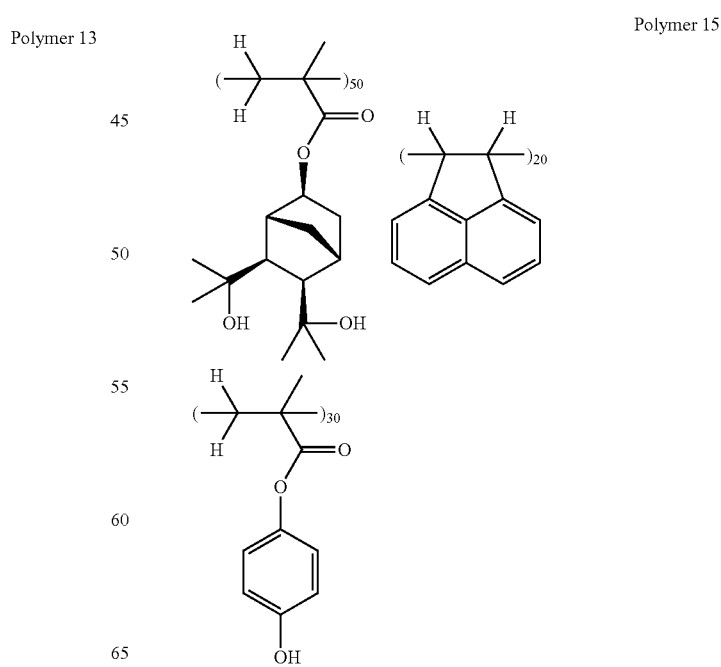
Polymer 15

Example 24
Polymer 16
Mw=8,100
Mw/Mn=1.65
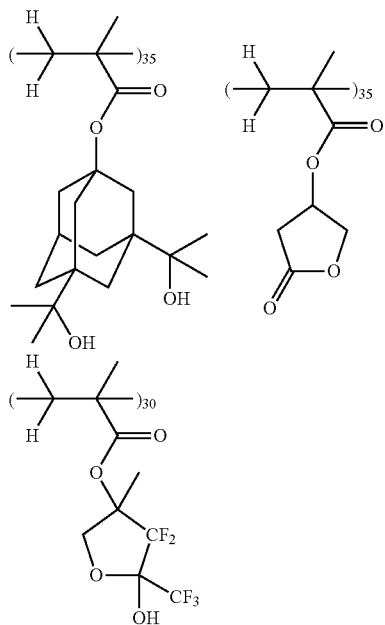
Polymer 16
Example 25
Polymer 17
Mw=8,000
Mw/Mn=1.63
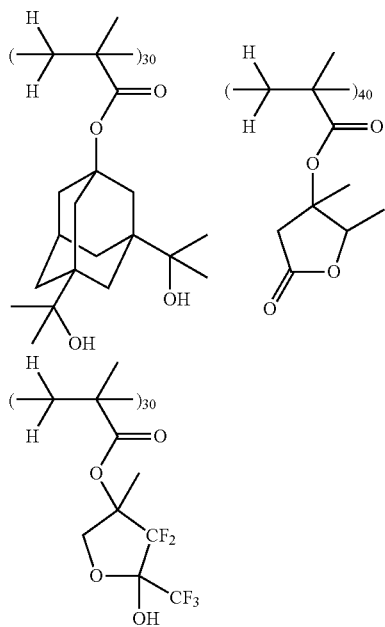
Polymer 17
Example 26
Polymer 18
Mw=8,200
Mw/Mn=1.64
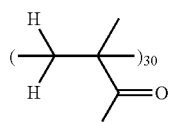
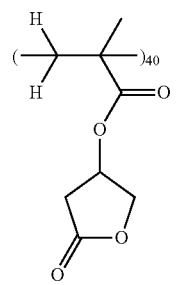
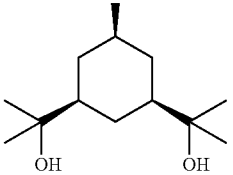
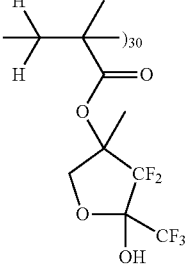
Polymer 18
Example 27
Polymer 19
MW=8,100
Mw/Mn=1.63
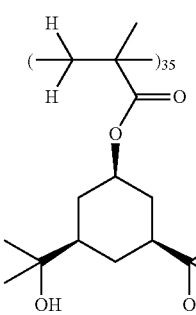
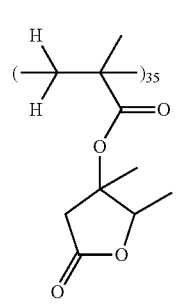
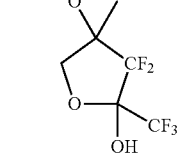
Polymer 19

141

Comparative Example 1

Comparative Polymer 1
Mw=8,400
Mw/Mn=1.65

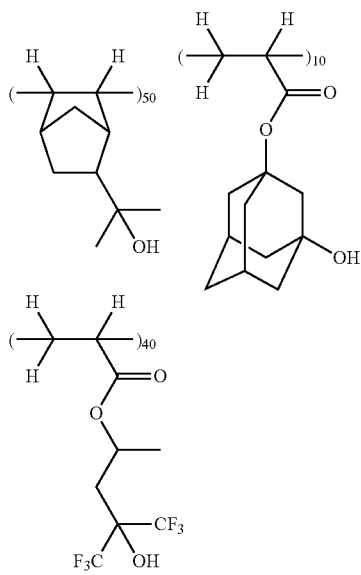

Comparative Polymer 1

Comparative Example 2

Comparative Polymer 2
Mw=8,500
Mw/Mn=1.63

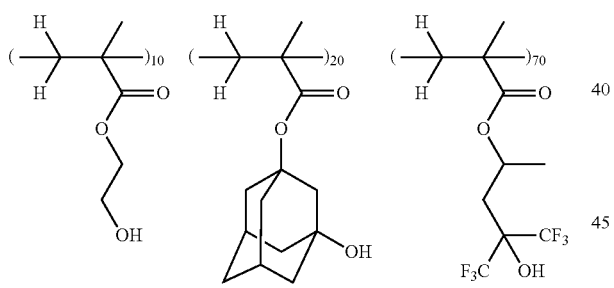

Comparitive Polymer 2

142

Comparative Example 3

Comparative Polymer 3
Mw=8,700
Mw/Mn=1.65

Comparitive Polymer 3

Comparative Example 4

Comparative Polymer 4
Mw=8,600
Mw/Mn=1.62

Comparitive Polymer 4

Comparative Example 5

Comparative Polymer 5
Mw=8,400
Mw/Mn=1.66

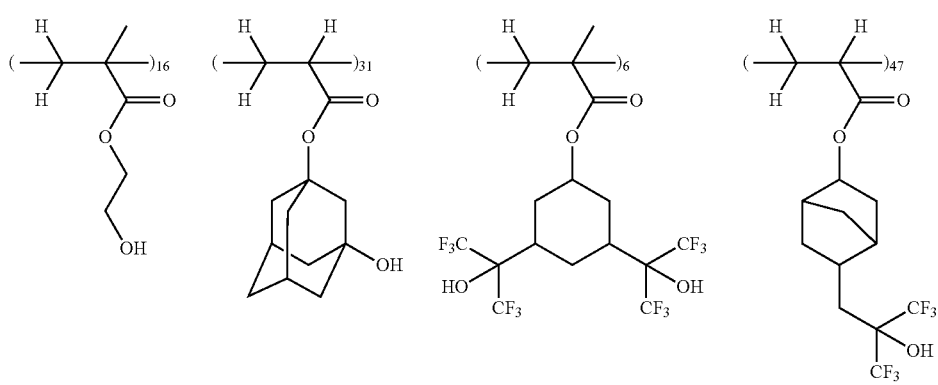

Comparitive Polymer 5

Comparative Example 6

Comparative Polymer 6
Mw=8,600
Mw/Mn=1.63

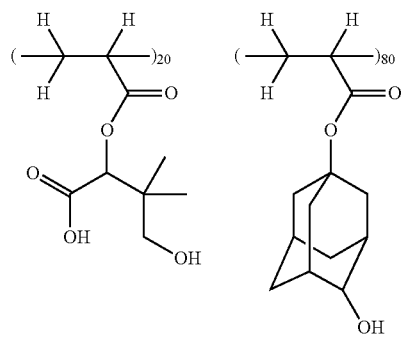

Comparitive Polymer 6

Comparative Example 7

Comparative Polymer 7
Mw=8,600
Mw/Mn=1.63

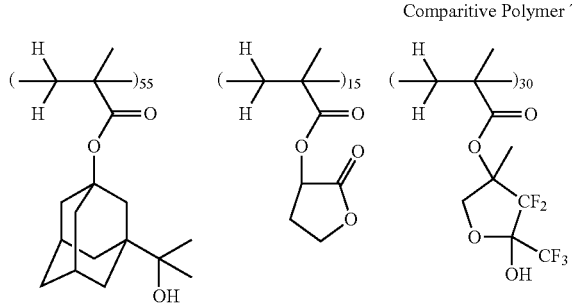

Comparitive Polymer 7

Comparative Example 8

Comparative Polymer 8
Mw=8,500
Mw/Mn=1.61

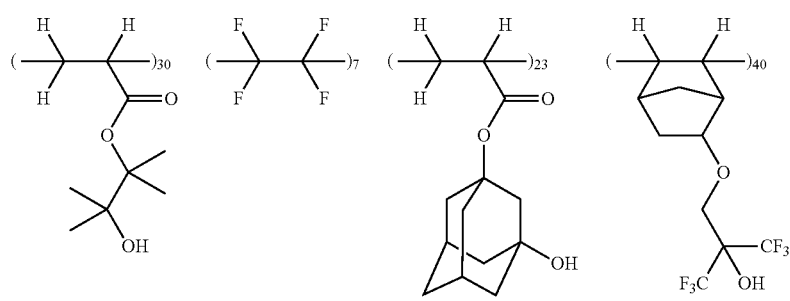

Comparitive Polymer 8

Comparative Example 9

Comparative Polymer 9
Mw=8,400
Mw/Mn=1.65

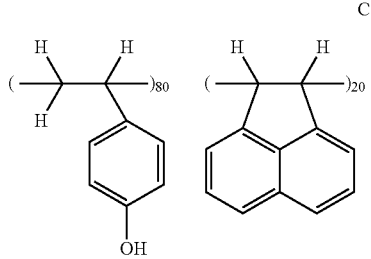

Comparative Polymer 9

[3] Preparation of Resist Compositions

Examples 28 to 46 & Comparative Examples 10 to 18

Resist compositions R-01 to R-28 were prepared by using inventive Polymers 1 to 19 or Comparative Polymers 1 to 9 as the base resin, dissolving the polymer and other components in a solvent in accordance with the recipe shown in Tables 1 and 2, and filtering through a Teflon® filter having a pore size of 0.2 µm.

In Tables 1 and 2, acid generator (PAG-1 to 4), water-repellent polymer (SF-1), sensitivity regulator (Q-1 to 4), crosslinker (XL-1), and solvent are as identified below.

Photoacid Generator: PAG-1 to PAG-4

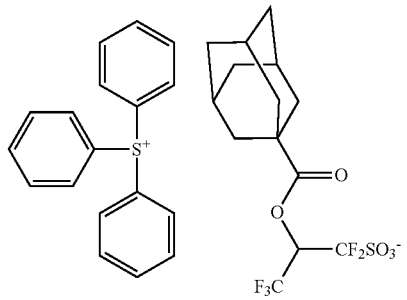

PAG-1

PAG-2
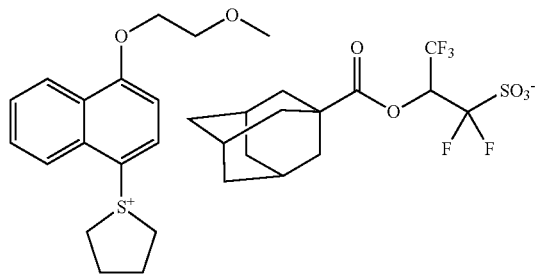
PAG-3
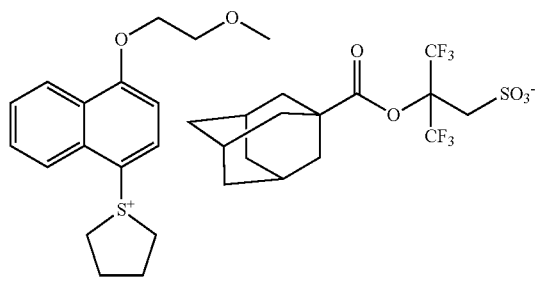
PAG-4
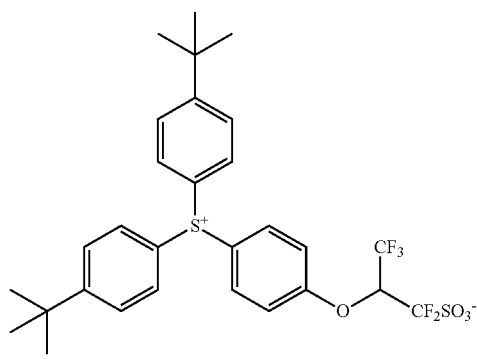
Sensitivity Regulator: Q-1 to Q-4
Q-1
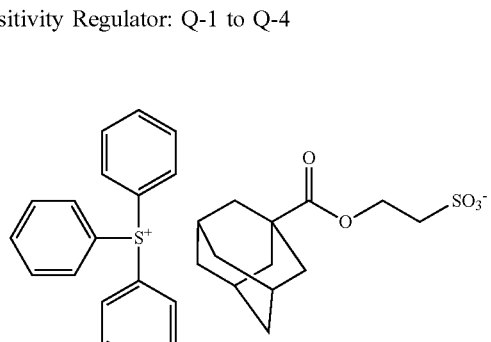
Q-2
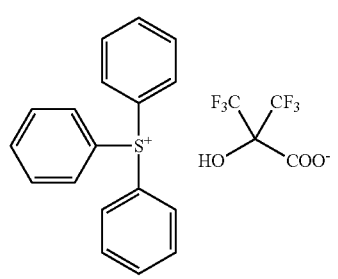
Q-3
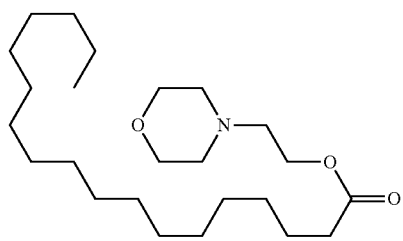
Q-4
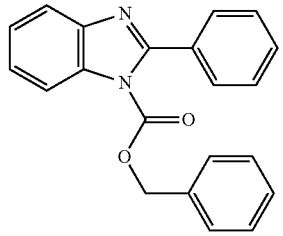
Water-Repellent Polymer: SF-1
Mw=8,700
Mw/Mn=1.85
SF-1
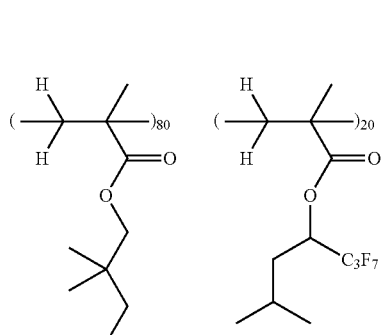
Crosslinker: XL-1
XL-1
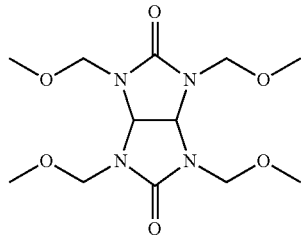
PGEE: Propylene Glycol Monoethyl Ether
GBL: γ-butyrolactone

TABLE 1

| | | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| Example | 28 | R-01 | Polymer 1 (100) | PAG-1 (6.0) | Q-3 (8.0) | SF-1 (5.0) | — | PGEE (2000) GBL (500) |
| | 29 | R-02 | Polymer 2 (100) | PAG-1 (6.0) | Q-1 (3.5) | SF-1 (5.0) | — | PGEE (2000) GBL (500) |
| | 30 | R-03 | Polymer 3 (100) | PAG-2 (6.0) | Q-4 (8.0) | SF-1 (5.0) | — | PGEE (2000) GBL (500) |
| | 31 | R-04 | Polymer 4 (100) | PAG-3 (6.0) | Q-4 (8.0) | SF-1 (5.0) | — | PGEE (2000) GBL (500) |
| | 32 | R-05 | Polymer 5 (100) | PAG-4 (6.0) | Q-3 (8.0) | SF-1 (5.0) | — | PGEE (2000) GBL (500) |
| | 33 | R-06 | Polymer 6 (100) | PAG-1 (6.0) | Q-2 (3.0) | SF-1 (5.0) | — | PGEE (2000) GBL (500) |
| | 34 | R-07 | Polymer 7 (100) | PAG-1 (6.0) | Q-1 (3.5) | SF-1 (5.0) | — | PGEE (2000) GBL (500) |
| | 35 | R-08 | Polymer 8 (100) | PAG-1 (6.0) | Q-2 (3.0) | SF-1 (5.0) | — | PGEE (2000) GBL (500) |
| | 36 | R-09 | Polymer 9 (100) | PAG-1 (6.0) | Q-3 (8.0) | SF-1 (5.0) | — | PGEE (2000) GBL (500) |
| | 37 | R-10 | Polymer 10 (100) | PAG-4 (6.0) | Q-4 (8.0) | SF-1 (5.0) | — | PGEE (2000) GBL (500) |
| | 38 | R-11 | Polymer 11 (100) | — | Q-4 (8.0) | SF-1 (5.0) | — | PGEE (2000) GBL (500) |
| | 39 | R-12 | Polymer 12 (100) | PAG-1 (6.0) | Q-3 (8.0) | SF-1 (5.0) | XL-1 (5.0) | PGEE (2000) GBL (500) |
| | 40 | R-13 | Polymer 13 (100) | PAG-1 (6.0) | Q-1 (3.5) | SF-1 (5.0) | — | PGEE (2000) GBL (500) |
| | 41 | R-14 | Polymer 14 (100) | PAG-1 (6.0) | Q-3 (8.0) | SF-1 (5.0) | — | PGEE (2000) GBL (500) |
| | 42 | R-15 | Polymer 15 (100) | PAG-1 (6.0) | Q-3 (8.0) | SF-1 (5.0) | — | PGEE (2000) GBL (500) |
| | 43 | R-16 | Polymer 16 (100) | PAG-1 (6.0) | Q-3 (8.0) | SF-1 (5.0) | — | PGEE (2000) GBL (500) |
| | 44 | R-17 | Polymer 17 (100) | PAG-4 (6.0) | Q-2 (8.0) | SF-1 (5.0) | — | PGEE (2000) GBL (500) |
| | 45 | R-18 | Polymer 18 (100) | PAG-1 (6.0) | Q-3 (8.0) | SF-1 (5.0) | — | PGEE (2000) GBL (500) |
| | 46 | R-19 | Polymer 19 (100) | PAG-4 (6.0) | Q-2 (8.0) | SF-1 (5.0) | — | PGEE (2000) GBL (500) |

TABLE 2

| | | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| Comparative Example | 10 | R-20 | Comparative Polymer 1 (100) | PAG-2 (12.5) | Q-4 (1.5) | SF-1 (5.0) | — | PGEE (2000) GBL (500) |
| | 11 | R-21 | Comparative Polymer 2 (100) | PAG-4 (10.0) | Q-3 (1.5) | SF-1 (5.0) | XL-1 (5.0) | PGEE (2000) GBL (500) |
| | 12 | R-22 | Comparative Polymer 3 (100) | PAG-3 (12.5) | Q-4 (1.5) | SF-1 (5.0) | XL-1 (5.0) | PGEE (2000) GBL (500) |
| | 13 | R-23 | Comparative Polymer 4 (100) | PAG-1 (10.0) | Q-1 (1.5) | SF-1 (5.0) | XL-1 (5.0) | PGEE (2000) GBL (500) |
| | 14 | R-24 | Comparative Polymer 5 (100) | — | Q-1 (1.5) | SF-1 (5.0) | XL-1 (5.0) | PGEE (2000) GBL (500) |
| | 15 | R-25 | Comparative Polymer 6 (100) | PAG-1 (10.0) | Q-1 (1.5) | SF-1 (5.0) | — | PGEE (2000) GBL (500) |
| | 16 | R-26 | Comparative Polymer 7 (100) | PAG-1 (6.0) | Q-1 (3.5) | SF-1 (5.0) | — | PGEE (2000) GBL (500) |
| | 17 | R-27 | Comparative Polymer 8 (100) | PAG-1 (10.0) | Q-3 (1.5) | SF-1 (5.0) | XL-1 (5.0) | PGEE (2000) GBL (500) |

TABLE 2-continued

| Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|
| 18 | R-28 | Comparative Polymer 9 (100) | PAG-1 (10.0) | Q-3 (1.5) | SF-1 (5.0) | XL-1 (5.0) | PGEE (2000) GBL (500) |

[4] Evaluation of Swell Quantity of Resist During Development, by the QCM (Quartz Crystal Microbalance) Technique Examples 47 to 50 & Comparative Example 19

The above-prepared resist solution (in Tables 1 and 2) was spin coated on a QCM substrate and baked on a hot plate at 100° C. for 60 seconds to form a resist film of 100 nm thick. The resist film was exposed by means of an ArF open-frame exposure system in a dose varying stepwise from 1 mJ/cm$^2$ to 13 mJ/cm$^2$ by an increment of 1 mJ/cm$^2$ and baked (PEB) on a hot plate at the temperature shown in Table 3 for 60 seconds. The QCM substrate was set on a quartz oscillator microbalance instrument RDA-Qz3 for resist development analysis (Litho Tech Japan Co., Ltd.). Development in a 2.38 wt % TMAH aqueous solution was carried out, during which a variation of thickness of resist film was observed as a function of development time. From graphs in which a film thickness variation was plotted relative to development time for each dose, the exposure dose corresponding to the maximum swell quantity and the maximum swell ratio (maximum swell quantity standardized per initial film thickness) are determined, with the results shown in Table 3. A smaller value of maximum swell ratio indicates that the swell of resist film is suppressed.

TABLE 3

| | Resist | PEB temp. (° C.) | Dose (mJ/cm$^2$) | Maximum swell ratio (%) |
|---|---|---|---|---|
| Example 47 | R-02 | 100 | 7 | 133 |
| Example 48 | R-05 | 120 | 6 | 110 |
| Example 49 | R-06 | 100 | 7 | 140 |
| Example 50 | R-07 | 100 | 4 | 116 |
| Comparative Example 19 | R-17 | 100 | 7 | 191 |

As is evident from Table 3, the resist compositions within the scope of the invention show lower maximum swell ratios than the comparative resist compositions.

[5] Etch Resistance Test

Examples 51 to 53 & Comparative Examples 20 to 21

On a silicon wafer which had been surface treated in hexamethyldisilazane (HMDS) gas phase at 90° C. for 60 seconds, the resist solution in Tables 1 and 2 was spin-coated and baked (PAB) on a hot plate at 100° C. for 60 seconds, forming a resist film of 100 nm thick. Using an ArF excimer laser scanner (NSR-307E by Nikon Corp., NA 0.85), the entire surface of the wafer was subjected to open-frame exposure. The exposure dose was 50 mJ/cm$^2$ so that the PAG might generate sufficient acid to induce deprotection reaction. This was followed by PEB at the temperature shown in Table 4 for 60 seconds for promoting dehydration or cross-linking reaction on the base resin of the resist film. The portion where the base resin has underwent dehydration reaction corresponds to the insoluble region in development. A reduction of resist film thickness by exposure and PEB was determined and divided by the initial film thickness, with the result being reported as PEB shrinkage (%).

Further, the resist film was developed in a 2.38 wt % TMAH aqueous solution for 30 seconds. The thickness of the resist film after development was measured. A minimum dissolution rate (nm/sec) was computed from a difference between the film thickness after PEB and the film thickness after development. A lower PEB shrinkage or lower minimum dissolution rate is preferable in that a film thickness necessary for dry etching is retained, or the initial film thickness can be reduced, which is advantageous in terms of resolution. The results are shown in Table 4.

TABLE 4

| | Resist | PEB temp. (° C.) | PEB shrinkage (%) | Minimum dissolution rate (nm/sec) |
|---|---|---|---|---|
| Example 51 | R-08 | 95 | 93 | 0.03 |
| Example 52 | R-09 | 100 | 92 | 0.04 |
| Example 53 | R-10 | 90 | 90 | 0.06 |
| Comparative Example 20 | R-21 | 100 | 85 | 0.05 |
| Comparative Example 21 | R-22 | 100 | 92 | 0.1 |

As is evident from Table 4, the resist compositions within the scope of the invention show a low PEB shrinkage and a slow minimum dissolution rate. As a result, the patterned film is left thick after development, and etch resistance after patterning is high.

[6] ArF Lithography Patterning Test 1

Examples 54 to 69 & Comparative Examples 22 to 29

On a silicon wafer which had been coated with antireflective coating ARC29A (Nissan Chemical Industries, Ltd.) to a thickness of 78 nm, the resist composition (in Tables 1 and 2) was spin coated, then baked on a hot plate at 100° C. for 60 seconds to form a resist film of 100 nm thick. Using an ArF excimer laser scanner NSR-S307E (Nikon Corp., NA 0.85, σ 0.93/0.74, annular illumination), exposure was performed through a 6% halftone phase shift mask bearing a line-and-space pattern with a space width of 90 nm and a pitch of 180 nm, a space width of 80 nm and a pitch of 160 nm or a space width of 70 nm and a pitch of 140 nm (on-wafer size) or a trench pattern with a space width of 90 nm and a pitch of 1,650 nm (on-wafer size) while varying the dose and focus (dose pitch: 1 mJ/cm$^2$, focus pitch: 0.025 μm). After the exposure, the wafer was baked (PEB) at the temperature shown in Table 5 for 60 seconds and puddle developed in 2.38 wt % TMAH aqueous solution for 30 seconds. The wafer was rinsed with deionized water and spin dried, forming a negative pattern. The L/S patterns and trench pattern after development were observed under TD-SEM S-9380 (Hitachi Hitechnologies, Ltd.).

Evaluation of Sensitivity

As an index of sensitivity, the optimum dose (Eop, mJ/cm$^2$) which provided an L/S pattern with a space width of 90 nm and a pitch of 180 nm was determined. A smaller dose value indicates a higher sensitivity.

Evaluation of Exposure Latitude (EL)

The exposure dose which provided an L/S pattern with a space width of 90 nm±10% (i.e., 81 nm to 99 nm) was determined. EL (%) is calculated from the exposure doses according to the following equation:

$$EL(\%) = (|E_1 - E_2|/E_{op}) \times 100$$

wherein $E_1$ is an exposure dose which provides an L/S pattern with a space width of 81 nm and a pitch of 180 nm, $E_2$ is an exposure dose which provides an L/S pattern with a space width of 99 nm and a pitch of 180 nm, and $E_p$ is the optimum exposure dose which provides an L/S pattern with a space width of 90 nm and a pitch of 180 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Depth of Focus (DOP)

As an index of DOP, a range of focus which provided a trench pattern with a space width of 90 nm±10% (i.e., 81 to 99 nm) was determined. A greater value indicates a wider DOP.

Evaluation of Resolution

Resolution is the minimum size that can be resolved among the L/S patterns with a size from 70 nm to 90 nm (pitch 140 to 180 nm). A smaller value indicates better resolution.

The results are shown in Table 5.

As is evident from Table 5, the resist compositions within the scope of the invention have practically acceptable sensitivity. Both EL and DOF have a wide margin. LWR is low as compared with the resists of Comparative Examples. Resolution is also excellent.

[7] ArF Lithography Patterning Test 2

Examples 70 to 73 & Comparative Example 30

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A940 having a silicon content of 43 wt % was deposited thereon to a thickness of 35 nm. On this substrate for trilayer process, the resist composition (in Tables 1 and 2) was spin coated, then baked on a hot plate at 100° C. for 60 seconds to form a resist film of 60 nm thick.

Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 55 nm and a pitch of 110 nm (on-wafer size) while varying the dose and focus (dose pitch: 1 mJ/cm$^2$, focus pitch: 0.025 μm). After the exposure, the wafer was baked (PEB) at the temperature shown in Table 6 for 60 seconds and puddle developed in 2.38 wt % TMAH aqueous solution for 30 seconds. The wafer was rinsed with deionized water and spin dried, obtaining a negative pattern. The CH pattern after development was observed under TD-SEM CG4000 (Hitachi Hitechnologies, Ltd.).

Evaluation of Sensitivity

As an index of sensitivity, the optimum dose (Eop, mJ/cm$^2$) which provided a CH pattern with a hole size of 55 nm and a pitch of 110 nm was determined. A smaller dose value indicates a higher sensitivity.

TABLE 5

|  |  | Resist | PEB temp. (° C.) | $E_{op}$ (mJ/cm$^2$) | EL (%) | LWR (nm) | DOF (μm) | Resolution (nm) |
|---|---|---|---|---|---|---|---|---|
| Example | 54 | R-01 | 100 | 35.8 | 15.3 | 6.5 | 0.18 | 70 |
|  | 55 | R-02 | 100 | 32.5 | 14.5 | 6.2 | 0.18 | 70 |
|  | 56 | R-03 | 110 | 40.3 | 18.6 | 6.8 | 0.18 | 70 |
|  | 57 | R-04 | 100 | 33 | 13.2 | 6.3 | 0.16 | 70 |
|  | 58 | R-05 | 120 | 45.2 | 14.2 | 7.9 | 0.14 | 80 |
|  | 59 | R-06 | 100 | 44.9 | 13.4 | 7.3 | 0.18 | 70 |
|  | 60 | R-07 | 105 | 47.3 | 15.6 | 7.5 | 0.16 | 80 |
|  | 61 | R-08 | 95 | 51 | 16 | 6.1 | 0.16 | 70 |
|  | 62 | R-09 | 100 | 53.2 | 17.2 | 6.3 | 0.18 | 70 |
|  | 63 | R-10 | 90 | 48.5 | 15.8 | 5.9 | 0.18 | 70 |
|  | 64 | R-12 | 95 | 31.2 | 17.5 | 7.2 | 0.18 | 80 |
|  | 65 | R-13 | 100 | 34 | 15.5 | 6.4 | 0.18 | 70 |
|  | 66 | R-25 | 100 | 36 | 15.1 | 6.3 | 0.18 | 70 |
|  | 67 | R-26 | 100 | 38 | 15.7 | 5.9 | 0.14 | 70 |
|  | 68 | R-27 | 100 | 35 | 14.1 | 6.4 | 0.18 | 70 |
|  | 69 | R-28 | 100 | 37 | 15.5 | 6.1 | 0.16 | 70 |
| Comparative | 22 | R-16 | 100 | 36.3 | 9.5 | 10.3 | 0.1 | 90 |
| Example | 23 | R-17 | 95 | 25.3 | 10.5 | 9.8 | 0.08 | 90 |
|  | 24 | R-18 | 110 | 28.3 | 8.3 | 11.5 | 0.1 | 90 |
|  | 25 | R-19 | 100 | 38.5 | 5.6 | 15.2 | 0.12 | 90 |
|  | 26 | R-20 | 100 | 35.6 | 7.5 | 9.5 | 0.08 | 90 |
|  | 27 | R-21 | 110 | 30.5 | 6 | 16.3 | 0.1 | 90 |
|  | 28 | R-22 | 100 | 45.3 | 10.1 | 13.2 | 0.1 | 90 |
|  | 29 | R-23 | 100 | 33.3 | 6.6 | 10.7 | 0.08 | 90 |

Evaluation of Exposure Latitude (EL)

The exposure dose which provided a CH pattern with a hole size of 55 nm±10% (i.e., 49.5 nm to 60.5 nm) was determined. EL (%) is calculated from the exposure doses according to the following equation:

$$EL(\%) = (|E_1 - E_2|/E_{op}) \times 100$$

wherein $E_1$ is an exposure dose which provides a CH pattern with a hole size of 49.5 nm and a pitch of 110 nm, $E_2$ is an exposure dose which provides a CH pattern with a hole size of 60.5 nm and a pitch of 110 nm, and $E_{op}$ is the optimum exposure dose which provides a CH pattern with a hole size of 55 nm and a pitch of 110 nm.

Evaluation of Critical Dimension Uniformity (CDU)

For the CH pattern formed by exposure in the optimum dose (determined in the sensitivity evaluation), the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

The results are shown in Table 6.

TABLE 6

| | Resist | PEB temp. (° C.) | $E_{op}$ (mJ/cm$^2$) | EL (%) | CDU 3σ (nm) |
|---|---|---|---|---|---|
| Example 70 | R-02 | 100 | 24.3 | 9.6 | 7.1 |
| Example 71 | R-08 | 95 | 35.6 | 11.1 | 6.8 |
| Example 72 | R-09 | 100 | 38 | 12.5 | 6.3 |
| Example 73 | R-10 | 90 | 32.2 | 10.5 | 6.7 |
| Comparative Example 30 | R-16 | 100 | 22.3 | 7.2 | 10.1 |

As is evident from Table 6, the resist compositions within the scope of the invention show practically acceptable sensitivity, a wide margin of EL, and excellent CDU.

[8] EB Writing Test

Examples 74 to 77 & Comparative Examples 31 to 32

On a silicon wafer which had been surface treated in HMDS gas phase at 90° C. for 60 seconds, each of the inventive resist compositions or comparative resist compositions in Tables 1 and 2 was spin coated and prebaked on a hot plate at 100° C. for 60 seconds to form a resist film of 60 nm thick. Using an EB lithography system JBX-9000 (JEOL, Ltd.) at an accelerating voltage of 50 kV, a L/S pattern having a space width of 100 nm and a pitch of 200 nm (on-wafer size) was written while varying the dose (dose variation pitch 2 μC/cm$^2$). After the imagewise exposure, the resist film was baked (PEB) at the temperature shown in Table 7 for 60 seconds, puddle developed in 2.38 wt % TMAH aqueous solution for 30 seconds, rinsed with deionized water, and dried, obtaining a negative pattern. The L/S pattern after development was observed under TD-SEM S-9380 (Hitachi Hitechnologies, Ltd.).

Evaluation of Sensitivity

As an index of sensitivity, the optimum dose (Eop, μC/cm$^2$) which provided an L/S pattern with a space width of 100 nm and a pitch of 200 nm was determined. A smaller dose value indicates a higher sensitivity.

Evaluation of Exposure Latitude (EL)

The exposure dose which provided an L/S pattern with a space width of 100 nm±10% (i.e., 90 nm to 110 nm) was determined. EL (%) is calculated from the exposure doses according to the following equation:

$$EL(\%) = (|E_1 - E_2|/E_{op}) \times 100$$

wherein $E_1$ is an exposure dose which provides an L/S pattern with a space width of 90 nm and a pitch of 200 nm, $E_2$ is an exposure dose which provides an L/S pattern with a space width of 110 nm and a pitch of 200 nm, and $E_{op}$ is the optimum exposure dose which provides an L/S pattern with a space width of 100 nm and a pitch of 200 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

TABLE 7

| | Resist | PEB temp. (° C.) | $E_{op}$ (μC/cm$^2$) | EL (%) | LWR (nm) |
|---|---|---|---|---|---|
| Example 74 | R-02 | 100 | 43.5 | 13.5 | 5.2 |
| Example 75 | R-11 | 95 | 50.3 | 18.6 | 4.5 |
| Example 76 | R-14 | 110 | 35.6 | 13.8 | 5.1 |
| Example 77 | R-15 | 115 | 38 | 14.2 | 5.8 |
| Comparative Example 31 | R-16 | 100 | 42.2 | 8.6 | 8.9 |
| Comparative Example 32 | R-24 | 105 | 53.5 | 7.2 | 9.5 |

As is evident from Table 7, the resist compositions within the scope of the invention show practically acceptable sensitivity, a wide margin of EL, and low LWR.

Japanese Patent Application Nos. 2014-256295 and 2015-179394 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer consisting of recurring units having the formula (3), and recurring units of at least one type selected from recurring units having formulae (A) to (D), and optionally recurring units of at least one type selected from recurring units having formulae (f1) to (f3):

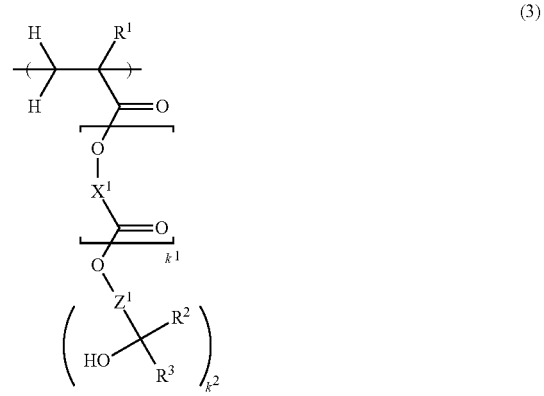

(3)

wherein $R^1$ is hydrogen or methyl, $R^2$ and $R^3$ are each independently an unsubstituted straight, branched or cyclic $C_1$-$C_{10}$ monovalent hydrocarbon group, $R^2$ and $R^3$ may bond together to form an alicyclic group with the carbon atom to which they are attached, $X^1$ is a straight, branched or cyclic $C_1$-$C_{20}$ divalent hydrocarbon group in which any constituent —CH$_2$— moiety may be replaced by —O— or —C(=O)—, Z$^1$ is a straight, branched or cyclic C$_1$-C$_{20}$ aliphatic hydrocarbon group in which any constituent —CH$_2$— moiety may be replaced by —O— or —C(=O)—, k' is 0 or 1, and k$^2$ is an integer of 2 to 4, wherein when k$^2$ is 2, Z$^1$ is selected from the group consisting of the following formulae:

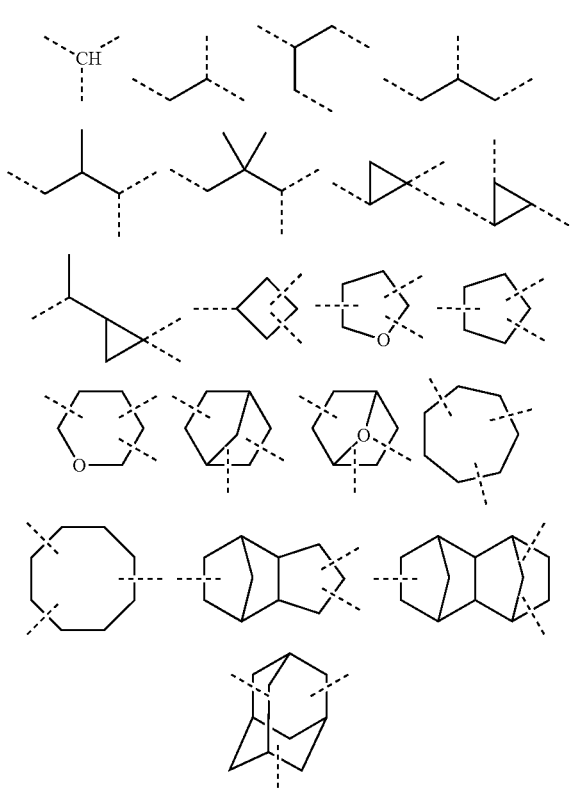

when k$^2$ is 3, Z$^1$ is:

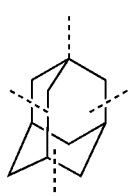

and when k$^2$ is 4, Z$^1$ is:

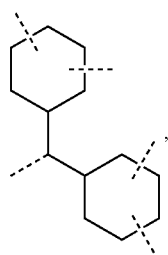

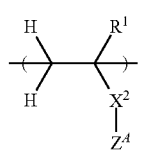
(A)

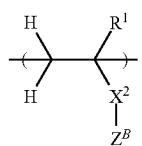
(B)

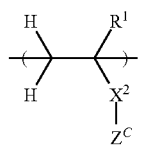
(C)

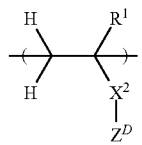
(D)

wherein R$^1$ is as defined above, Z$^A$ is a C$_1$-C$_{20}$ fluoroalcohol-containing group, Z$^B$ is a C$_1$-C$_{20}$ phenolic hydroxyl-containing group, Z$^C$ is a C$_1$-C$_{20}$ carboxyl-containing group, Z$^D$ is a substituent group having a lactone structure, sultone structure, carbonate structure, cyclic ether structure, acid anhydride structure, alkoxycarbonyl, sulfonamide or carbamoyl moiety, X$^2$ is a single bond, methylene, ethylene, phenylene, fluorinated phenylene, naphthylene, —O—R$^{01}$—, or —C(=O)—Z$^2$—R$^{01}$—, Z$^2$ is oxygen or NH, and R$^{01}$ is a straight, branched or cyclic C$_1$-C$_6$ alkylene, straight, branched or cyclic C$_2$-C$_6$ alkenylene, phenylene or naphthylene group, which may contain a carbonyl, ester, ether or hydroxyl moiety,

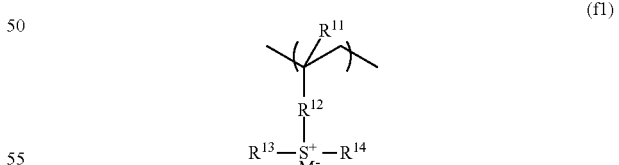
(f1)

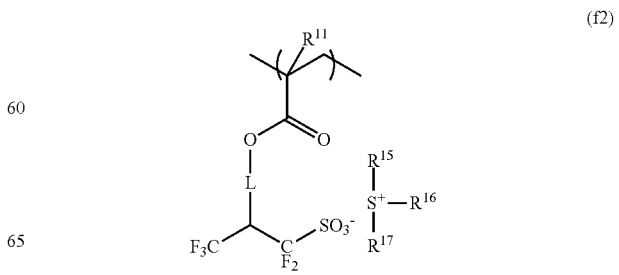
(f2)

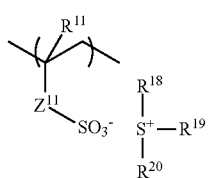

wherein $R^{11}$ is each independently hydrogen or methyl, $R^{12}$ is a single bond, phenylene, —O—$R^{21}$—, or —C(=O)—$Z^{22}$—$R^{21}$— wherein $Z^{22}$ is oxygen or NH and $R^{21}$ is a straight, branched or cyclic $C_1$-$C_6$ alkylene group, straight, branched or cyclic $C_2$-$C_6$ alkenylene group or phenylene group, which may contain a carbonyl (—CO—), ester (—COO—), ether (—O—) or hydroxyl moiety, L is a single bond or —$Z^{33}$—C(=O)—O— wherein $Z^{33}$ is a straight, branched or cyclic $C_1$-$C_{20}$ divalent hydrocarbon group which may be substituted with a heteroatom, $Z^{11}$ is a single bond, methylene, ethylene, phenylene, fluorinated phenylene, —O—$R^{22}$—, or —C(=O)—$Z^{44}$—$R^{22}$— wherein $Z^{44}$ is oxygen or NH and $R^{22}$ is a straight, branched or cyclic $C_1$-$C_6$ alkylene group, straight, branched or cyclic $C_2$-$C_6$ alkenylene group or phenylene group, which may contain a carbonyl, ester, ether or hydroxyl moiety, $M^-$ is a non-nucleophilic counter ion, $R^{13}$ to $R^{20}$ are each independently a straight, branched or cyclic $C_1$-$C_{30}$ monovalent hydrocarbon group which may be substituted with or separated by a heteroatom, a pair of $R^{13}$ and $R^{14}$ may bond together to form a ring with the sulfur atom to which they are attached, and any two or more of $R^{15}$, $R^{16}$ and $R^{17}$, or any two or more of $R^{18}$, $R^{19}$ and $R^{20}$ may bond together to form a ring with the sulfur atom to which they are attached.

2. A resist composition comprising a base resin, an acid generator, and an organic solvent, the base resin comprising the polymer of claim 1.

3. A pattern forming process comprising the steps of applying the resist composition of claim 2 onto a substrate, baking to form a resist film, exposing the resist film to high-energy radiation to define exposed and unexposed regions, baking, and developing the exposed resist film in a developer to form a pattern.

4. The pattern forming process of claim 3 wherein the developing step uses an alkaline developer in which the unexposed region of resist film is dissolved and the exposed region of resist film is not dissolved, for forming a negative tone pattern.

5. The resist composition of claim 2 which does not comprise a crosslinker.

6. The polymer of claim 1 wherein $R^2$ and $R^3$ are each independently methyl, ethyl, propyl, isopropyl, n-butyl, s-butyl, t-butyl, cyclopentyl, cyclohexyl, 2-ethylhexyl, n-octyl, norbornyl, tricyclodecanyl, or adamantly.

7. The polymer of claim 6 wherein $R^2$ and $R^3$ are each independently methyl or ethyl.

8. The polymer of claim 1 wherein the recurring units having the formula (3) are selected from the group consisting of the following formulae:

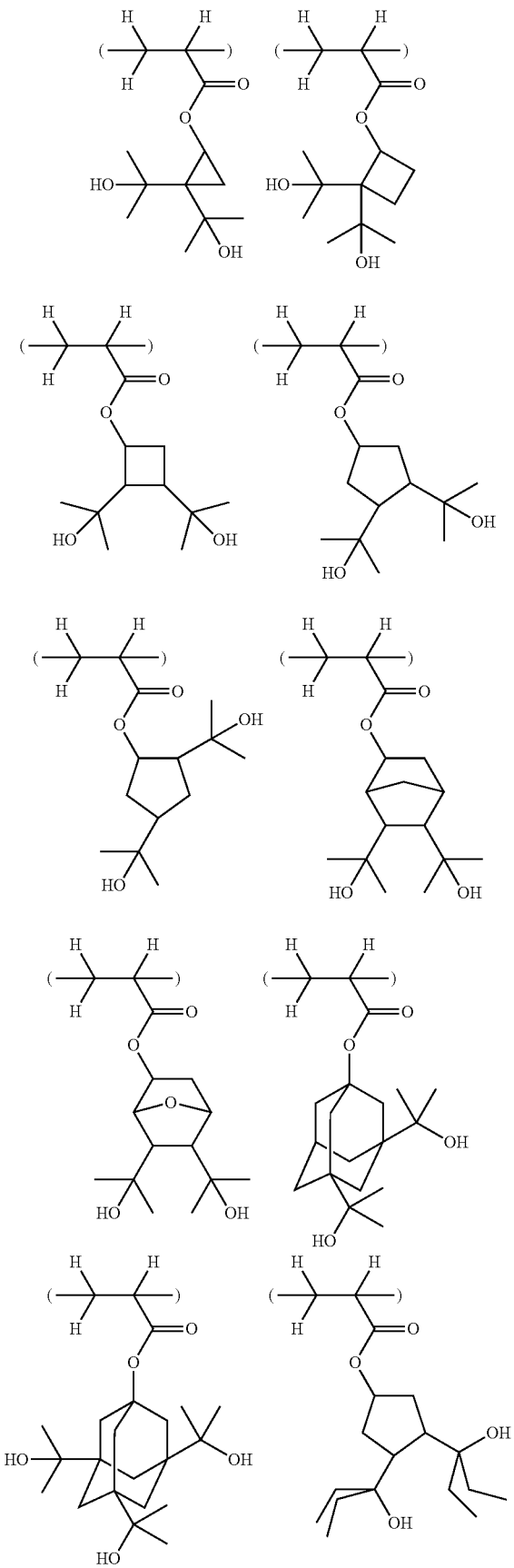

159
-continued
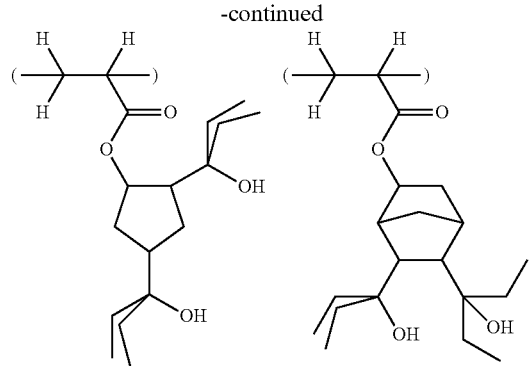
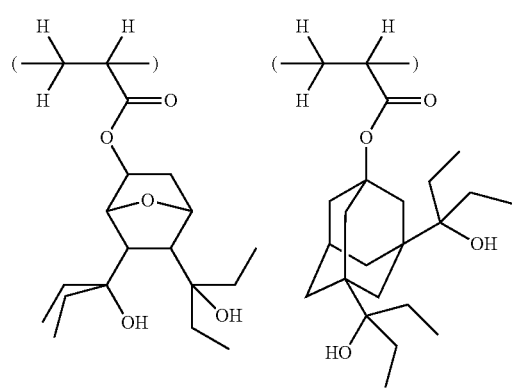
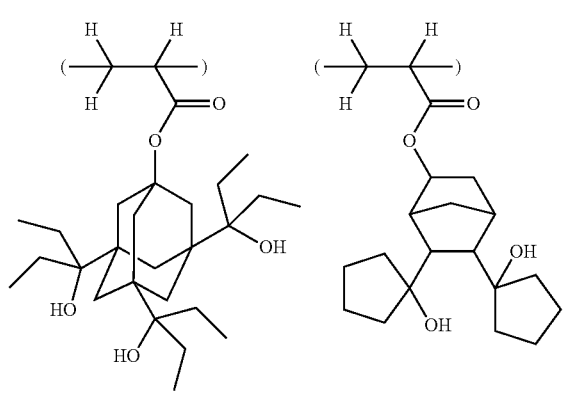
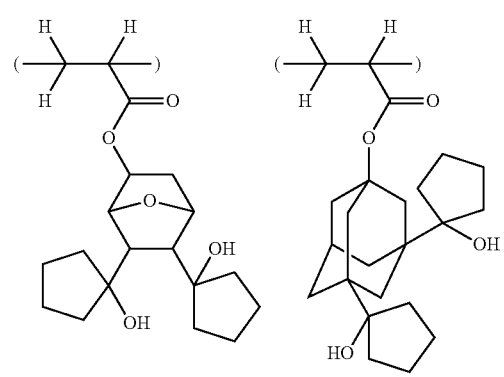
160
-continued
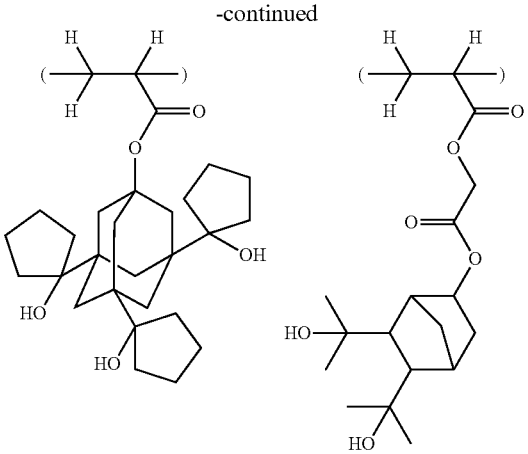
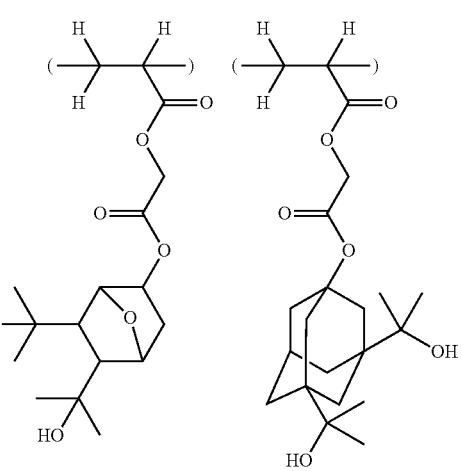
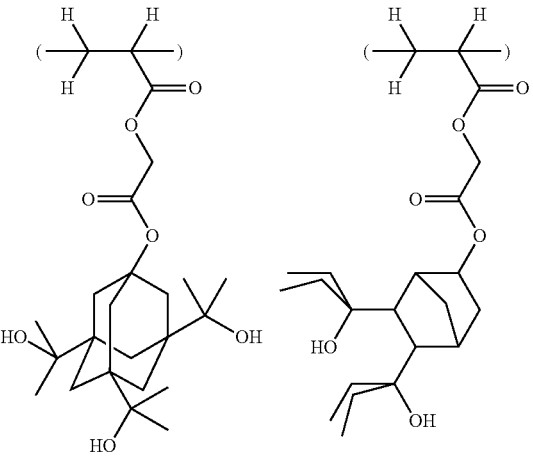

161
-continued
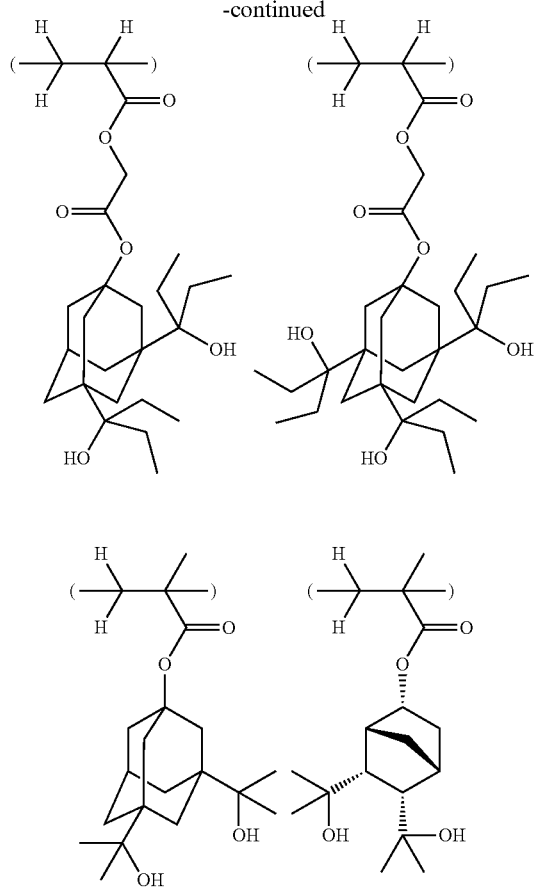
162
-continued
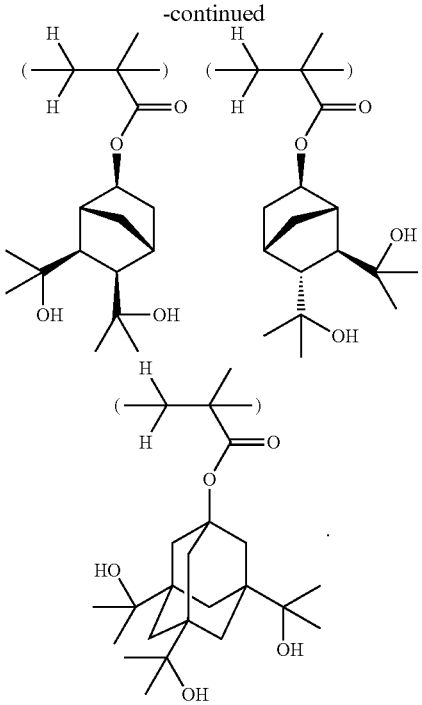
9. The polymer of claim 1 wherein the amounts of recurring units of formula (3), recurring units of at least one type selected from units (A) to (D), and recurring units of at least one type selected from units (f1) to (f3) are 5 to 80 mol %, 20 to 95 mol %, and 0 to 30 mol %, respectively.
* * * * *